Figure 1:
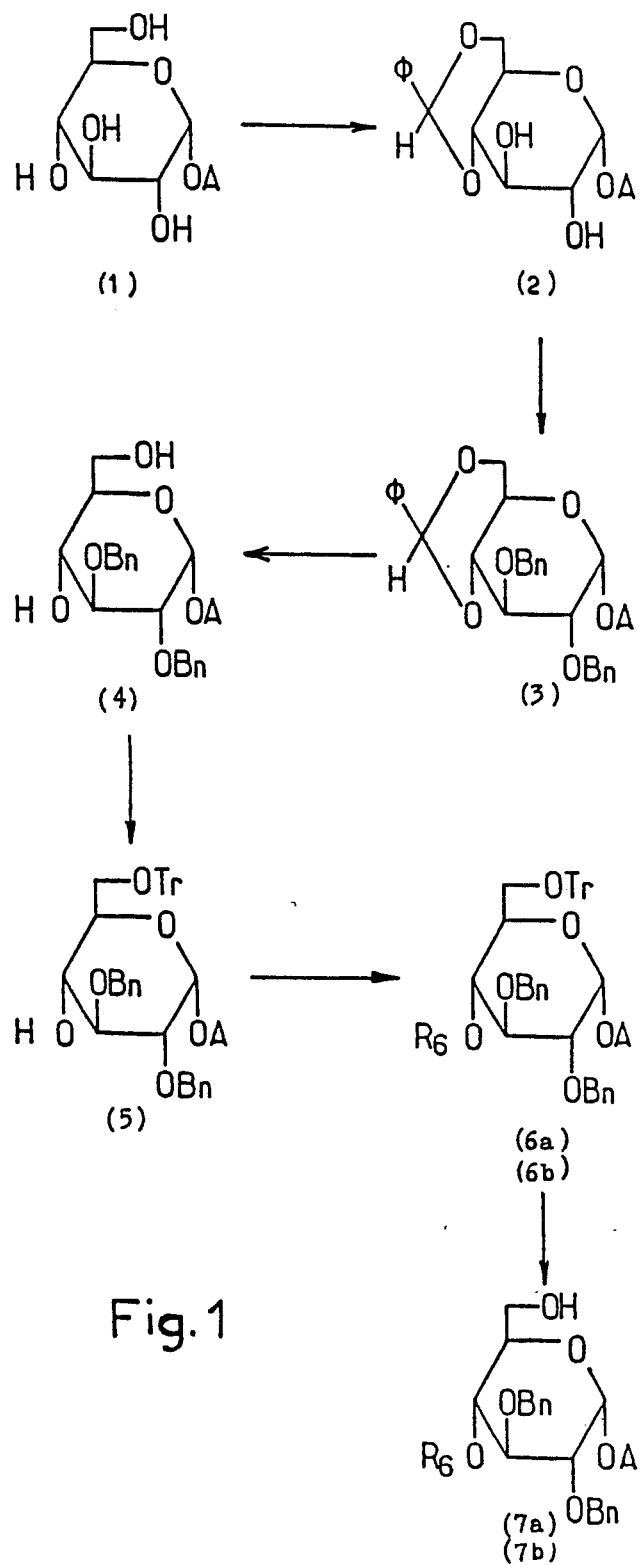
Figure 2:
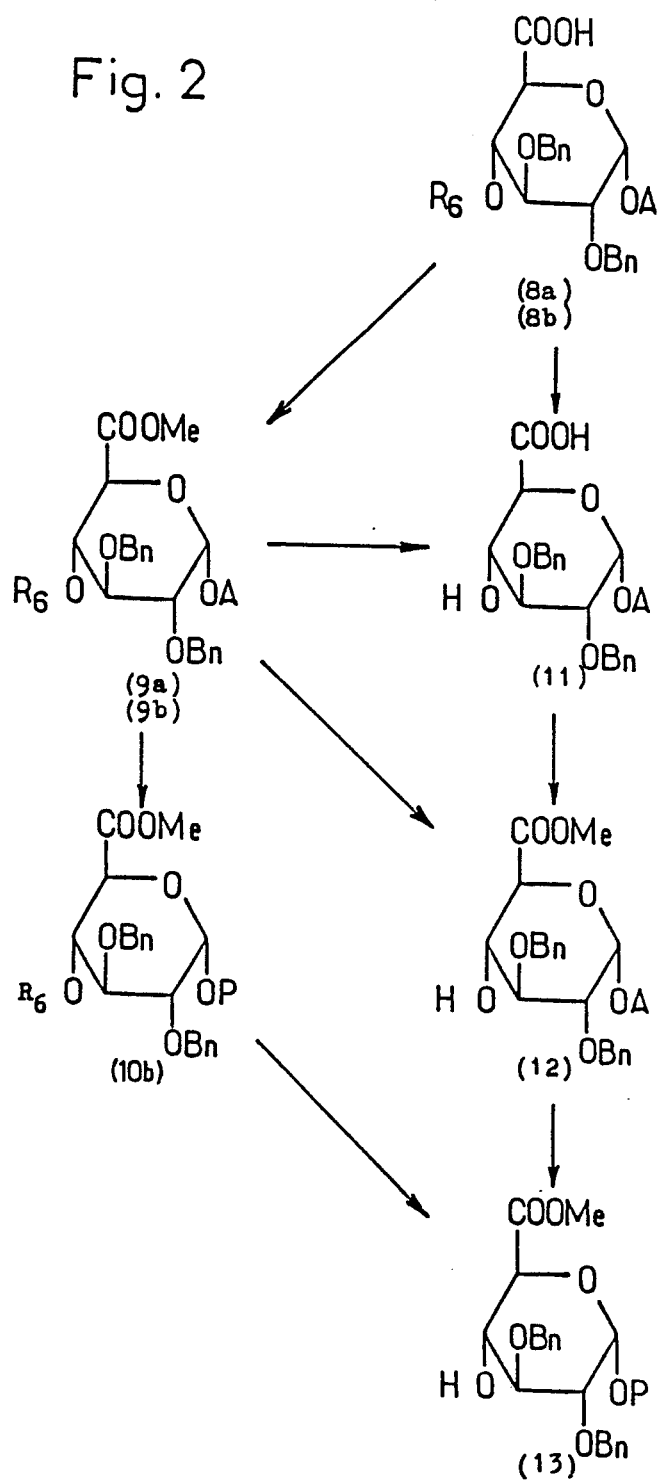
Figure 3:
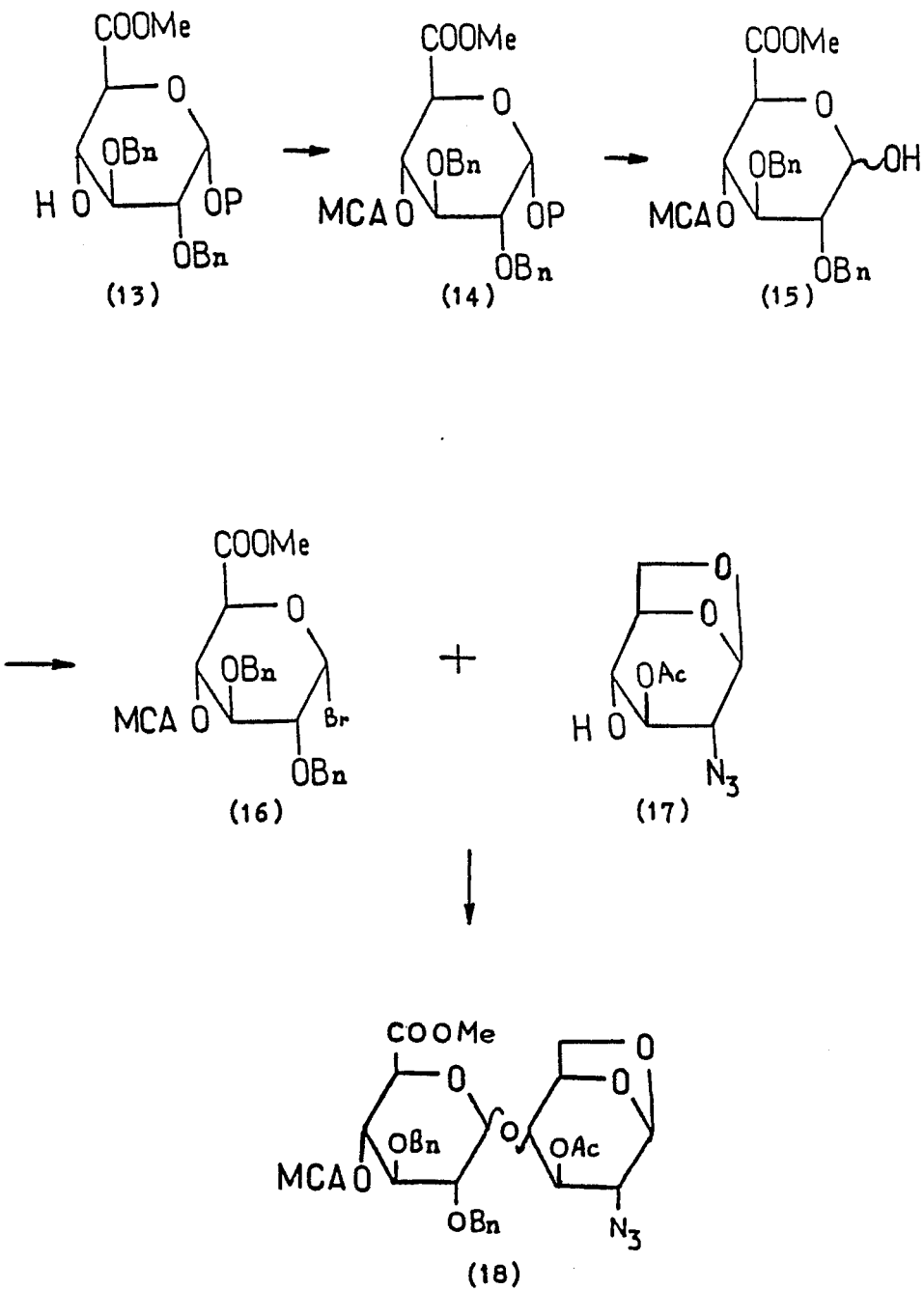
Figure 6:
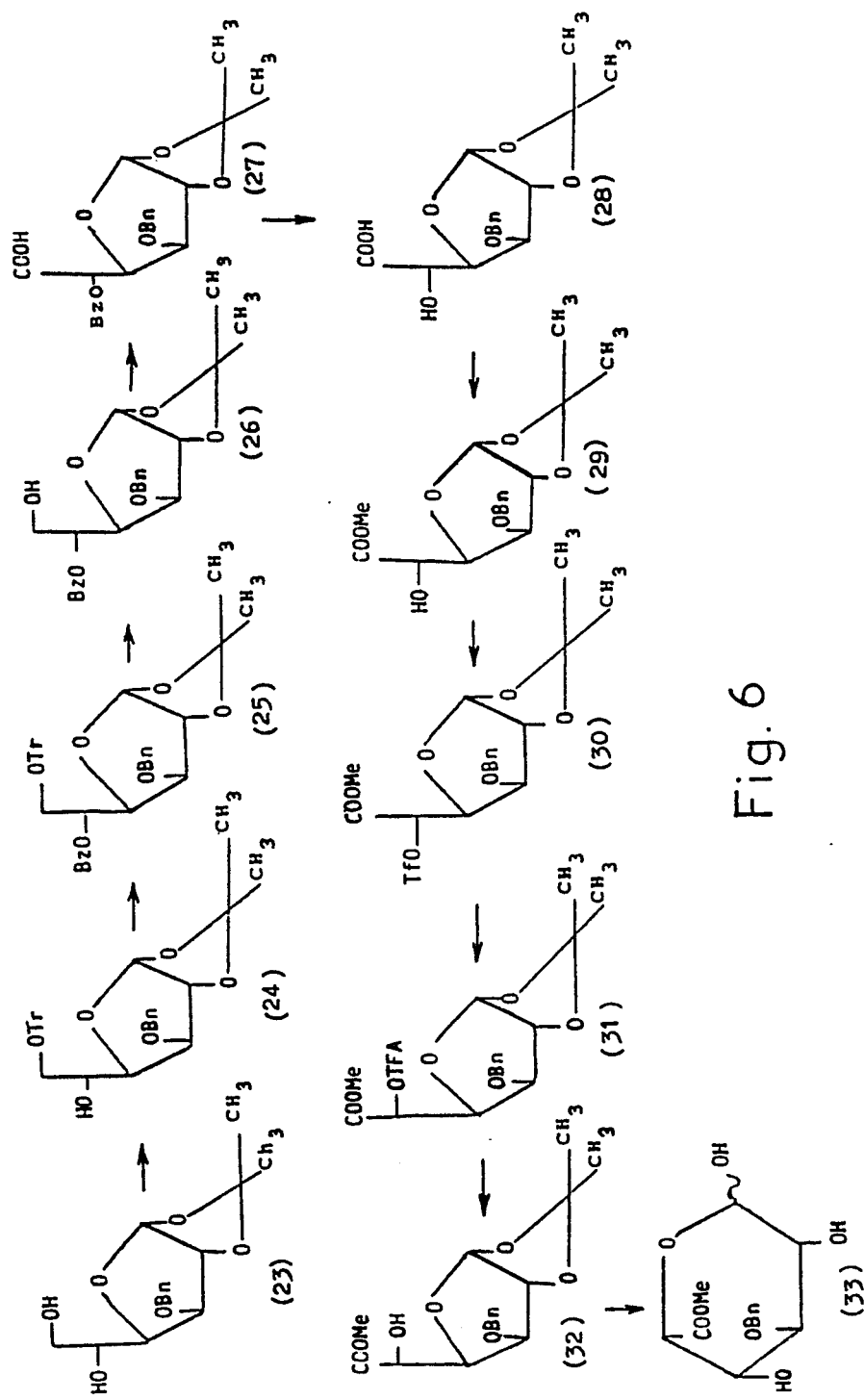

United States Patent [19]

Petitou et al.

[11] Patent Number: 4,818,816

[45] Date of Patent: * Apr. 4, 1989

[54] PROCESS FOR THE ORGANIC SYNTHESIS OF OLIGOSACCHARIDES AND DERIVATIVES THEREOF

[75] Inventors: Maurice Petitou, Paris; Jean-Claude Jacquinet; Pierre Sinay, both of Orleans la Source; Jean Choay, Paris; Jean-Claude Lormeau, Maromme, all of France; Mahmoud Nassr, Alexandria, Egypt

[73] Assignee: Choay, S.A., Paris, France

[ * ] Notice: The portion of the term of this patent subsequent to Aug. 19, 2003 has been disclaimed.

[21] Appl. No.: 115,593

[22] Filed: Oct. 26, 1987

Related U.S. Application Data

[63] Continuation of Ser. No. 457,931, Jan. 14, 1983, abandoned, which is a continuation-in-part of Ser. No. 451,615, Dec. 20, 1982, Pat. No. 4,607,025.

[51] Int. Cl.$^4$ .................. C07H 5/04; C07H 11/04; C07H 11/00; C07H 1/00
[52] U.S. Cl. .................. 536/55.2; 536/55.3; 536/117; 536/118; 536/124; 514/822
[58] Field of Search ............ 536/55.2, 55.3, 124, 536/117, 118; 514/56, 62

[56] References Cited

U.S. PATENT DOCUMENTS

| | | | |
|---|---|---|---|
| 3,075,965 | 1/1963 | Touey et al. | 536/118 |
| 3,437,653 | 4/1969 | Curtin et al. | 536/117 |
| 4,064,339 | 12/1977 | Coussediere et al. | 536/16.6 |
| 4,207,413 | 6/1980 | Szarak et al. | 536/1.1 |
| 4,221,907 | 9/1980 | Nair et al. | 536/118 |
| 4,401,662 | 8/1983 | Lormeau et al. | 536/21 |
| 4,401,758 | 8/1983 | Lormeau et al. | 536/21 |
| 4,435,387 | 10/1982 | Schaub et al. | 514/24 |
| 4,474,770 | 10/1984 | Lormeau et al. | 536/21 |

FOREIGN PATENT DOCUMENTS

| | | |
|---|---|---|
| 0014184 | 8/1980 | European Pat. Off. . |
| 0027089 | 4/1981 | European Pat. Off. . |
| 0048231 | 3/1982 | European Pat. Off. . |
| 0064012 | 11/1982 | European Pat. Off. . |
| 7900031 | 11/1979 | France .................. 536/123 |

OTHER PUBLICATIONS

Bulletin of the Academy of Science USSR, Div. of Chem. Science, Kochetkov et al., (Izvestiya Akademii Nauk SSSR Seriya Khimicheskaya) vol. 26, No. 6, pp. 1305–1311, Jan. 1975.
Henikoff et al.; Nature 289; 33 (1981).
Tetrahedron Letters No. 5, Klemer, pp. 431–433, 1972.
Tetrahedron Letters No. 30, Kiss and Wyss, pp. 3055–3058, 1972.
Carbohydrate Research, vol. 105, No. 1, Ogamo et al. Jul. 1, 1982.
Carbohydrate Research, vol. 103, No. 1, Seno, May 1, 1982.
Carbohydrate Research, vol. 78, No. 2, Klein, Jan. 15, 1980.
Carbohydrate Research, vol. 87, No. 2, Ayotte et al., Dec. 15, 1980.
Bulletin de la Societe de Chimie Bilogique, Tome XLII, 1960, Nos. 9–10, Barker et al., 25 Jan. 1961.
(List continued on next page.)

Primary Examiner—John Rollins
Attorney, Agent, or Firm—Davis, Hoxie, Faithfull & Hapgood

[57] ABSTRACT

The invention relates to a process for the organic synthesis of oligosaccharides constituting or comprising fragments of acid mucopolysaccharides comprising the reaction of two compounds constituted or terminated by units of glucosamine structure and of uronic acid structure respectively, said units being specifically substituted. This process particularly enables valuable anticoagulant drugs to be obtained.

61 Claims, 32 Drawing Sheets

OTHER PUBLICATIONS

Helvetica Chimica Acta, H.C.A. vol. 58, Fascs 6, Wyss et al., pp. 1847–1860.
The Journal of Biochemistry, vol. 92, No. 1, Kosoia, Jul. 1982.
IUPAC Pure & Applied Chemistry, vol. 50, Sinay, pp. 1437–1452.
Angewandte Chemie, vol. 21, No. 3, Paulsen, Mar. 1982, pp. 155–224.
Organic Chemistry, 2nd Ed., Louis F. Fieser & Mary Fieser, pp. 229–232.
Methods in Carbohydrate Chemistry, vol. VIII, 1980 Marthorpe, pp. 305–311.
Clinica Chemica Acta, 123, Hopwood, pp. 241–250, 8/82.
J. Chem. Soc., 1962 Turvey and Williams pp. 2119–2122.

Fig. 4
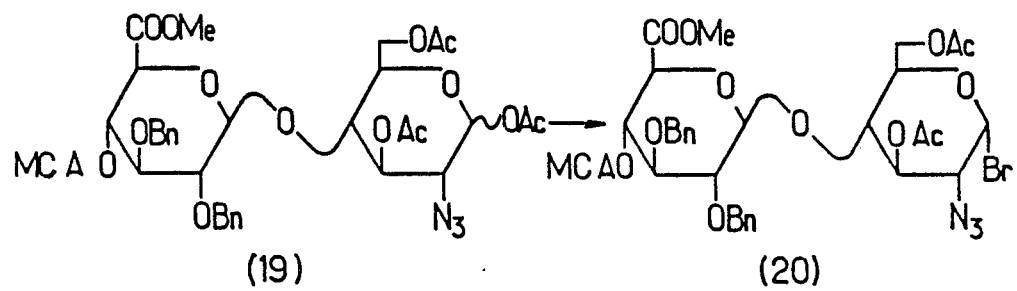
Fig. 5
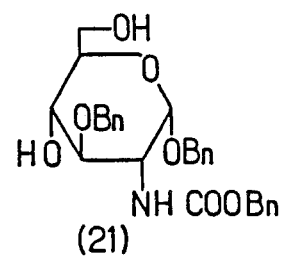
(21)
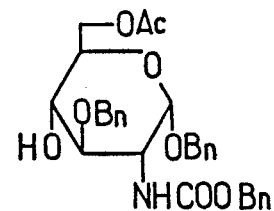
(22)

Fig.7
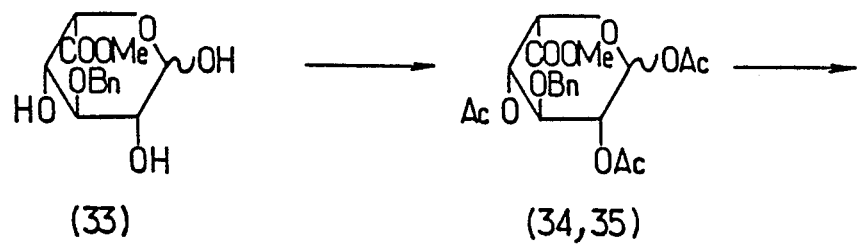
(33) → (34,35) →
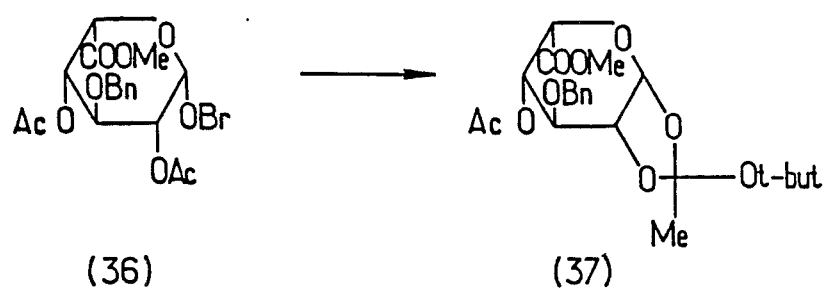
(36) → (37)
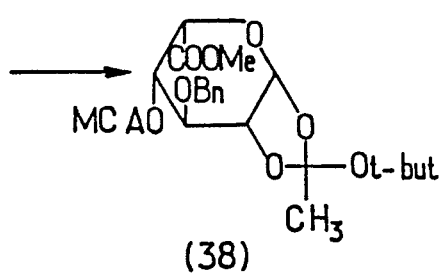
(38)
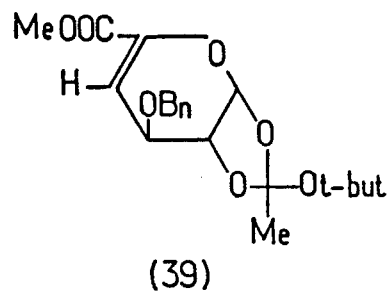
(39)

Fig.16
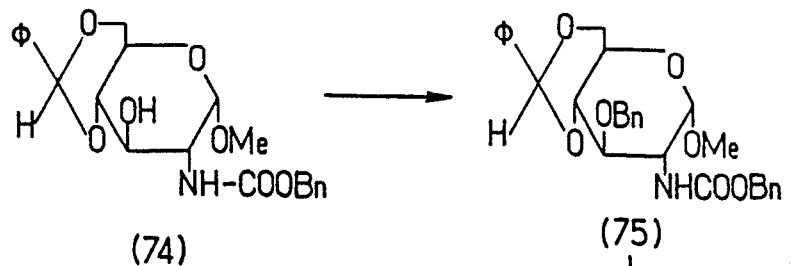
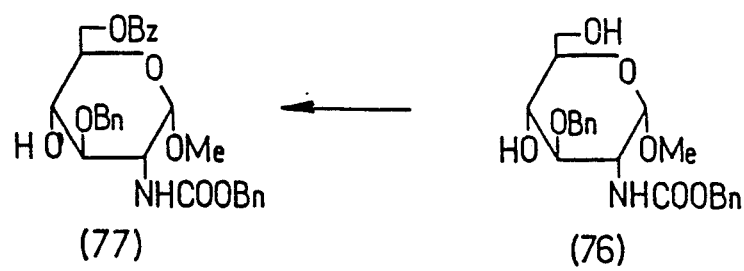
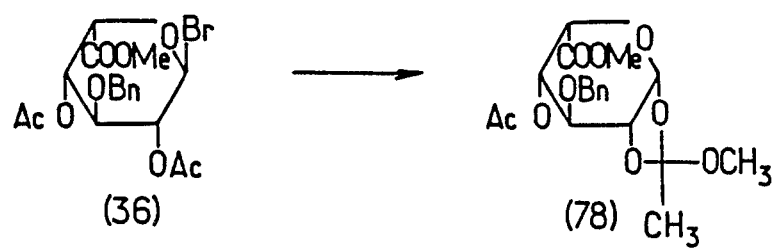
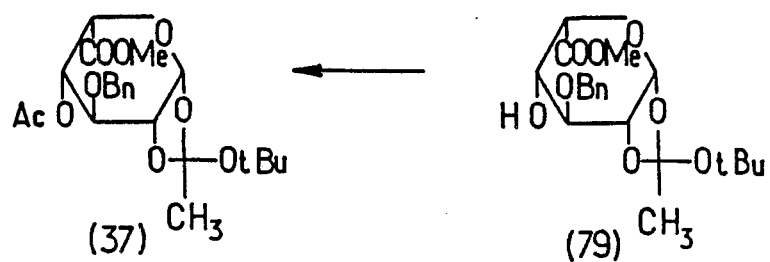

Fig.17
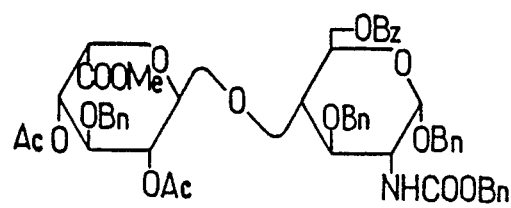
(81)
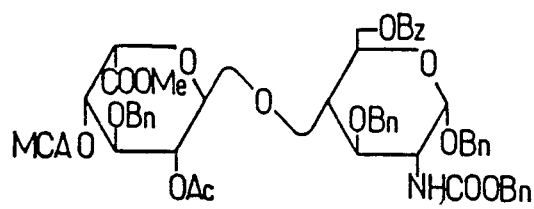
(82)
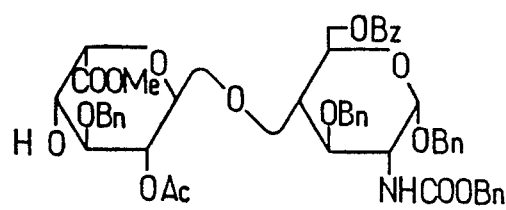
(83)

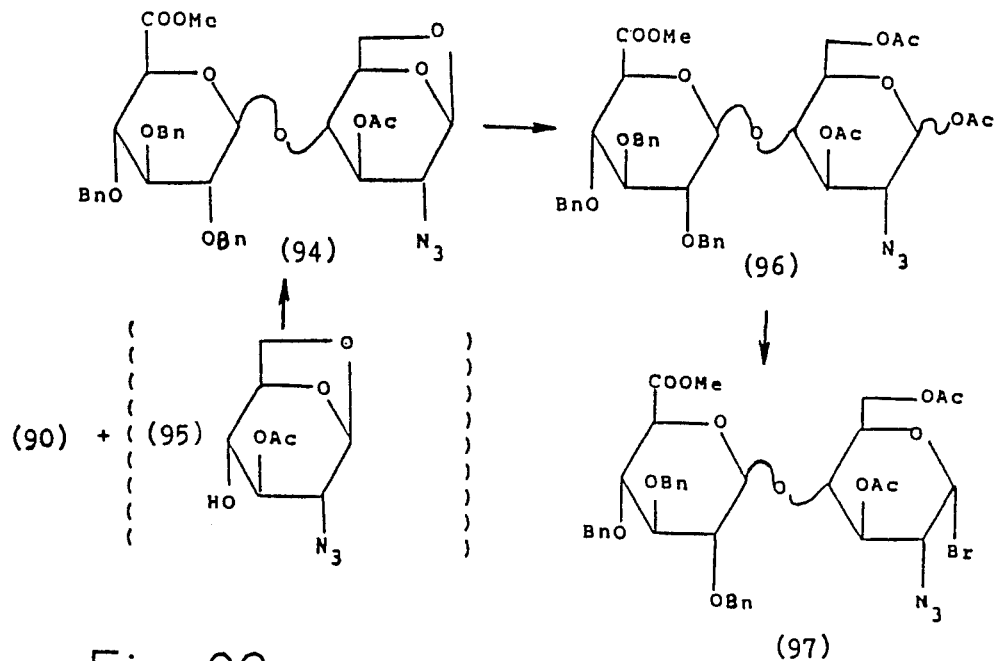
Fig. 20
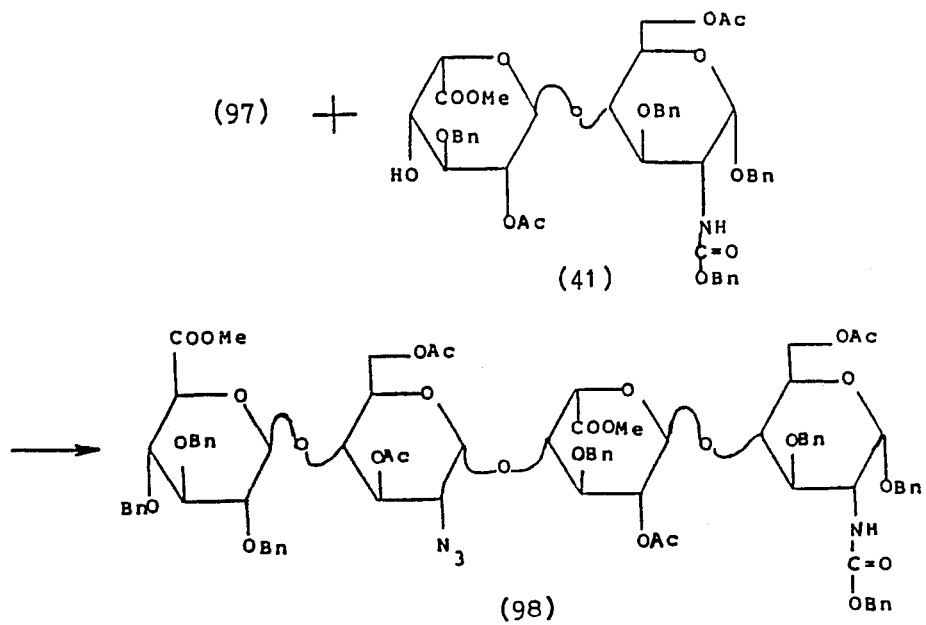

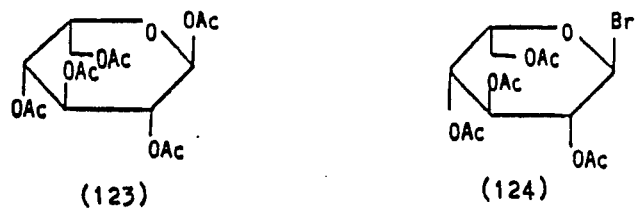
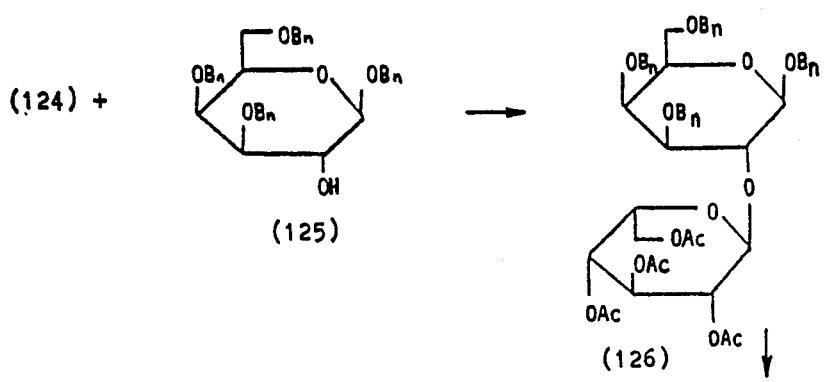
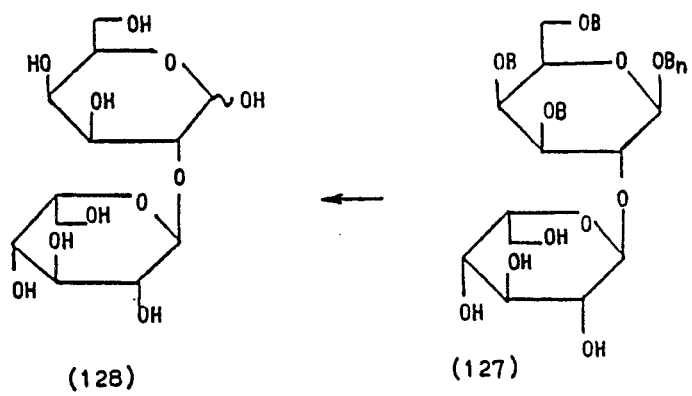
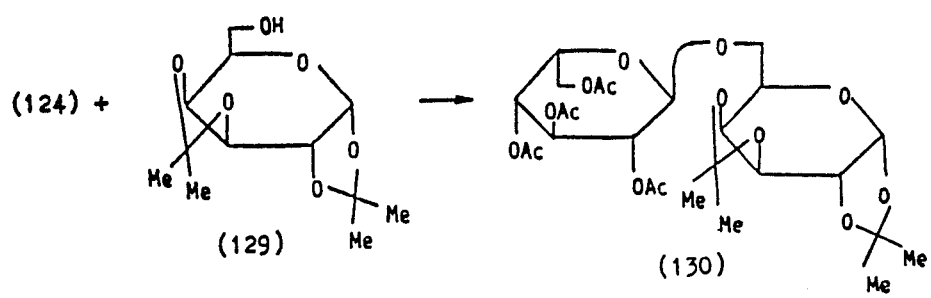
Fig. 24

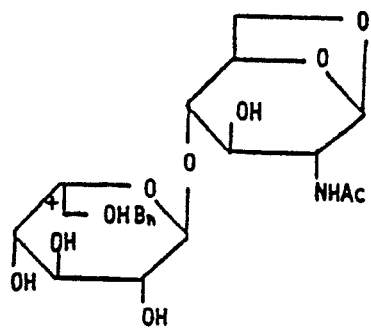
(137)
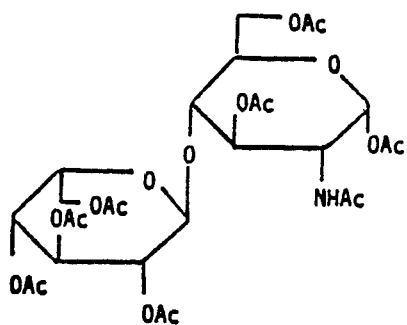
(138)
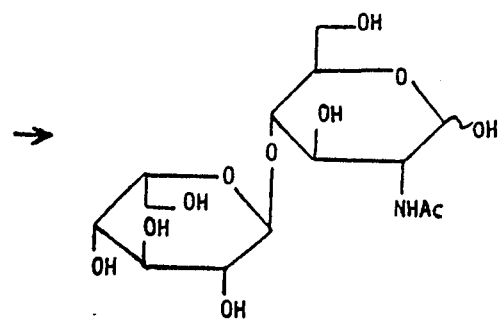
(139)
Fig. 26

PROCESS FOR THE ORGANIC SYNTHESIS OF OLIGOSACCHARIDES AND DERIVATIVES THEREOF

This is a continuation of co-pending application Ser. No. 457,931, filed on Jan. 14, 1983, now abandoned, which is a continuation-in-part of application Ser. No. 451,615, filed Dec. 20, 1982, which was issued as U.S. Pat. No. 4,607,025 on Aug. 19, 1986.

FIELD OF THE INVENTION

The invention relates to a process for the organic synthesis of oligolsaccharides constituting or comprising fragments of acid mucopolysaccharides. It also relates to the synthesis of derivatives of these oligosaccharides.

The invention relates, in addition, to novel oligosaccharides of the above-indicated type and to their derivatives, possessing, particularly, biological properties conferring on them, in particular, interest as medicaments and/or useful, for example, as laboratory reagents.

It is directed also to their uses particularly their biological and biochemical uses.

By the term "acid mucopolysaccharide", is meant derivatives also currently called glycosaminoglycuronoglycanes. It concerns oligosaccharides and polysaccharides encountered more especially in chains of biologically active derivatives such as derivatives of the heparin and heparane-sulphate type.

In natural products, the mucopolysaccharides concerned are essentially formed of alternate amino-sugar-uronic acid units, or conversely. In these units, the amino-sugar, denoted below by A, has more especially a D-glucosamine structure. The uronic acid, which will be called U, has, more especially, a D-glucuronic acid or L-iduronic acid structure.

The basic structure for A corresponds respectively to the formyal a and for U to the formulae b and c below:

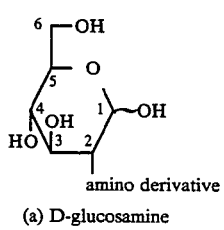

(a) D-glucosamine amino derivative

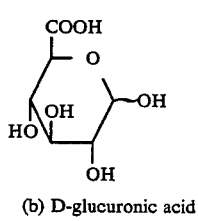

(b) D-glucuronic acid

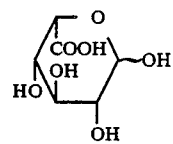

(c) L-iduronic acid

In the natural products concerned, these various units are linked to one another stereo-specifically generally by

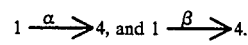

Thus, for example in heparin, linkages of the type

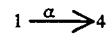

(between the c and a, a and b, and a and c units) and of the type

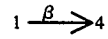

(between the b and a units), are to be found.

It will be noted, also, still with reference to natural products, that the above units comprise specific substitutions, that is to say certain substitutions at given positions. The chains of natural products contain, thus, for example, -O-substituted units 2-O-sulphate-L-iduronic acid, 3-O-sulphate-D-glucosamine, 3,6-di-O-sulphate-D-glucosamine, 6-O-sulphate-D-glucosamine, and non-O-substituted units, like, for example, units D-glucuronic acid, L-iduronic acid and D-glucosamine.

In addition, the unit a is N-substituted at the 2 position of the —N-acetyl and/or —N-sulphate groups.

DESCRIPTION OF THE PRIOR ART

The importance of the therapeutic uses of the above acid mucopolysaccharides is known, in particular, for the preventin and treatment of disorders of cloting and of the vascular wall, and in particular thromboses and atheroscleroses and arterioscleroses.

Moreover the numerous researches of Applicant are known for the obtaining of fragments of high affinity for AT III and biologically active fragments from heparin chains. The inventions developed on the basis of these researches are the subject of various patent applications among which are patent application EP No. 80 40 1425.6 of Oct. 6, 1980 and patent application FR No. 81 08604 of Apr. 29, 1981.

It is recalled that in the EP application, there is described in particular an octasaccharide called ABC-DEFGH possessing anti-thrombotic properties of great interest, corresponding to the structure:

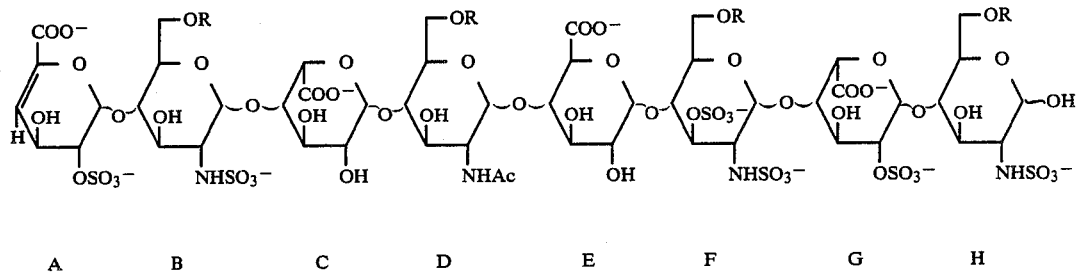

A B C D E F G H

In this formula, R represents a $SO_3^-$ group or a hydrogen atom.

In the above FR patent application of Applicant, a homogeneous hexasaccharide composition of the structure C'DEFGH is described, also possessing high antithrombotic properties. This structure corresponds to the formula:

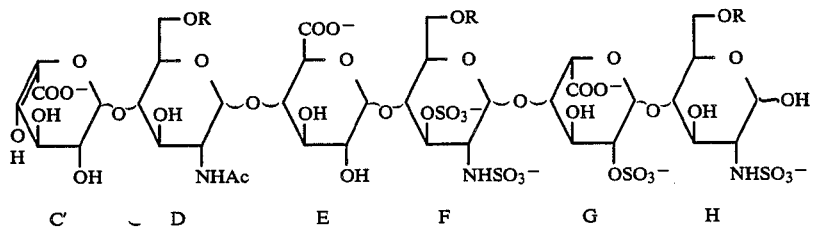

C' D E F G H in which R represents an $SO_3^-$ group or a hydrogen atom.

The methods proposed until now to obtain this type of product bring into play extraction techniques from heparin or from products obtained in the course of the prepartion of heparin, or again depolymerisation techniques of heparin chains under the action of a chemical or enzymatic agent, followed by specific fractionation particularly by affinity chromatogrpahy.

The progress of the researches of Applicants in this field has led them to investigate novel means enabling this type of product to be obtained and more especially study of the possibilities of obtaining them synthetically.

In this respect, it is appropriate to measure the number of problems raised by such synthesis. In fact, on the one hand, these products contain in their chains several types of A and U units. On the other hand, the linkages between these units correspond to a given stereo-chemistry and are of the 1,4 type, of which the particular difficulties of production are well-known. In addition, each unit comprises one or several specific substitutions according to the type of procudt concerned. It is to be considered also that the glucosamine units in natural products comprise two nitrogenous groups different from one another, namely an N-acetyl group and an —N-sulphate group.

It follows that such syntheses have practically never been contemplated until now in the scientific literature, more particularly, as regards L-iduronic acid.

All these elements highlight the restrictive requirements of which it is easy to appreciate the difficulties that they involve for the development of a general process and of the process of synthesis.

By researching conditions of oside synthesis suitable for the development of this type of compound, Applicants have developed a strategy by selecting certain particular types of protection for the substances utilised.

The work carried out has then shown that with such so-protected substances, it was possible to produce a stereo-specific chain formation and then to introduce, if desired, into the sequences formed, given substitutions as predetermined positions.

According to one aspect presenting an interest of which the importance will be measured, the process developed has great flexibility. It is thus possible to arrive at, with the advantages in particular of specificity and purity associated with a synthetic process, numerous oligosaccharide derivatives including the specific substitutions encountered with natural products, or even different substitutions and/or again units of similar structure with different configurations.

Due to this process, Applicants have obtained oligosaccharides endowed in particular with medicinal properties of great value and more especially high antithrombotic activity. The process of the invention also permits access to a large number of particularly valuable oligosaccharides, in particular for biological reagents and/or for reference compounds for structure studies.

It is therefore an object of the invention to provide a process for producing, synthetically, oligosaccharides and their derivatives or the like, including or corresponding to fragments of acid mucopolysaccharides.

It is also an object to provide means enabling the establishment between A and U type units of glycoside linkages in the desired stero-specificity.

It is also an object to provide means enabling the introduction into the units of the glycoside chain of given functional groups, in particular of specific substituents such as encountered in the chains of biologically active molecules, particularly those of the heparin and heparane-sulphate type.

It is also an object to provide means enabling the production of oligosaccharides such as mentioned above, but of which the substituents and/or the chemical nature of the sugars and/or the position and configuration of the inter-glycoside linkages and/or the configuration of the monosaccharides and/or the order of the enchainments are different from those of natural products.

According to another aspect, it is also an object of the invention to provide novel oligosaccharides constituting intermediate products of the process of synthesis concerned in which all the —OH groups of the various units are blocked by protective groups and the precursor groups of the functional radicals possibly present; if necessary, these radicals themselves are also protected.

According to yet another aspect, the invention is aimed at providing novel oligosaccharides having the structure of the above natural products as well as oligosaccharides corresponding to fragments of these products.

It is also directed at providing novel oligosaccharides possessing specific substitutions of natural products.

It is also an object of the inventin to provide novel oligosaccharides bearing substitutions different from the specific substitutions concerned and/or including different units with respect to the natural products considered above.

The invention also relates to the biological uses of these oligosaccharides, particularly as active medicinal substances, laboratory agents or reference substances for the study, in particular, of compounds including this type of structure.

GENERAL DESCRIPTION OF THE INVENTION

The process of synthesis of the invention is characterized in that it brings about the reaction of two compounds:
constituted or terminated respectively by A units of glucosamine structure, in particular D-glucosamine, and U units of glucuronic acid structure, in particular D-glucuronic, or iduronic acid, in particular L-iduronic acid;
one of the units A or U being an alcohol in which the —OH group of the alcohol function occupies any one of the positions 3, 4 or 6 in the case of unit A and 2, 3 or 4 in the case of unit U, the other unit possessing an activated anomeric carbon, that is to say comprising a reactive group capable of establishing with the —OH group of the alcohol the desired glycosylation —O— linkage, in the desired stereo-chemistry, to form a —A—U or —U—A sequence;
the reactive group of A and U being compatible with the protective groups and/or functional groups present on the units;
all the position of A and U excepted those of which the anomeric carbon is activated bearing —OH, amino or carboxyl groups, or precursors of such groups, the groups themselves, when they are present being blockwed by one or advantageously several types of protective groups, these various groups being compatible with one another and with the above precursors, these protective groups and precursors being inert with respect to the glycosylation reaction and with the reactive groups, permitting the positioning, in the course of subsequent operations, of given substituents at the various positions, and this, as the case may be, sequentially, the conditions of application to cause the starting substances to react being selected so as not to alter the structure of the units of these substances and the nature of the various substituents present, provided that the establishment of the interglycoside linkage does not lead to the production of a disaccharide with a [2-N-sulphate or (2-N-acetyl)-6-O-sulphate-D-glucosamine]-[methyl-D-glucuronic acid] structure.

Due to the above arrangements, it is thus possible to form a covalent bond between the units of structure A and U and this, in the stereo-chemistry which this type of enchainment presents in the biologically active molecules already considered.

It is even possible by means of the invention to carry out the desired chain formations in a given order and/or possessing a given stereo-specificity.

The means proposed according to the invention thus enable the establishment particularly of a

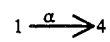

type linkage between a D-glucosamine unit and either D-glucuronic acid, or L-iduronic acid, a

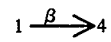

type linkage between a D-glucuronic acid unit and a D-glucosamine unit and a

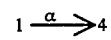

type linkage between an L-iduronic acid unit and a D-glucosamine unit.

The mono- or oligo-saccharidic intermediates of this synthesis are semi-open or open products. A compound will be called semi-open on the right when it is a compound activated or potentially activatable on its anomeric carbon, thus permitting its transfer to the non-reducing end of a monosaccharide or of an oligosaccharide. The expression "compound semi-open on the left" will denote a monosaccharide or an oligosaccharide possessing a single free or potentially free —OH function, enabling its specific glycosylation. By way of illustration, there is indicated below the formula 1 of an example of a compound semi-open on the left and that 2 of an example of a compound semi-open on the right:

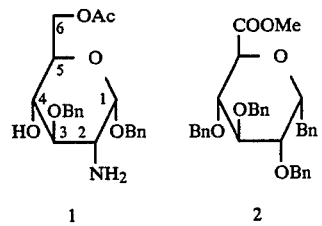

It follows that derivatives will be called open when they relate to a derivative semi-open both on the right and on the left according to the above definition, such derivatives permitting elongation of the chain in both directions. A derivative of this type corresponds for example to formula 3:

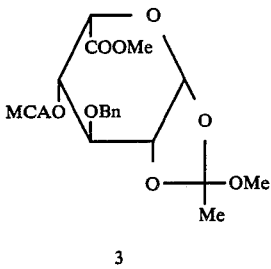

3

As for closed derivatives, they are substances whose units cannot give rise to chain elongation by reason of the nature of their substituents.

According to an additional feature to be able to add units to the A—U or U—A sequence formed in the preceding step, the A and U units of the sequence formed must include temporary protective groups, that is to say groups capable of selectively blocking a position of the A or U unit intended to take part in a novel glycosylation reaction. These groups are removable in the presence of other groups present on the units of the starting products by recreating an alochol, which permits in repeating the preceding step of glycosylation elongation of the glucid skeleton.

The invention hence provides access to the synthesis of oligosaccharides with varied enchainments, whether it relates to α or β stereo-specificity and/or the order of enchainment between the a and c and/or b, units, lengthening being producible as desired.

According to yet another feature of the process of the invention, the developed glucid chain is subject to one or several chamical reactions in order to introduce a given type of functional group or, successively, several types of groups, then to form, if desired, derivatives of these functional groups.

This functionalisation step may be effected by eliminating only certain protective groups and/or certain precursor groups of the amino derivatives or again the whole of the protective groups and/or of the precursor groups and by introducing in their place a given type of substituent or successively different substituents, then by releasing a portion or all of the —OH groups still blocked, if desired.

It is understood then that the various groups present on the units of the chain are compatible with the substituent introduced at each step.

The one or more chemical reactions applied in the course of the functionalisation steps are carried out so as not to alter the structure of the chain and the groups that it is desired if necessary to maintain and/or those which have already been introduced.

According to a preferred embodiment of the invention, to obtain oligosaccharides with specific substitutions as defined above, starting materials are advantageously used containing several types of protective groups, namely (1) one or several semi-permanent groups and (2) one or several permanent groups.

By semi-permanent groups, is meant groups removable in the first place after the reactions of glycosylation when the glucid skeleton includes the number of desired units, without removal or alteration of the other groups present, then enabling the introduction of the desired functional groups at the positions that they occupy.

The permanent groups are groups capable of maintaining the protection of the —OH radicals during the introduction of the functional groups in place of the semi-permanent groups.

These groups are selected from among those compatible with the functional groups introduced after removal of the semi-permanent groups. It concerns, in addition, groups inert with respect to the reactions carried out for the positioning of these functional groups and which are removable without the functional groups being altered.

Advantageously, the practising of these arrangements enables the development of a glucid chain in which the A and U units are selectively substituted.

To prepare more particularly oligosaccharides containing A and/or U units of the biologically active molecules mentioned above, recourse is advantageously had to protective groups such as acyl, alkyl possibly substituted or aryl radicals.

The units of the products employed of type A comprise, at the 2 position, a nitrogen group permitting the maintenance of the presence of a nitrogen function during the operations applied in the process. This nitrogen group is advantageously constituted by groups such as —$N_3$ or —NHCOO—$CH_2$—$C_6H_5$, or any other group constituting a precursor of the amine function or of an amine derivative, in particular —$NHSO_3^-$ or —NH-acyl, more especially —NH—$COCH_3$.

As for the carboxyl functions of the U units, they are blocked by groups inert with respect to reactions used for the replacement of the protective groups and removal at the end of the synthesis to liberate the carboxyl groups, possibly for the purposes of salt formation. These protective groups of carboxyl function are selected advantageously from among alkyl radicals or aryl radicals.

The structure of the product employed in the glycosylation reaction is selected as a function of the units of the glucide skeleton desired as well as of the desired substitutions.

To form, for example, a disaccharide of —U—A— type, two compounds respectively with uronic acid and amino sugar structure, corresponding, in addition to the above-mentioned definitions, are used.

For chain lengthening, these compounds as employed to form the disaccharide concerned, contain, in addition, a temporary group on the position intended to be involved in the new glycosylation reaction. For U—A disaccharide lengthening towards the left, this temporary group is present on the U unit and for lengthening to the right on the A unit.

It is thus possible to obtain, in particular, enchainments $U_wA_xU_yA_z$ in which the sum of the indices is comprised between 2 and 12, these values being included in the range, where w and y cannot be nil simultaneously. Regular enchainments are of the type $U(AU)_n$, $(AU)_nA$, $(UA)_n$ or again $(AU)_n$ with n 1 to 6.

According to a modification of the process of the invention, the alternation of A—U or U—A type encountered in the structures of natural products can be modified by using, in place of the one or several A or U units, a sugar constituting a structural analog of an A or U unit, such as a neutral or a desoxy-sugar, or again other uronic acid units or amino sugars U or A of different configurations.

In a preferred embodiment of the process of the invention, the above alcohol is reacted with a reactive derivative such as a halide, an imidiate or an orthoester. These condensations are carried out under anhydrous conditions.

The condensation reaction between the halide and the alcohol is advantageously of the Koenigs-Knorr type. The halide is advantageously constituted by a bromide or a chloride by reason of the ease of production.

Operations are in a solvent medium, more especially in an organic solvent, particularly of the dichloromethane or dichloroethane type.

Advantageously a catalyst is used, generally a silver or mercury salt, for example, silver trifluoromethane sulphonate, commonly called silver triflate, silver carbonate, silver oxide, mercuric bromide or mercuric cyanide. Also a proton acceptor is used such as sym-collidine in the same way as an extractor for the water possibly present and/or for the halohydric acid formed, for example 4 Å molecular sieves.

Study of the reaction conditions show that it is appropriate to operate at room temperature or again at a lower temperature which can reach 0° C. or less, in an atmosphere of an inert gas such as nitrogen or argon.

These conditions enable the units of structure a and b or c (or the reverse), to be condensed, in the desired stereo-chemistry. They also permit the establishment of covalent bonds with neutral sugars or desoxy-sugars.

A modification comprising the use, as catalyst, of mercuric derivatives, in particular of cyanide and/or or mercuric bromide, is established to be suitable for forming covalent bonds between alcohols of various structures and an L-idose precursor of the unit of c structure (L-iduronic acid). According to this modification, 4 Å molecular sieves are also used. The organic solvent is selected according to the reactivity of the alcohol. Thus advantageously there is used a solvent of the type of nitrobenzene when the condensation requires a temperature higher than 100° C. For lower temperatures, solvents such as benzene or dichloromethane are used. Mixtures of solvents are also suitable to carry out the condensation reaction.

With units of type U, in particular c units, it is advantageous to use, as reagent group an orthoester. The reaction is then preferably carried out at a temperature above 100° C.

The solvent medium is of the chlorobenzene type or any other solvent whose boiling point exceeds 100° C. and it is advantageously between 100° and 150° C. To activate the reaction, a catalyst such as 2,6-dimethyl pyridinium perchlorate is used.

This embodiment of the condensation step is found to be of great interest to form an interglycoside linkage between a unit of structure c (L-iduronic acid) and a unit of structure a (D-glycosamine)

The use of the orthoester group has in particular a double advantage.

On the one hand, it permits conferring on the anomeric carbon of c the necessary reactivity for the glycosylation reaction. On the other hand, the opening of this group ensures the positioning at the 2 position of c of a protective group, selectively removable, thereby permitting the introduction in its place, of a specific substituent group.

Thus, by the reaction of a 1,2-O-methoxyethylidene group of a c unit with the —OH radical of an a unit, it is possible at the same time to establish an interglycoside linkage between the two products used and to have at the 2 position of c an —OAc group (Ac representing an acetyl group) which could be removed selectively for the purposes of introduction of a given functional group, for example —$SO_3^-$. This feature also permits full liberty to be left for treating the 4 position of the c unit.

These features, particularly advantageous, enable the provision of a 2-O-sulphate L-iduronic unit to be made, such as exists, for example, in heparin chains.

When an imidoyl group is used as the reagent group, it is found to be appropriate to operate at low temperature, more especially at a temperature below or equal to about 0° C., in a solvent medium, such as dichloromethane, in the presence of a 4 Å molecular sieve and a catalyst such as boron trifluoride etherate.

In the starting alcohol, the free —OH group occupies the position that it is desired to engage in the glycosylation linkage.

By selecting the alcohol suitably, it is thus possible to form linkages of the 1-2, 1-3, 1-4 or 1-6 type.

From the sequence formed at the end of the condensation reaction, a chain is developed including the desired number of units by repeating the glycosylation step.

The alcohol function of one of the units A or U involved in the glucide sequence already constituted is then advantageously liberated from its temporary protective group. The choice of this group will be easily determined by the technician skilled in the art according to the nature of the other groups present on the glucide chain.

Among the various groups which can be used, is mentioned the allyl group which, by treatment, for example first with an isomerising agent such as Pd, Rh and Ir derivatives, in particular rhodium tris-triphenylphosphine chloride (I), or again potassium tertio-butoxide, then under acid conditions, in particular with a mixture of mercuric oxide and mercuric chloride, enable the recreation easily of an alcohol at the position that it occupies.

In the same way, it is possible to obtain an —OH group by saponification from an —O-acyl group, in particular —O-acetyl or O-chloroacetyl.

These radicals can be removed to liberate an —OH function, for example, by means of thiourea in a solvent medium, advantageously at a temperature higher than 80° C., preferably of the order of 100° C.

The foregoing arrangements enable the production of a glucide chain with alternate A—U or U—A units.

This regular alternation can be modified by applying suitable substances in the glycosylation reaction. It is thus possible to develop an irregular structure with the incorporation of units other than U or A, in particular neutral sugars or again desoxy-sugars. Another type of irregular structure can be obtained by adding several consecutive A units or U units between two A—U or U—A structural units.

It is understood that the various arrangements of the invention relating to the A and U units are applied equally to other units which can include the glucide chain, such as neutral sugars or desoxy-sugars.

As has already been indicated, the various groups present on the A and U units are selected so as to confer on the latter sufficient reactivity to produce the glycoside linkage concerned.

The —OH radical protective groups, apart from the temporary groups already considered, are generally selected from the group comprising acyl radicals (particularly acetyl, alkyl, substituted alkyl, such as benzyl), and for two neighbouring positions, among the acetal groups or Ketals, for example benzylidene. Another form of protection consists of carrying out blocking of two —OH groups in epoxide form or of 1,6-anhydro bridge.

Advantageously, the products used in the glycosylation reaction contain several types of protective groups, which permits in the course of the step of functionalisation the successive introduction of one or several functional groups and the liberation of one or several —OH radicals if desired.

In general, the protective groups may already occupy certain positions on the products applied in the glycosylation reaction.

They may also be introduced from other groups once the glucide skeleton is constituted. This modification comprises, for example, the use for glycosylation of a substance A in which the —OH groups at the 2 and 3 positions and at the 1 and 6 positions are blocked in anhydrous form, respectively 2,3-epoxide and 1,6-anhydro. Due to this blocking, during the development of the glucide skeleton there is available an element constituting potentially an A unit but not interfering with the reactions applied in the synthesis. This arrangement has the advantage of allowing wide liberty to carry out desired reactions on the groups of the other units.

It will be noted, in addition, in the case concerned, that the opening of the epoxide function by the sodium azide enables the introduction, at the 2 position, of an $N_3$ group which hence constitutes a precursor of an amine function.

Preferably, to have available a glucide chain permitting the introduction successively of one or several types of substituents in the course of the functionalisation step, in particular the specific substitutions above, products are applied comprising several types of protective groups, namely the semi-permanent groups and the permanent groups defined above.

As already indicated, the substitutions of the natural products concerned, apart from those of the 2 positions of the A units, are essentially constituted by sulphate groups.

Applicants researches to perfect the suitable sulphation conditions have shown that it is possible and even advantageous to carry out a sulphation reaction in the presence of benzyl groups. Contrary to opinions accepted in this field, the removal of benzyl permanent groups, in the presence of —O-sulphate groups, can be effected.

Preferably, the —OH radicals of the starting materials intended to be sulphated are then protected by acyl groups, in particular acetyl, whilst the —OH radicals intended to be liberated at the end of the synthesis are protected by a permanent group such as the benzyl group.

By the high flexibility of the process of the invention, it is possible to subject all of the glucide chain formed to a given chemical reaction in order to introduce a particular type of substituent.

This treatment can consist, for example, of esterification, particularly sulphation by means of a suitable agent, carried out under conditions not changing the oside structure. This sulphation can be carried specifically or not, as necessary on the fully protected glycoside.

In a preferred embodiment of the invention, the functionalisation step is however effected selectively so as to introduce on the chain, successively, several types of substituent and then certain —OH radicals to be liberated.

By particularly advantageous conditions, enabling the introduction of the sulphate groups on the predetermined positions of the units, to free the —OH radicals at other positions, to form at the 2 position of the A units an amino derivative and in the 6 position U units of the acid derivatives, units corresponding to the following characteristics are applied.

The semi-permanent groups of these units occupy positions intended to be sulphated and are constituted by —O-acetyl groups.

As for the positions corresponding to an —OH group intended to be liberated, they are occupied by semi-permanent groups constituted by benzyl groups.

The 2 positions of the A units are substituted by groups such as $N_3$ or $NH-COO-CH_2-C_6H_5$ and the 6 positions of the U units are occupied by carboxyl groups protected by an alkyl radical, in particular methyl.

This set of conditions enables the realisation of the functionalisation step, for example as follows:

First there is introduced selectively the sulphate groups after having eliminated to —O-acetyl blocking groups. This reaction is carried out so as not to affect the benzyl groups and the nitrogen and carboxyl groups present.

In the respect, advantageously a saponification reaction is carried out by means of a strong base such as soda.

This reaction is carried out preferably at a temperature below ambient temperature and more especially close to 0° C.

The product resulting from the hydrolysis is subjected to the action of an alkylation agent in order to introduce, on the carboxyl group, the protected alkyl groups which are found to be removed on hydrolysis.

By reaction with a sulphation agent, the introduction of sulphate groups at the positions released by hydrolysis and left free after the action of the alkylation agent, is then obtained.

Satisfactory reaction conditions for the sulphation comprise the utilisation of a sulphation agent, such as a trimethylamine/$SO_3^-$ complex. This reaction is advantageously carried out in a solvent medium, more especially in a solvent such as dimethylformamide. Preferably operation is at a temperature higher than room temperature, generally in the vicinity of 50° C., which corresponds to a reaction time of about 12 hours.

After the introduction of the sulphate groups on the alcohol functions, the liberation of the —OH groups blocked by the benzyl radicals follows.

The removal of benzyl groups is advantageously done by catalytic hydrogenation under conditions compatible with the maintenance of the sulphate groups and the conversion of the nitrogenous groups into amino functional groups.

Preferably the operation is carried out under hydrogen pressure in the presence of a catalyst of the Pd/C type.

This reaction is advantageously carried out in an organic solvent medium, in particular alcoholic, supplemented with water.

To obtain hydrogenation of the precursor nitrogenous groups and the removal of the protective radicals from the —OH groups, the reaction is advantageously carried out over a period of about 3 to 4 days.

As already indicated, the amino functional groups are in the form of derivatives of the N-acetyl or N-sulphate type in the biologically active molecules concerned.

To form N-acetyl groups, the product resulting from the hydrogenation reaction is subjected to an acetylation agent. In this respect, acetic anhydride constitutes a particularly suitable agent.

To carry out this selective acetylation reaction without affecting the other substituents present on the units, it is appropriate, in particular, to operate at a basic pH, in particular close to 8 in an aqueous medium.

It may also be desired to form N-sulphate groups which may be done by means of a sulphation agent of the above-indicated type. pHs higher than 9, advantageously of the order to 9-10, are used for the sulphation.

After the sulphation reaction, the addition of a strong base enables the liberation of the carboxyl groups.

The products formed may easily be salted by exchange resins with an appropriate cation. In natural products, the cation in particular is constituted by sodium. Hence exchange resins with sodium cations are advantageously used.

It is also possible to form salts of potassium, lithium, magnesium, calcium. A proton exchange resin is then used, and then the acid formed is neutralised with the base of the cation.

The invention is also directed to oligosaccharides constituting intermediates in the various steps of the process of synthesis defined above.

In one family, these oligosaccharides include at least one binary A—U and U—A unit completely protected and possessing either a reactive group on the anomeric carbon of the unit at the reducing end, or a single free —OH group on the unit at the non-reducing end, this —OH group occupying the 3, 4 or 6 position in the case of an A unit and the 2, 3 or 4 position in the case of U units.

In another family, the oligosaccharides are constituted by completely protected units such as obtained at the end of the glycosylation step. Another family again comprises products in which one or several —OH groups are liberated.

These various oligosaccharides comprise a chain based on binary units of structure (A—U)$_n$ or (U—A)$_n$ in which n is a number from 1 to 6.

These oligosaccharides correspond to an enchainment of the type a-b or a-c.

In one group of intermediate oligosaccharides of the invention, the glycoside chain is constituted by a single type of these binary enchainments.

In another group, several of these types are present.

Corresponding oligosaccharides include in their chains a-b and a-c.

It is understood that the order of the enchainments concerned above in one or several of the binary units, can be reversed according to the invention.

According to one modification, the intermediate oligosaccharides defined above contain one or several consecutive a or b or again c units.

According to another modification, the intermediate oligosaccharides contain one or several units of neutral sugars and/or several desoxy-sugars in their structure. The various protective groups of these sugars correspond to the definitions given above or the A and U units.

In these oligosaccharides, the constituent units are connected to one another by linkages of 1-2, 1-3, 1-4, or 1-6 type according to the nature of the alcohol utilised in the glycosylation step.

The oligosaccharides possessing the structure of heparin or heparine-sulphate fragments include c

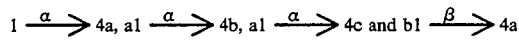

linkages.

One group of preferred oligosaccharides contains at least one binary unit possessing a structure of the type b

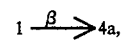

that is to say [D-glucuronic acid]

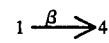

[D-glucosamine] corresponding to formula I:

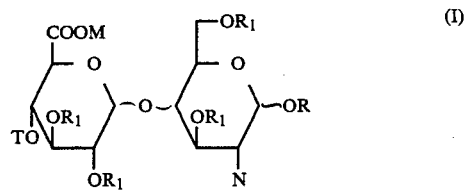

in which:
- the R$_1$ radicals, identical or different from one another, if necessary conjointly with R, represent a protective group, in particular a sp semi-permanent group or a p permanent group,
- T, a temporary group t, or a permanent group p, or a hydrogen atom,
- N, is a nitrogenous group amine or amine derivative precursor.
- R, an aliphatic or aromatic radical, particularly an alkyl radical comprising from 1 to 4 carbon atoms, where OR represents a reactive group such as a halide or again R an alkyl radical and
- M, a group blocking the acid function, these various symbols having the above-given meanings.

In a sub-group, all the radicals R, R$_1$ and T are identical and represent a p or sp group.

In another sub-group, the radicals R$_1$ are different from one another, one at least representing a sp type group, possibly conjointly with R, the one or more other radicals R$_1$ representing a p group.

It will be noted that the general meanings of the symbols of formula I are applied also to the formulae of the various groups considered below. In the same way, there is to be found again in each of these groups, particularly, the two sub-groups mentioned above.

Preferred oligosaccharides correspond to the formulae (II), (III), or (IV):

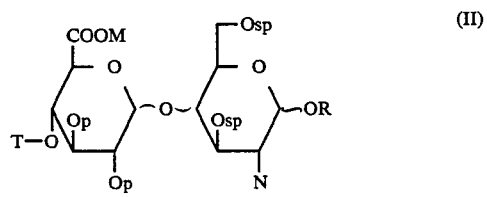

-continued (III)

(IV)

in which the various symbols have the above-indicated meanings.

Preferably, in the formulae (II) to (IV), the symbols given have independently, or in combination, the following meanings:

M represents a hydrogen atom or an alkyl radical, particularly methyl, sp an acyl group, in particular acetyl, p, a substituted alkyl group, in particular benzyl, R, an acyl group at α or β, in particular an acetyl group, an alkyl radical, in particular methyl or substituted alkyl, particularly benzyl, or —OR a halogen, in particular a bromide, or again an imidoyl radical, N, an azide group, T, the group t representing an acyl radical, in particular acetyl, a halogenated acyl radical, in particular, a monochloro or trichloroacetyl radical, or the group p representing a substituted alkyl radical in particular the benzyl radical, as the case may be itself paramethoxy or again a hydrogen atom.

Another preferred group of oligosaccharides includes at least one unit of the type c1→4b, that is to say [D-glucosamine]1→4[D-glucuronic acid] corresponding to formula (V):

(V)

Preferred oligosaccharides correspond to the following formulae (VI) or (VII):

(VI)

-continued (VII)

In these formulae (VI and VII), symbols M, N, sp, p have, preferably, the particular meanings given above with respect to the formulae (II) to (IV), and R represents, in addition, preferably, a propenyl, allyl, imidoyl, or —H group, with N representing then more especially a —HN-acetyl group.

It will be recalled that the order of chain formation of the units may be reversed.

In another preferred group, the oligosaccharides contain at least one binary unit of type c $$1 \xrightarrow{\alpha} 4a,$$

that is to say [L-iduronic acid]

$$1 \xrightarrow{\alpha} 4$$

[D-glucosamine], corresponding to the formula (VIII):

(VIII)

Preferred oligosaccharides correspond to the following formulae (IX and X):

(IX)

(X)

In preferred manner, the symbols figuring in theses formulae (IX) and (X) have the following meanings:

the various sp and p groups may be identical and represent an acyl radical, in particular acetyl, or different, as selected from among acyl radicals, in particular acetyl or benzoyl and aryl or substituted alkyl radicals, N represents a precursor nitrogen group, possibly different from that present in compounds of formulae (I) to (V), in particular a NHCOO-(substituted alkyl group), particularly a —NH—COO—CH$_2$—C$_6$H$_5$ group, which permits subjecting the nitrogenous groups to different treatments and to form different amino derivatives at 2 position of the A units, T represents the acetyl, halogenated acyl radical, in particular, monochloro or trichloroacetyl, p-methoxybenzoyl, the symbols p, M and R having advantageously the preferred meanings given above in respect to the formulae (II) to (IV).

Another type of binary unit of preferred oligosaccharides has a

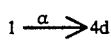

structure, that is to say [D-glucosamine],

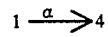

[L-iduronic acid]
corresponding to the following formula (XI):

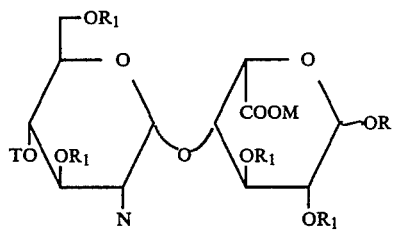

(XI)

Particular oligosaccharides correspond to the formulae (XII) and (XIII):

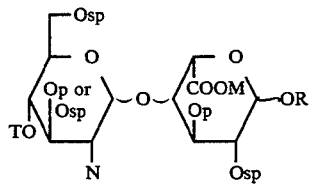

(XII)

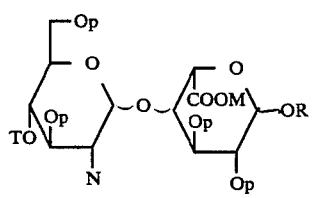

(XIII)

in which the preferred meanings correspond to those give above for formulae (II) to (IV).

Another preferred family of intermediate oligosaccharides entering into the scope of the invention corresponds to the products from which the protective groups have been partially removed in the course of synthesis. In particular, such products include an —OH group in place of the sp groups.

Preferred intermediate products correspond to oligosaccharides having the structure of the complete octasaccharide (ABCDEFGH) or hexasaccharide (C'DEFGH) sequence mentioned above.

Preferably, they are disaccharides AB, BC, CD, etc . . . trisaccharides ABC, BCD . . . , tetrasaccharides ABCD, BCDE . . . , pentasaccharides, ABCDE . . . , hexasaccharides, ABCDEF . . . heptasaccharides ABCDEFG or BCDEFGH or the octasaccharide itself.

Among these oligosaccharides, may be mentioned the structures, BC, DE, DEF, EF, GH, FGH, EFG, EFGH, DEFGH and CDEFGH.

Preferred intermediates disaccharides correspond to the binary units of formulae (I) to (XIII).

A preferred group of intermediate trisaccharides has a structure DEF and correspond to one of the formulae XVIII to XXI.

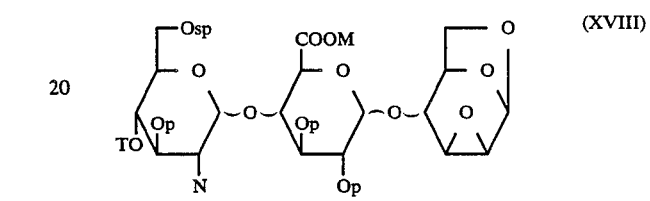

(XVIII)

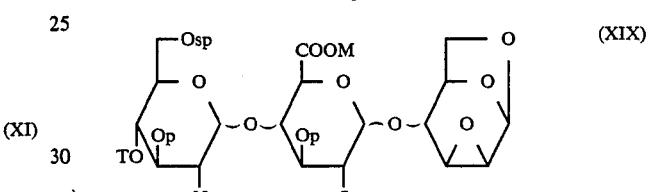

(XIX)

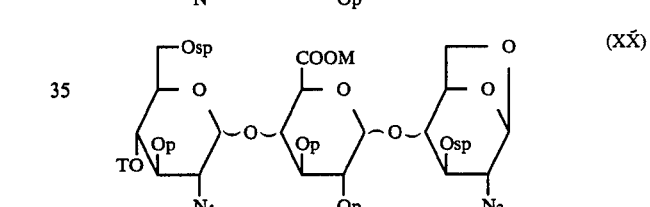

(XX)

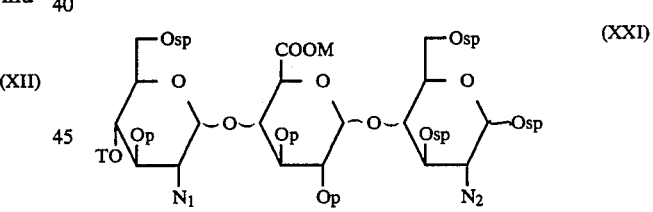

(XXI)

Preferably, N$_1$ and N$_2$, identical or different from one another, represent an azide or —NH—acyl group in particular —NH—acetyl.

Other preferred trisaccharides possess a structure of the type FHG of formula

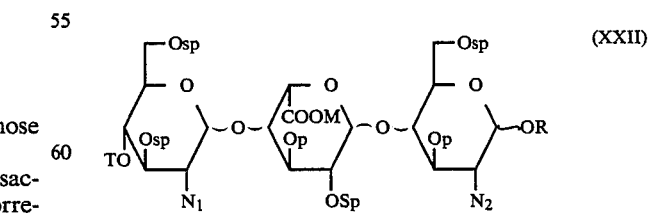

(XXII)

in which the various symbols have the above-given meanings, the two substituents N$_1$ and N$_2$ of the two glucosamine units of structure F and H being identical or again advantageously different, as in the case of natural products, and selected from among the azide or —NH—COO—acyl group, in particular —NH—COO—acetyl or —NH—COO—CH$_2$—C$_6$H$_5$.

Other preferred intermediate oligosaccharides are constituted by tetrasaccharides. More especially advantageous tetrasaccharides possess the structure EFGH and correspond to the following formula

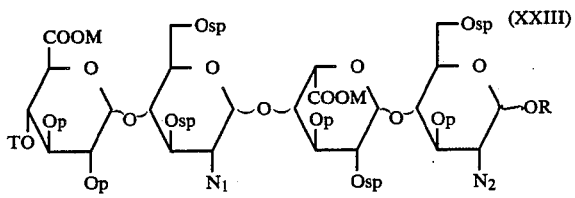

in which the preferred meanings of the different symbols correspond to those indicated for formula XXII.

Another family of intermediate oligosaccharides is constituted by pentasaccharides, in particular, by those of structure DEFGH of formula

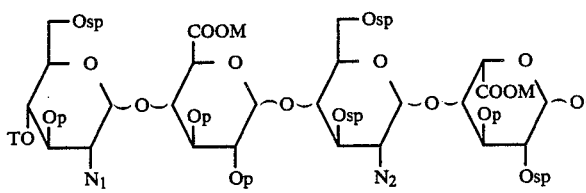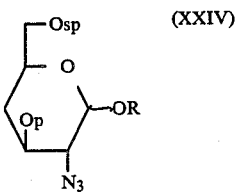

in which the various symbols have the above-preferred meanings, and N$_1$, N$_2$, N$_3$ can be identical or different from one another selected from among the meanings already given.

As mentioned above for binary units, the invention relates also to the above oligosaccharides in which one, several or, as the case may be, all of the —OH groups are liberated in the course of synthesis.

The invention is aimed, in addition, as novel products, at the oligosaccharides corresponding respectively to the various definitions given above, but including one or several functional groups, with the exclusion of the disaccharide [2-N-sulphate (or 2-N-acetyl-6-O-sulphate-D-glucosamine]-methyl-D-glucuronic acid.

These functional groups are constituted preferably, by esters, and occur more especially in the form of inorganic anions.

Particularly preferred esters, by reason of their presence in biologically active molecules of the type of heparin or heparane-sulphate are constituted by sulphate esters.

Other advantageous esters correspond to phosphate esters.

These functional groups are borne by one or several primary alcohols and/or secondary alcohol and/or primary amine functions.

A preferred family of oligosaccharides of the invention thus includes a unit comprising such an anion as defined above at the 6 and/or 3 position.

A particularly preferred family contains an a unit comprising an ester, in particular a sulphate group, at the 6 position and at the 3 position.

Oligosaccharides of this family contain, at the 2 position of a, a primary amine functional group advantageously substituted by a sulphate or by another substituent group.

In the oligosaccharides of the invention containing at least two units a, the amine functional groups at the 2 position may be substituted by the same group or by different groups.

A preferred group of oligosaccharides of the family concerned includes units a comprising sulphate groups on the secondary alcohol and especially the primary alcohol function.

Preferred oligosaccharides of this group comprise at the 2 position of these units an —NHSO$_3$-group. Other oligosaccharides include an —NH-acyl group, in particular —NH-acetyl.

Preferably, the esters below occur in the form of salt with an inorganic or organic cation, in particular a metal cation, particularly an alkali cation, or again a cation derived from a nitrogenous organic base, for example triethylammonium.

The cations used are constituted by sodium. Other cations are suitable such as the potassium, magnesium or calcium cations.

In another preferred family of oligosaccharides of the invention, the carboxyl groups of units b or c are free or are preferably in the form of salt with an organic or inorganic cation such as defined above. They may also be protected as reported above.

Preferred products contain units c comprising a sulphate group at the 2 position.

Other preferred products have sulphates on the b unit.

In these various families of oligosaccharides, the hydroxyl functions of the pyran n rings are either free, or protected by permanent groups of the alkyl type, in particular by methyl groups.

Preferred products of these various families contain, in combination, the units A and U corresponding to the above characteristics.

Taking into account their presence in the biologically active molecules above and particularly in the octasaccharide ABCDEFGH or the hexasaccharide CDEFGH, the preferred oligosaccharides correspond to the products of formulae (I) to (XIII) and (XVIII) to (XXIV) above, but in which the —sp groups are replaced by anions. Preferred products correspond to salts of the above-defined products.

Other preferred oligosaccharides include in addition to the place of the N groups of the a units, an NH—acyl group, in particular —NHCOCH$_3$, —NHSO$_3^-$.

Preferred disaccharides of this type have a structure of the type BD, DE, EF or GH and correspond respectively to the following formulae (XXV to (XXVIII):

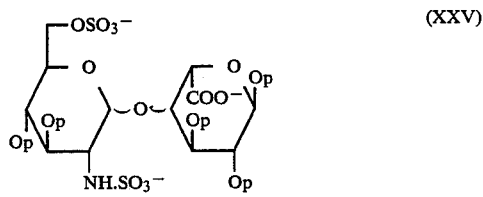

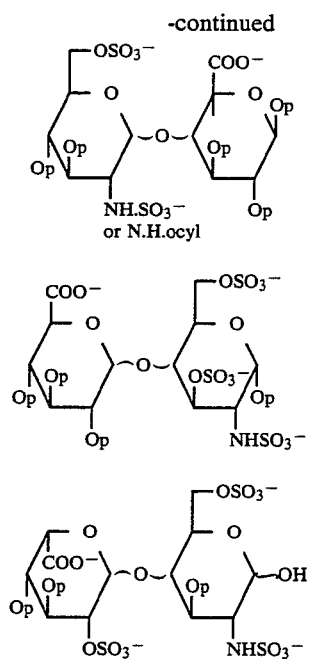

(XXVI)

(XXVII)

(XXVIII)

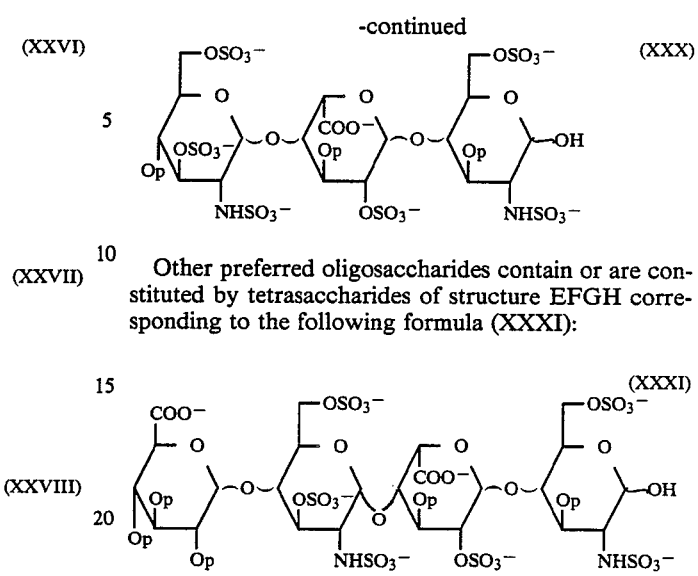

Other preferred oligosaccharides contain or are constituted by tetrasaccharides of structure EFGH corresponding to the following formula (XXXI):

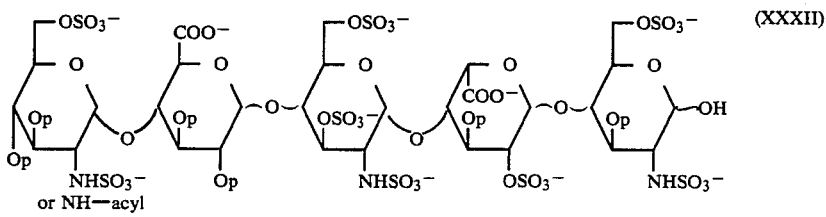

Other oligosaccharides also specially preferred contain or are constituted by pentasaccharides of the following formula (XXXII):

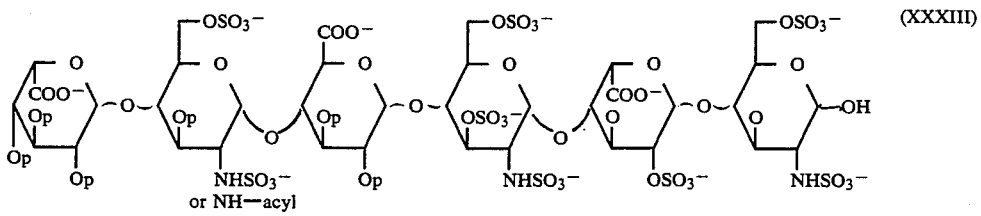

Other preferred oligosaccharides of the invention contain or are constituted by an enchainment of the structure DEF or FGH respectively of the following formulae (XXIX) and (XXX):

Oligosaccharides of the invention which are particularly preferred comprise or are constituted by hexasaccharides of the structure CDEFGH corresponding to the following formula (XXXIII):

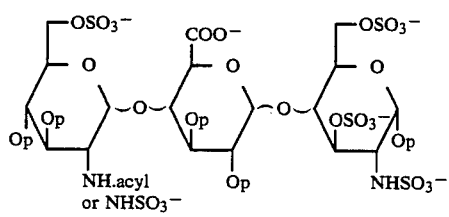

(XXIX)

Other oligosaccharides correspond to one of the formulae (XXV to (XXXIII) above, but contain free —OH groups in place of the —Op groups. These products are then completely deprotected.

In other oligosaccharides again a portion of the —OSO₃⁻ groups may be replaced by —OH groups.

Preferably, the oligosaccharides of the invention include salts, possibly double salts, of the above anions with the already defined cations. Due to their structure, the products of the invention constitute synthesis intermediates of great interest enabling the production of given fragments, or derivatives of fragments, of biologically active molecules.

They constitute, particularly, reference compounds for structure studies.

Pharmacological study of the oligosaccharides of the invention has shown in certain of these compounds biological activities enabling them to control specifically certain steps in blood coagulation. Interesting products are constituted, for example, by trisaccharides of formula (XXIX), sulphated and deprotected and more particularly the derivatives of Example 13bis.

In a remarkable way, the pentasaccharides of formula (XXXIII) sulphated and deprotected and very especially the derivative 50 show themselves to be endowered particularly with high affinity for AT III and very high selective inhibition activity of the activated X factor or Xa factor of the blood.

The invention therefore relates also to their use in the constitution of biological reagents, useful in laboratory, particularly as comparison elements for the study of other substances of which it is desired to test the anticoagulant activity, particularly at the level of the inhibition of the Xa factor and of the determination of antithrombin III.

The trisaccharide of formula (XXIX) with the structure DEF in which the D unit includes an N-sulphate group has, for example, an anti-Xa activity measured by the Yin-Wessler test, of the order of 7 u/mg.

The pentasaccharide 50 of Example 9 is characterised by distinctly higher Yin-Wessler titres than those of heparin.

More especially, this pentasaccharide is endowe with an anti-Xa activity (Yin-Wessler) equal to or greater than 2000 u/mg and a high affinity for AT III.

In a test using a chromogen substrate, this activity has even been 4000 anti-Xa units/mg (method of Teien A.M. and Lie modified; Thrombosis Research No. 10, 1977, 388–410).

This test consists of using the Xa factor marketed by the Sigma company in solution at 8 u/ml in physiological serum, the concentration of the substrate being 1.33 mM.

To carry out this test it is possible to proceed as follows.

10 μl of solution to be determined and 300 μl of human plasma diluted with Tris maleate buffer 0.02M, pH 5 are mixed.

It is left to incubate one minute at 37° C.

100 μl of the above-said Xa factor (8 u/ml) are added and one minute later, the solution obtained is injected into the substrate.

The overall anticoagulant activity of this product is very low, 4 u/mg in the APTT test.

These properties enable them to check specifically, certain steps in blood coagulation.

The study of these products shows that they are capable of exerting a powerful antithrombotic activity. In addition, derivatives according to the invention have great interest for combatting disorders of the vascular wall, (atheroscleroses and arterioscleroses).

In addition, they have the advantage of not having the effect of activation on platelet aggregation and not resulting in thrombocytopenia. They have also the advantage of being practically devoid of effect on bleeding time, which eliminates the risks of hemorrhage. These two properties are extremely important for medical uses.

In addition, there is observed particularly by the subcutaneous route a prolonged pharmacokinetic reaction which procures also a considerable interest in the product.

The oligosaccharides of the invention are, in addition, advantageously devoid of toxicity.

These products are hence particularly valuable for developing useful medicaments, particularly for the prevention and treatment of thomboses.

The invention hence relates also to pharmaceutical preparations which contain said oligosaccharides with high anti-Xa activity, more especially the pentasaccharides considered above.

It relates also particularly to pharmaceutical preparations devoid of pyrogenic substances containing an effective amount of active principles in association with pharmaceutical excipients.

It also relates to the compositions in which the pharmaceutical vehicle is suited for administration orally. Suitable administrative forms of the invention for oral administration may advantageously be gastroresistant capsules, pellets or tablets, pills, or again presented in liposome form.

Other pharmaceutical compositions comprise these oligosaccharides in association with suitable excipients for rectal administration. Corresponding administrative forms are constituted by suppositories.

Other administrative forms of the invention are constituted by aerosols or pommades.

The invention relates also to sterile or sterilizable injectable pharmaceutical compositions for administration both intravenously and intramuscularly or subcutaneously.

These solutions contain advantageously 1000 to 100 000 u (Yin-Xessler)/ml of oligosaccharides, preferably from 5000 to 50 000, for example from 25 000 u/ml, when these solutions are intended for subcutaneous injection. They may containm for example from 500 to 10 000 particularly 5000 u/ml of oligosaccharides when they are intended for injection intravenously or by perfusion.

Advantageously, such pharmaceutical preparations are presented in the form of ready-for-use discardable syringes.

The invention relates also to the pharmaceutical compositions containing said oligosaccharides in association with another active principle, useful in particular for prophylaxis and treatment of thrombosis, such as a veinotonic agent like dihydroergotamine, nicotinic acid salt or a thrombolytic agent like urokinase.

The pharmaceutical compositions of the invention are particularly adapted for the control (preventive or curative) of certain stages of blood coagulation in man or in the animal, particularly in the case where the patient is subject to risks of hypercoagulability resulting particularly from surgical operations, from atheromatous processes, from the development of tumors and disorders of blood clotting by bacterial or enzymatic activators etc.

In order to illustrate the invention, there is indicated, below, an example of the posology usable in man: this posology comprises, for example, the administration to the patient of 1000 to 25 000 u (Yin and Xessler) subcutaneously, once to thrice daily, according to the level of the risks of hypercoagulability or the thrombotic condition of the patient, or from 1000 to 25 000 u/24 hours, intravenously, in discontinuous administration at regular intervals, or continuous by perfusion, or again from 1000 to 25 000 u (three times weekly) intramuscularly or subcutaneously (these titers being expressed in Yin-Xessler units). These doses can naturally be adjusted for each patient according to results and blood analyses carried out previously, the nature of the disorders from which he suffers and, generally, his state of health.

Besides the pharmaceutical compositions containing the oligosaccharides as such, the invention is aimed also at pharmaceutical compositions containing at least one oligosaccharide as defined above, conjugated, by a covalent bond, to a soluble support or an insoluble support, advantageously by means of the reducing terminal sugar.

Conjugates fixed to preferred soluble supports are constituted by oligosaccharides conjugated with At III.

A conjugate of this type including the pentasaccharide 49 is very especially preferred. Such products constitute particularly interesting medicaments in the prevention of thromboses, in the case of deficiencies of AT III.

Other preferred conjugates with soluble supports are formed from an oligosaccharide fixed to a vehicle such as a protein, particularly polylsine, or bovin albumin serum.

These products are useful as immunogens themselves sources of circulating antibodies produced in vivo or of monoclonal antibodies cloned in vitro by suitable techniques.

In other preferred conjugates the oligosaccharides of the invention are conjugated to insolute supports. Advantageously conventional supports are utilized.

These conjugates are useful as immunoabsorbents, for example for purification of high specificity of At III and for its estimation or for the development by fixing to biocompatible polymers, of novel athromobotic hemocompatible polymers.

The invention is directed also to the use of the oligosaccharides concerned in nuclear medicine, as radiopharmaceutical products. These products are then labelled by tracers selected from among those currently used in this field, and particularly by means of technetium 99 m.

To this end, the technetium 99 m obtained from commercial generators is converted, in the form of sodium pertechnetate of unreactive valency 7, into technetium reduced to valency 4 which would be the most reactive form of technetium. This conversion is carried out by means of a reducing system produced from certain tin salts (stannous chloride), iron salts (ferrous sulfate), and titanium salts (titanium trichloride) or other salts.

Most of the time, this simple reduction of the technetium suffices, under given pH conditions, to effect the fixing of the technetium to the molecule concerned.

It is possible to use the products of the invention which constitute in a way a support, at doses of the order of 100 to 200 u Yin-Wessler.

For the development of these radiopharmaceutical reagents, it is possible to operate in accordance with the method of the P.V. Kulkarni et al. in The Journal of Nuclear Medecine 21, No. 2, p. 117-121.

The so-marked products are advantageously used in in vivo tests for the detection and extended diagnosis of thromboses and of thrombotic states.

The oligosaccharides of the invention may also be used for the determination of the specificity of numerous enzymes involved in the metabolism of the glycosaminoglucuronoglycans.

Other advantageous characteristics of the invention will appear from the examples which follow and with reference to FIGS. 1 to 32 illustrating the products employed in the syntheses described.

In these Figures, the numerical references of the formulae are used also in the Examples to denote the same products.

The abbreviations used in these formulae have the following meanings: Ac: an acetyl group; Me: methyl; Bn: benzyl; Bz: benzoyl; MCAO: monochloroacetyl; Tr: trityl; but.: butyl and S an $SO_3^-$ group.

EXAMPLE 1

Synthesis of the derivative 13 namely methyl (prop-1'-enyl 2.3-di-O-benzyl-α-D-glucopyranoside)uronate of the formula

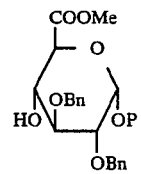

The synthesis is carried out from glucose by the following steps (a) to (m):
(a) preparation of the allyl derivative;
(b) blocking of the 4 and 6 positions of the allyl derivative by a benzylidene group;
(c) introduction of benzyl groups at 2 and 3 positions;
(d) unblocking of the 4 and 6 positions by removal of the benzylidene group;
(e) introduction of a trityl group at the 6 position, followed by an acetylation reaction of the 4 position;
(f) removal of the trityl group at the 6 position;
(g) oxidation of the primary alcohol group at the 6 position;
(h) methylation of the carboxyl group at the 6 position;
(i) introduction of the propenyl group at the 1 position;
(j) removal of the acetyl group at the 4 position.

These steps are carried out as follows (see FIGS. 1 and 2):

(a) Preparation of allylα-D-glucopyranoside (compound 1):

A solution of gaseous hydrochloric acid (18 g) in allyl alcohol (600 ml) is heated to 70° C. Then anhydrous glucose (300 g) is added and it is kept at this temperature for 3 hours.

The reaction may be followed by thin layer chromatography (t.l.c.) in the solvent methanol/chloroform (¼ v/v). The brown solution obtained after 3 hours is concentrated to dryness, under vacuum, neutralized with a concentrated ammoniac solution (50 ml) then concentrated again to dryness. To the residue obtained, acetone (500 ml) is added, it is brought to boiling and kept there until complete solution. After cooling, the liquid is decanted. The residue is again subjected to the same treatment until the t.l.c. analysis of the extract shows exhausting of the residue in derivative 1 or indeed a very high contamination of the extract with impurities.

A portion of the first fraction extracted (12 g) is chromatographed on silicate. The derivative 1 which can be crystallized in an acetone/ether mixture (6.5 g; m.p. 95°-99° C.) is recovered. The rest of the product may be purified by the same process.

(b) Blocking of the 4 and 6 positions of the allyl derivative leading to 4.6-O-benzylidene-α-D-glucopyranoside (compound 2)

Compound 1 (37 g) is dissolved in dimethylformamide (200 ml). Dimethoxytoluene (41 g) is then added followed by hydrated paratoluene sulfonic acid (130 mg).

After 2 hours heating (water-bath) under vacuum and reflux, the reaction is terminated (t.l.c. methanol/chloroform 2/25 v/v). The solvent is evaporated. The syrup is dissolved in methanol (the minimum), this solution is poured drop by drop into an aqueous sodium bicarbonate solution (6.3 g in 320 ml water). The precipitate obtained is recrystallized in ethanol (21 g; 120°–121° C.). The mother-liquors also yield product 2. Total yield (37 g; 71.4%).

(c) Introduction of the benzyl group leading to allyl 2.3-di-O-benzyl-4.6-O-benzylidene-α-D-glucopyranoside (compound 3)

Compound 2 (45 g) is dissolved in anhydrous DMF (500 ml). Sodium hydride (28 g of a 50% dispersion in oil) is added.

After 30 minutes, the mixture is cooled to 0° C. and then, drop by drop, benzyl bromide (52 ml) is added. The reaction is followed by t.l.c. (ether/hexane, 1/1, v/v). Then slowly methanol (150 ml) is added, evaporated to dryness and taken up again with chloroform. The chloroform phase is washed with water, dried over sodium sulfate. After evaporation of the solvent, the residue is crystallized in an ether/hexane mixture (36.5 g MP 83°–84° C.).

This product is slightly contaminated with an impurity migrating higher in t.l.c. (ether/hexane: 1/1; v/v).

(d) Removal of the benzylidene group leading to allyl 2.3-di-O-benzyl-α-D-glucopyranoside-(compound 4)

To a solution of compound 3 (56 g) in methanol (1 l.) is added water (450 ml) and then hydrated paratoluene sulfonic acid (17 g).

After 2 hours at 80° C., the mixture is allowed to cool, the solvent is evaporated and residue is taken up again with chloroform (1 l.). The chloroform solution is washed with water until pH neutral, then dried over sodium sulfate. In this way a pale yellow syrup is obtained (48 g) which is engaged in the following step (synthesis of compound 5).

(e) Introduction of a trityl group at the 6 position followed by an acetylation reaction of the 4 position leading successively to allyl 2.3-di-O-benzyl-6-O-trityl-α-D-glucopyranoside (compound 5) and its 4-O-acetylated analog (compound 6a)

The derivative 4 obtained (48 g) is dissolved in pyridine (250 ml) and trityl chloride (38.5 g) is added. After one hour at 100° C., the reaction is terminated (t.l.c. ether/hexane, 1/1, v/v). To the preceding solution, is added acetic anhydride (200 ml). After one night, the reaction is complete (t.l.c. ether/hexane), ½, v/v). It is evaporated to dryness, the residue taken up again with chloroform (500 ml), the chloroform phase is washed with a 10% acid potassium sulfate solution with water and dried over sodium sulfate.

The chloroform is evaporated. In this way compound 6a is obtained which is engaged as such in the reaction for the preparation of compound 7a.

(f) Removal of the trityl group leading to allyl 4-O-acetyl-2,3-di-O-benzyl-α-D-glucopyranoside (compound 7a)

The derivative 6a obtained is dissolved in chloroform (500 ml). To this solution, cooled to 0° C., is added, drop by drop, under stirring, a solution of boron trifluoride in methanol (20%, 120 ml). The reaction is followed by t.l.c. (toluene/acetone, 10/2, v/v).

The reaction mixture is decanted in a separating funnel. The chloroform phase is washed with water (twice 100 ml) with a saturated solution of sodium bicarbonate, and then with water until pH neutral. After drying, and evaporation, the residue obtained is introduced onto a silical gel column (500 g) equilibrated in toluene. After dilution of the majority of the impurities with pure toluene, the product is eluted with a toluene/acetone mixture (10/2, v/v). In this way 49 g. of compound 7a is obtained which will be engaged directly in the synthesis of the compound 8a.

A portion of compound 7a was obtained pure: $[\alpha]_D^{20} = +11°$ (chloroform). Its IR and NMR spectra, just as elementary analysis, confirm the structure.

(g) Oxidation of the primary alcohol group at the 6 position leading to (allyl-4 O-acetyl-2,3-di-O-benzyl-α-D-glucopyranoside) uronic acid (compound 8a)

A solution of compound 7a (48 g) in acetone (800 ml) is cooled to −5° C. Then, drop by drop, a solution of chromium trioxide (30 g) in sulfuric acid (3.5M; 125 ml) is added. The mixture is allowed to come back to room temperature. Reaction is checked by t.l.c. (methanol/chloroform, 1/10, v/v). At the end of reaction, the reaction mixture is poured into water (500 ml). The product is extracted with chloroform (3 times 250 ml). The chloroform phase is washed with water until pH neutral, dried over sodium sulphate and concentrated to dryness.

The syrup obtained (83 g) is used as such for the preparation of the compound 9a.

(h) Methylation of the carboxyl group at 6 position leading to methyl (allyl-4-O-acetyl-2,3-di-O-benzyl-α-D-glucopyranoside)uronate (compound 9a)

The syrup obtained in the step of preparing compound 8a is dissolved in ether (300 ml). An ether solution of diazomethane is then added until disappearance of the compound 8a (t.l.c. ether/hexane, 1/1, v/v). After acidification with acetic acid, the solvents are evaporated.

The residue obtained (53 g) is dissolved in hot ethanol. The derivative 9a is crystallized on cooling. After recrystallization, this pure compound 9a is obtained (18,4 g)-mp 85°–86° C. $[\alpha]_D^{20} = +12°$ (1.2 chloroform).

This product is characterized by its IR, NMR spectra and by its elementary analysis.

From the crystallization filtrate, a further 7.6 g of compound 9a is obtained.

The overall yield of 9a from the compound 2 is 38%.

(i) Introduction of the propenyl group at the 1 position leading to methyl (prop-1'-enyl 4-O-acetyl, 2,3-di-O-benzyl-α-D-glucopyranoside)uronate (compound 10a)

The derivative 9a (4 g) is dissolved in a mixture of ethanol (119 ml) benzene (51 ml) and water (17 ml). Then diazabicyclo octane (170 mg) is added and it is brought to reflux. To the boiling solution is added tris (triphenylphosphine)-rhodium (I) (500 mg) chloride. The boiling is maintained for 4 hours (t.l.c., ether/hexane, 1/1, v/v).

At the end of the reaction, the solution is filtered and the solvents are removed. Residue is chromatographed on silica gel (150 g) in an ethyl acetate/chloroform mixture (1.50, v/v). Compound 10a is obtained (3.25 g; 81%) which crystallizes in ethanol $[\alpha]_D^{20} = +12°$. (1, chloroform). MP 90° C. The structure is confirmed by elementary analysis and the NMR and IR spectra.

(j) The removal of the acetyl group at 4 position leading to methyl (prop-1'-enyl-2,3-di-O-benzyl-α-D-glucopyranoside)uronate (compound 13)

The derivative 10a (350 mg) is dissolved in methanol (5 ml). Sodium methanolate (0.2 ml, 2M) is added. After 1 hour at room temperature, the reaction is stopped by addition of dowex resin 50-H+. After filtration, product 13 is obtained, contaminated by little product resulting from the α-β elimination.

According to a modification of step e) instead of carrying out an acetylation reaction, a benzoylation reaction is carried out, which leads to: allyl-4-O-benzoyl, 2.3-di-O-benzyl-4-O-benzoyl, 6-O-trityl-α-D-glucopyranoside (compound 6b) from which the trityl group is then removed, which enables allyl-4-O-benzyl-2,3-di-O-benzyl-α-D-glucopyranoside (compound 7b) to be obtained.

These reactions are carried out as follows:
Preparation of compounds 6b and 7b.

To the pyridine solution of the compound 5 is then added benzoyl chloride (1.5 equivalents) and the reaction is followed by t.l.c. (ethyl acetate/benzene, 1/20, v/v). The excess of benzoyl chloride is destroyed by the addition of an excess of methanol. After evaporation to dryness, the residue, taken up again with chloroform, is washed with a 10% KHSO$_4$ solution, with water, dried and concentrated to dryness. The syrup obtained is engaged as such in the synthesis of the compound 7b. This syrup (105 g, obtained from 30 g of compound 3) is dissolved in chloroform (300 ml). Paratoluene sulfonic acid (76 g of monohydrate in 100 of methanol) is added. After one night, the reaction is terminated (t.l.c., ethyl acetate/chloroform, 1/20, v/v). The chloroform phase is washed with water until pH neutral, dried and concentrated to dryness. The syrup obtained (98 g) is chromatographed on a silicate gel column (1.2 kg), eluted with chloroform (0.6 l) then with an ethyl acetate/chloroform mixture (1/20, v/v). Thus a pure derivative 7b (30 g) is obtained which is engaged as such in the step of preparation of compound 8b. From compound 7b, it is possible to oxidize the —CH$_2$OH group at the 6 position and then to introduce a methyl group on the carboxyl group obtained, by forming successively (allyl-O-benzoyl-2,3-di-O-benzyl-α-D-glycopyranoside)uronic acid (compound 8b) and the corresponding methylester (compound 9b).

These derivatives are prepared by proceeding as follows:

Preparation of the compound 8b and of the ester 9b

Compound 7b (27 g) is treated as described for 7a in the preparation of 8a. The syrup obtained at the end of the treatment contains compound 8b which is methylated with diazomethane as described for the compound 8a.

The residue obtained at the end of methylation is purified on silica gel (200 g; ether 1/hexane 1). In this way the compound 9b is obtained (21 g; 77.5%). Its IR and NMR spectra confirm its structure.

From compound 9b, the corresponding propenyl derivative 10b is prepared, by operating as for 10a.

The derivative 13 is then obtained from 10b as by the reaction given for 10a.

According to another modification, (allyl 2.3-di-O-benzyl-α-D-glucopyranoside)uronic acid and methyl(2.3-di-O-benzyl-α-D-glucopyranoside)uronate (compounds 11 and 12). are prepared.

Compound 8b (1.9 g) is dissolved in methanol (40 ml). Then, 5N soda is added in a sufficient amount to have a concentration of 1M of soda. The reaction is followed by t.l.c. (methanol/chloroform, 1/4, v/v). When it is ended, water (100 ml) is added. It is washed with ether, acifidied and the product extracted with ether. The acid ether phase is washed with water until pH neutral. The derivative 11 is not isolated. It is methylated with an ether solution of diazomethane, thus giving the compound 12 (900 mg; 56%) which is then purified on a silicate gel column (ether/hexane 1/1, v/v) [α]$_D^{20}$=+35.2° (1.3 chloroform). Its IR and NMR spectra and its elementary analysis confirm its structure. In the same manner, the derivative 11 and hence 12 may be obtained from 9a or 9b.

The compound 13 may be obtained from compound 12 by operating as follows:

The derivative 12 is treated with the rhodium complex as described for 9a. The compound 13 is obtained with a yield of 90%. It is characterized by its IR and NMR spectra. In addition, treated with acetic anhydride (1 ml for 180 mg of 9a) it gives compound 10a.

According to another modification, the derivative 13 may be obtained from 10a or 10b by operating as described for the production of 17 from 9a or 9b.

EXAMPLE 2

Synthesis of the disaccharide 20 or methyl (1-bromo-3,6-di-O-acetyl-2-azido-4-O[2,3-di-O-benzyl]-4-O-chloroacetyl-β-D-glucopyranosyl)uronateβ-D-glucopyranose of the formula:

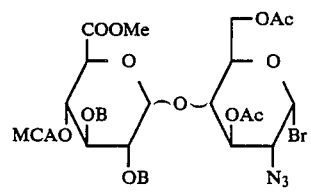

This synthesis includes the following steps (see FIGS. 3 and 4):

(A) The preparation from the derivative 13 of Example 1 of the monosaccharide 16 or methyl (1-bromo-2,3-di-O-benzyl-4-O-chloracetyl-β-D-glucopyranosyde)uronate;

(B) The condensation of compound 16 with the monosaccharide 17 leading to the disaccharide 18;

(C) The acetolysis of the compound 18 leading to the disaccharide 18 and, (D) Bromination giving the disaccharide 20.

(A) Preparation of the monosaccharide 17

This synthesis is carried out from the monosaccharide 13 or methyl (prop-1′-enyl 2,3-di-O-benzyl-β-D-glucopyranoside)uronate, by the three following steps:

1. chloroacetylation of compound 13;
2. unblocking of the anomeric carbon;
3. bromination of the anomeric carbon.

1. Chloroacetylation of the compound 13 leading to compound 14, namely methyl (prop-1′-enyl 2,3-di-O-benzyl-4-O-chloroacetyl-β-D-glucopyranoside)uronate.

2.8 g of compound 13 is dissolved in 30 ml of pyridine (6.56 mmoles). After cooling to 0° C. drop by drop, 10 ml of a solutin of 2 ml of chloroacetyl chloride in 20 ml of dichloromethane is added. After 30 minutes, it is evaporated to dryness, the residue is taken up again with 200 ml of chloroform, washed with a 10% KH SO$_4$ solution, then with water, it is dried and concentrated. The syrup obtained is chromatographed on silicate gel (200 g; eluent AcO-Et/hexane; ⅓; v/v). In this way 2.7 g of pure compound 14 are obtained in the form of syrup (yield 80%). $[\alpha]D^{20} = +2°$ (c=1.5; chloroform).

Elementary analysis and the NMR spectrum confirm the expected structure.

2. unblocking of the anomeric carbon leading compound 15 or methyl (2,3-di-O-benzyl-4-O-chloroacetyl-D-glucopyranoside) uronate.

2.7 g (5.3 mmoles) of derivative 14 in 80 ml of an acetone/water mixture (5/1; v/v) is dissolved. Mercuric oxide (3.1 g) is added followed by a solution of mercuric chloride (3.9 g) in acetone (27 ml). After 5 minutes, salts are removed by filtration. After concentration to dryness, the residue is taken up again with chloroform. The chloroform phase is washed with a 10% KI solution then with water. After evaporation, the product is crystallized in a methyl acetate/hexane mixture. 2 g of a solid of mp 105°–107° C. are obtained; $[\alpha]D^{20} = 4.7°$ (eq. 1 chloroform). Elementary analysis and the NMR spectra confirm the structure (yield 80%).

3. bromination of the anomeric carbon leading to the compound 16 or methyl (1-bromo-2,3-di-O-benzyl-4-O-chloroacetyl-α-D-glucopyranoside) uronate.

2 g (4.30 mmoles) of the compound 15 are dissolved in 50 ml of dichlormethane. 4.8 ml (34.4 mmoles) of sym-collidine at 0° C. is added, followed by bromomethylene dimethyl ammonium bromure (17 mmoles) prepared according to HEPBURN D. R. and HUDSON H. R. J. Chem. Soc. Perkin I (1976) 754–757.

After 4 hours of reaction, the mixture is diluted with 100 ml of dichloromethane, then poured into ice water. After washing with ice water, the solvent is evaporated. After chromatography on silicate gel (20 g; eluting hexane/ethyl acetate, 2/1; v/v) 2.06 g of compound 16 is obtained in the form of a syrup (yield 90%). $[\alpha]D^{20} = +82.5°$ (c=1.5; chloroform). analysis and the NMR study confirm the structure.

(B) Preparation of the disaccharide 18 or 3O-acetyl-1,6-anhydro-2-azido-4-O 2,3-di-O-benzyl-4-O-chloroacetyl-β-D-glucopyranosyl methyl uronateβ-D-glucopyranose.

This synthesis is based on the condensation of the monosaccharides 16 and 17 of 870 mg (3.8 mmoles).

To a solution of 870 mg (3.8 mmoles) of compound 17, in dichloromethane, is added 1 g of drierite 0.5 g of molecular sieve 4 Å, in powder, and 0.525 g of freshly prepared silver carbonate. After 2 hours stirring, compound 16 is added drop by drop at 0° C. (670 mg) (1.3 mmoles). After 6 days, the solids are removed by filtration. The syrup obtained after concentration is chromatographed on silica gel (50 g; eluent: chloroform/ethyl acetate; 4/1, v/v). The disaccharide 18 is obtained in the form of a foam (421 mg; 50%). $[\alpha]D^{20} = -17°$ (c=1, chloroform). Elementary analysis confirms the structure. NMR study confirms the configuration of the interglycosdic linkage.

(C) Preparation of the disaccharides of structure 19 by acetolysis of the disaccharide 18.

The disaccharides 19 are prepared by subjecting the disaccharide 18 to an acetolysis reaction as follows.

300 mg of compound 18 are dissolved in a mixture of 4 ml of acetic anhydride and 0.5 ml of freshly distilled trifluoroacetic acid. The reaction mixture is subjected to stirring for 10 hours at 18° C., then evaporated to dryness and co-evaporated with toluene. The residue is chromatographed on a column of silica gel (15 g). By elution with a dichloromethan ethyl acetate mixture (19:1, v/v), 282 mg of a mixture of anomeric acetates of structure 19 are obtained in the form of a colorless syrup (yield 86%). The ration of the forms to the forms, determined by NMR analysis, is 4/1.

NMR spectrum confirms the expected structure.

(D) Preparation of disaccharide 20 by bromidation of the disaccharides 19.

The mixture of acetates of structure 19 is subjected to the action of TiBr$_4$: A solution of 140 mg of the acetates mixture 19 in a mixture of 3 ml of dichloromethane and of 0.3 ml of ethyl acetate is subjected to stirring at 17°–18° C., under a dry argon atmosphere, in the presence of 140 mg of TiBr ($\simeq$2 equivalents) for 20 hours. After cooling to 0° C. and dilution with 30 ml of dichloromethane, the mixture is washed with ice water, then with an aqueous 5% solution of potassium bromide and then with water and dried over sodium sulphate, filtered and evaporated. The residue is chromatographed on a silica gel column (10 g). By elution with ethyldichloromethane acetate mixture (19:1, v/v), there is recovered, in order of elution:

bromide 20 (74 mg; yield 50%) in the form of a colorless syrup, nonstable (immediately engaged in the following reaction);

NMR spectrum confirms the expected structure.

a fraction (28 mg; yield 20%) corresponding to the unreacted starting material, a fraction hardly migrating corresponding to products with partial O-debenzylation.

EXAMPLE 3

Synthesis of the monosaccharide 22 or benzyl 6-O-acetyl-3-O-benzyl-2-benzyloxycarbonylamino-2-desoxy-α-D-glucopyranoside of the formula:

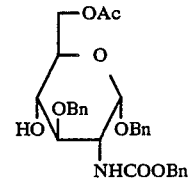

This derivative is prepared from benzyl-3-O-benzyl-2-benzyloxy-carbonylamino-2-desoxy-α-D-glucopyranoside (derivative 21) by proceeding as follows (see FIG. 5):

A suspension of compound 21 (987 mg, 2 mM), this compound is prepared according to P. C. Wyss and J. Kiss, Helv. Chim, Acta, 58 (1975) 1833–1847) in anhydrous 1,2-dichloroethane (15 ml) is stirred under reflux for 30 h in the presence of N-acetyl-imidazole (freshly prepared 2.5 mM). After a cooling and dilution with chloroform (50 ml), the organic phase is washed with an M chlorid acid solution, with water, with a saturated aqueous solution of hydrogen carbonate, with water, dried (sodium sulphate), filtered and evaporated. The residue is chromatographed on a silica gel column (50 g). Elution with the mixture dichloromethane-acetone (15:1, v/v) gives the derivative 22 in the form of a syrup crystallizing in a mixture of ethyl acetate-hexane (759 mg, 71%), M.P.: 114°–115° C.; $[\alpha]_D = +88°$ (c=1, chloroform).

EXAMPLE 4

Synthesis of the monosaccharide 33 of the formula

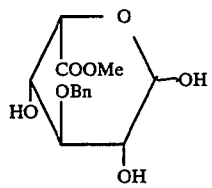

The synthesis is carried out from compound 23 by the following steps (see FIG. 6):
(1) introduction of a benzoyl group at the 5 position,
(2) methylation of the carboxyl function at position 6,
(3) isomerisation of the OH group at position 5,
(4) formation of the pyran ring.

(1) benzoylation reaction 63 g of 3-O-benzyl-1,2-O-isopropylidene-α-D-glucofuranoside (compound 23) are dissolved in 500 ml of anhydrous pyridine. 85 g of trityl chloride is added and it is heated to 80° C. for one hour. In this way the compound 24 is obtained.

Rotatory Power: $[\alpha]_D^{20} = -34.7°$, chloroform.

The structure of this compound has been confirmed by its IR and NMR spectra, its elementary analysis is correct.

The mixture is then cooled to 0° C. and 45 ml of benzoyl chloride added. After one night, the excess of reagents are destroyed by the addition of 300 ml of methanol. The mixture obtained, evaporated to dryness is taken up again with chloroform. The chloroform phase is washed with water, dried over sodium sulphate and concentrated. In this way the compound 25 is obtained.

The syrup obtained is dissolved in 400 ml of chloroform. After addition of 100 ml of a 5M paratoluene-sulphonic acid solution in methanol, the solution is left at 4° C. over night. After washing the organic phase with water, 215 g of a mixture is obtained. The compound is obtained by chromatography of this mixture on silica gel in the solvent ether-hexane 2/1 (v/v). In this way 36 g of compound 26 is obtained.

Rotatory power: $[\alpha]_D^{20} = 65.3°$, chloroform. The structure of the compound 26 has been confirmed by its IR and NMR spectra.

(2) methylation of the carboxyl function at 6 position

The compound 26 (1.88 g) is dissolved in acetone (20 ml). Drop by drop at 50° C., 3.5 ml of a solution of CrO$_3$ (13 g) in H$_2$SO$_4$, 3.5M (29 ml) is added. The temperature is allowed to rise again and it is left for one hour under these conditions. The reaction mixture is then poured into ice and the product is extracted with chloroform. After washing with water and drying, it was evaporated to dryness. The compound 27 was obtained.

The mixture obtained is dissolved in methanol (20 ml), then 10 ml of 1N soda added and it is left over-night at room temperature. The reaction mixture is then passed through a column (25 ml) of Dowex 50 resin in the H+ form previously rinsed with methanol. The product is obtained by concentration of the eluate. In this way the compound 28 is obtained. This compound is dissolved in ether and methylated conventionally with diazomethane. After evaporation, the compound 29 (1.08 g; 70.4%) is obtained.

Rotatory power: $[\alpha]_D^{20} = -27°$, chloroform.

Elementary analysis found of the compound 29 is correct. It structure is moreover confirmed by its IR and NMR spectra.

(3) isomerisation of the —OH group at the 5 position.

To a solution of triflic anhydride (0.8 ml) in dichloromethane (16 ml), cooled to −20° C., is added drop by drop a solution of pyridine (0.8 ml) in dichloromethane (8 ml). Then at −10° C., drop by drop, is added 800 mg of compound 29 dissolved in dichloromethane (8 ml). After one hour at −50° C., the reaction mixture is poured into a mixture of water and ice (8 ml) containing 160 mg of sodium bicarbonate. It is stirred until separation of the two organic and aqueous phases. The organic phase is washed with 3% HCl, H$_2$O, saturated NaCl, dried and concentrated. In this way the compound 30 is obtained.

The syrup is taken up again with DMF (10 ml). Sodium trifuloroacetate (1.6 g) is added and is heated to 80° C. for three hours. In this way the compound 31 is obtained. After evaporation, taking up again with dichloromethane, washing with water and drying, the residue is taken up again with methanol and then the solvent is evaporated after one hour. After chromotography on a column in the solvent ether-hexane 2/1, the compound 32 is obtained (450 mg: 56.2%).

Rotatory power: $[\alpha]_D^{20} = -33°$, chloroform The structure of compound 32 is confirmed by its IR and NMR spectra. Elementary analysis found is correct.

(4) formation of the pyran ring

This synthesis is carried out from the compound 32. The compound 32 (200 mg) is dissolved in a mixture of trifluoroacetic acid/water 9/1). After 15 minutes, the solvents are evaporated. The residue is crystallised in ethyl acetate/hexane. In this way 110 mg of compound 33 are obtained.

The characteristics of this derivative are as follows:

IR spectrum: in CHCl$_3$, in cm$^{-1}$: 3450(OH, 3080, 3060, 3030 (CH$_2$: benzyl) and 1740 (COOCH$_3$).

NMR spectrum: δ in ppm with respect to TMS: 3.75 (s, 3H+, COOMe) 4.98 (1H+), 7.30 (s, 5H+, C$_6$H$_5$)

rotatory power: $[\alpha]_D^{20} = +13°$, methanol, elementary analysis for

| C$_{14}$ H$_{18}$ O$_7$ | calculated | found |
| --- | --- | --- |
| C | 56.37 | 56.17 |
| H | 6.08 | 5.85 |
| M.P. | 125–126° C. | |

EXAMPLE 5

Synthesis of the derivative 38 or 3-O-benzyl-4-O-chloroecetyl-1,2-O-tert. butoxyethylidene-β-L-methyl idopyranuronate of the formula

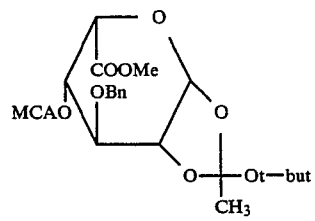

This synthesis (see FIG. 7) is carried out from the derivative 33 with an iduronic acid structure by subjecting (α) the derivative 33 to an acetylation reaction, (β) the mixture of anomeric acetates 34 and 35 obtained, to the action of a brominating agent in order to introduce a bromine atom onto the anomeric carbon, (α) by forming an orthoester at the 1, 2 positions and (δ) by carrying out a monochloroacetylation at the 4 position of the orthoester.

(α) acetylation reaction leading to 1,2,4-tri-O-acetyl-3-O-benzyl-α,β-L-methyl idopyranuronates (derivatives 34 and 35).

A solution of compound 33 (3 g) in a mixture of anhydrous pyridine (20 ml) and acetic anhydride (10 ml) is stirred at 0° C., protected from moisture, for 5 h. The reaction mixture is evaporated to dryness, evaporated with toluene (4×20 ml), and dried under vacuum. The residue is chromatographed on a silica gel column (150 g). Elution by the mixture toluene:ethyl acetate (4:1 v/v) gives, in order of elution:

a head fraction composed of furane derivatives, the compound 34, (αanomer), syrup, (170 mg, 4%), $[\alpha]_D = -43°$; (c: 1, chloroform), N.M.R. (CDCl$_3$): δ: 6.23 (s, 1H, H-1).

the compound 35 (βanomer), crystallizing in a mixture ether-hexane, (2.688 g, 63%), M.P.: 112°–113° C., $[\alpha]_D = +9°$ (c: 1, chloroform) N.M.R. (CDCl$_3$): δ: 6.08 (d, 1H, H-1, $J_{1,2}$: 1.5 Hz).

The α and β anomers 34 and 35 are not separated when proceding with the sequence of synthesis described. Their mixture is used directly in the form of a syrup for the subsequent reactions.

(β) bromuration reaction leading to the compound 36 or 2,4-di-O-acetyl-3-O-benzyl-α-L-methyl idopyranuronyl bromide A mixture of acetates 34 and 35 (212 mg; 0.5 mM) is dissolved in anhydrous dichloromethane (5 ml) and anhydrous ethyl acetate (0.5 ml). Titanium tetrabromide (250 mg, 0.7 mM) is added in one lot, and the reaction mixture is stirred for 24 h at room temperature protected from moisture. After cooling to 0° C. and dilution with dichloromethane, the organic phase is washed with ice water (3 times), dried (sodium sulphate), filtered and evaporated to give the derivative 36 in the form of a light coloured syrup (217 mg, 96%), N.M.R. (CDCl$_3$): δ: 6.41 (s, 1H, H-1). This compound, very unstable is immediately engaged in the following reaction.

(δ) preparation of the orthoester of 4-O-acetyl-3-O-benzyl-1,2-O-tert-butoxyethylidene-β-L-methyl /idopyranuronate.

A solution of bromide 36 (freshly prepared from 1.211 g, 5 mM, of a mixture of acetates 34 and 35 in anhydrous dichloromethane (20 ml) is stirred at room temperature under a dry argon atmosphere. Sym-collidine (2.65 ml, 20 mM) and anhydrous tert-butanol (3 ml; 30 mM) are successively added and the reaction mixture is stirred for 15 h under these conditions. After dilution with dichloromethane (50 ml) the organic phase is washed with a saturated aqueous solution of sodium hydrogencarbonate, with water, dried over sodium sulphate, filtered and evaporated. The residue is chromatographed on a silica gel column (120 g). Elution by the mixture hexane:ethyl acetate (2:1, v/v, containing 0.5% of triethylamine) gives compound 37 in the form of a pure syrup (1.542 g, 70% from 34 and 35) $[\alpha] = -23°$ (c: 1, chloroform), N.M.R. (CDCl$_3$): δ: 5.48 (d, 1H, H-1, $J_{1,2}$: 2.5 Hz).

(δ) monochloroacetylation of the orthoester 37:

A solution of the orthoester 37 (220 mg, 0.5 mM) in anhydrous methanol (10 ml) is cooled to −20° C. with stirring and under a dry argon atmosphere. Anhydrous potassium carbonate (40 mg) is added and the reaction mixture is stirred for 5 h under these conditions. The solids are drained, the filtrate evaporated and the residue is taken up again in chloroform (50 ml). The organic phase is washed rapidly with ice water (3 times), dried (sodium sulphate), filtered and evaporated. The residue is immediately dissolved in anhydrous pyridine (4 ml) and anhydrous dichloromethane (2 ml). After cooling to −20° C. under a dry argon atmosphere, a solution of chloroacetyl chloride (0.1 ml, 1.24 mM, freshly distilled) in anhydrous dichloromethane (1 ml) is added drop by drop. The reaction mixture is stirred under these conditions for 30 min, then poured into water-ice mixture (100 ml). After stirring for 15 min, the mixture is extracted with chloroform 3×20 ml). The organic phases are washed with ice water, with an aqueous solution of 2% sodium hydrogencarbonate, with water, dried (sodium sulphate), filtered and evaporated. The residue is rapidly chromatographed on a silica gel column (12 g). Elution with the mixture hexane:ethyl acetate (5:2, v/v, containing 0.2% of triethylamine) gives in order of elution:

an unsaturated compound 39 (15 mg, 8%), the orthoester 38 syrup (145 mg, 61% from 12), $[\alpha]_D = +19°$ (c: 1, chloroform), N.M.R. (CDCl$_3$): δ: 5.45 (d, 1H, H-1, $J_{1,2}$: 2.5 Hz), 5.24 (d.de d., 1H, H-4, $J_{3,4}$: 2.5 Hz, $J_{4,5}$: 1.5 Hz), 4.00 (s, 2H; Cl—CH$_2$—COO—).

EXAMPLE 6

Synthesis of the disaccharide 41 or benzyl 6-O-acetyl-3-O-benzyl-2-benxyloxycarbonylamino-2-desoxy-4-O-(2-O-acetyl-3-O-benzyl-α-L-methyl idopyranuronyl)α-D-glucopyranoside

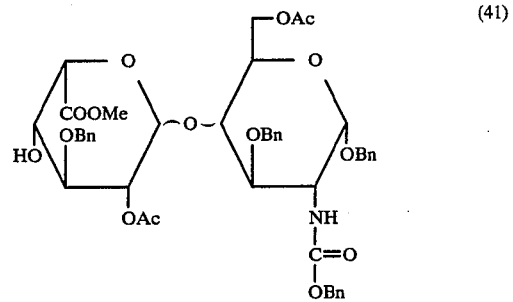

(41)

Figure 8:
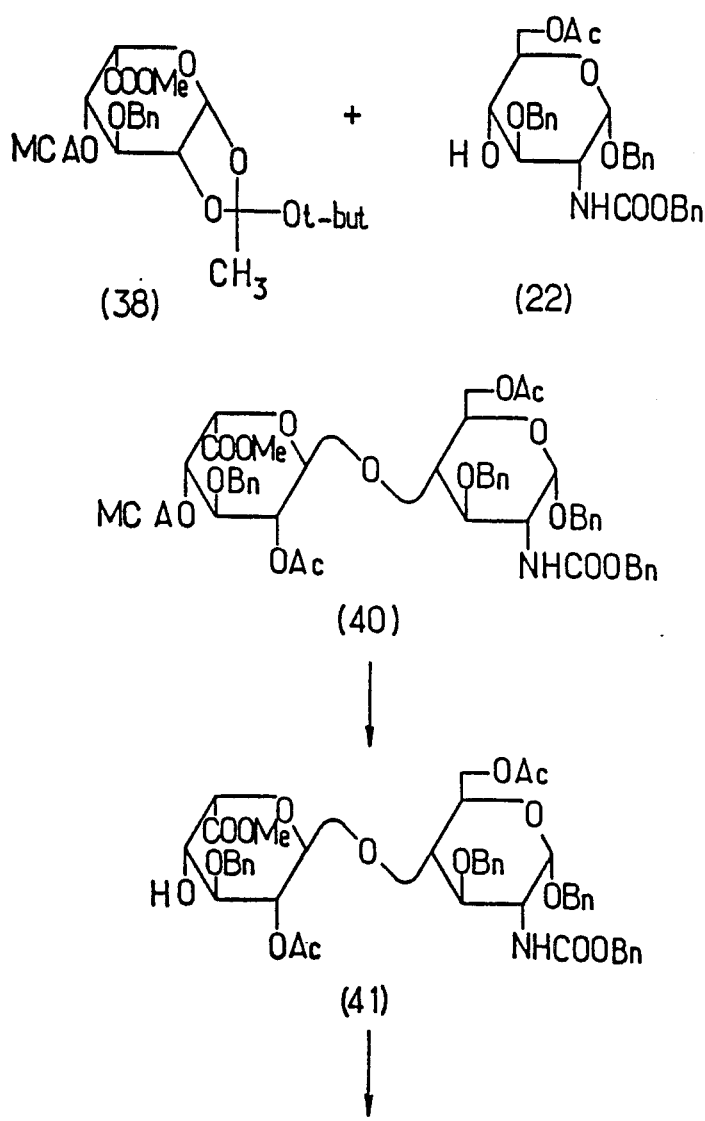
Figure 9:
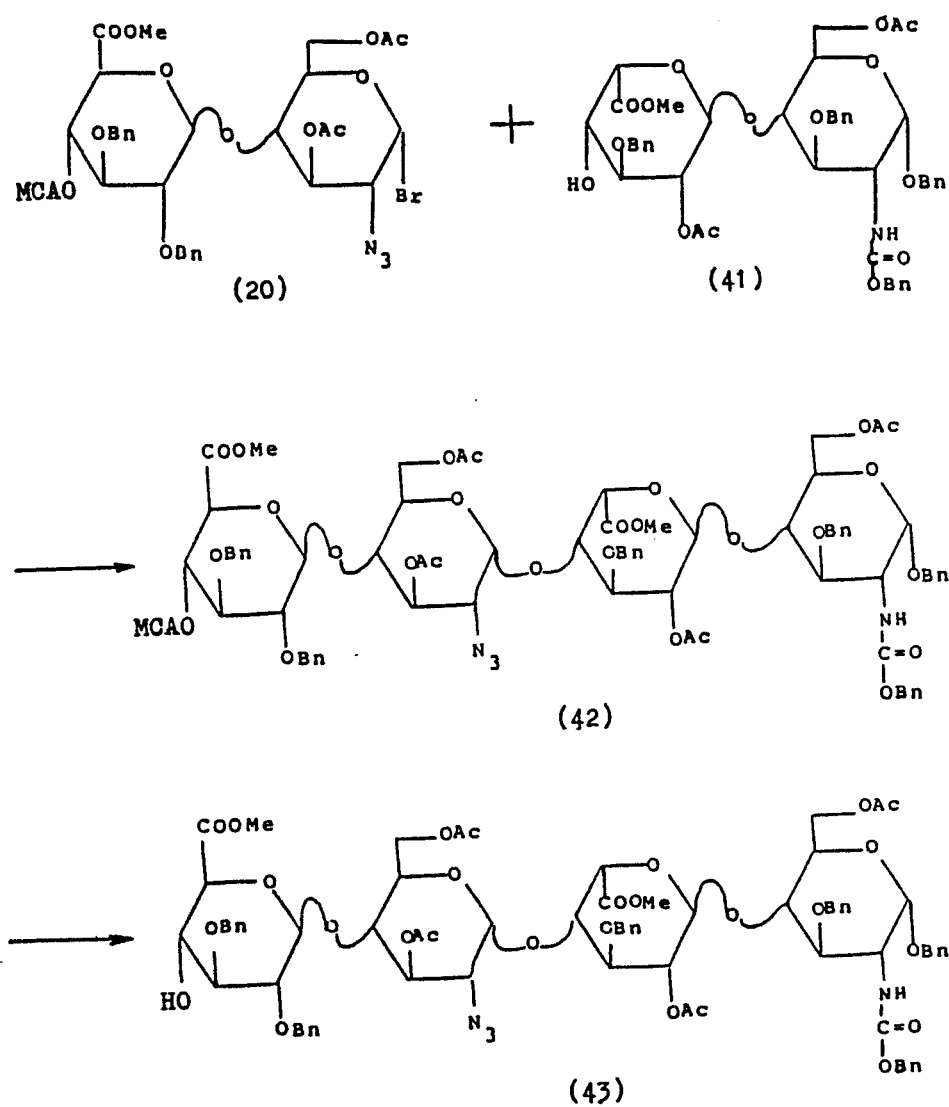

Firstly the disaccharide 40 is prepared according to step α) by condensation of the monosaccharides 38 and 22, then the monochloroacetyl group is removed at the 4 position in step β, which leads to the desired disaccharide 41 (see FIG. 8).

Step α: Preparation of the disaccharide 40 or benzyl 6O-acetyl-3-O-benzyl-2-benzyl-2-benzyloxycarbonylamino-2-desoxy-4-O-(2-O-acetyl-3-O-benzyl-4-O-chloroacetyl-α-L-methylidopyranuronyl)-α-D-glucopyranoside.

A solution of the orthoester 38 (284 mg, 0.6 mM) and alcohol 22 (214 mg, 0.4 mM) in anhydrous chlorobenzene (12 ml) is heat to 140° C. with stirring and a slight current of dry argon. After slow distillation of 10 ml of solvent a solution of 2,6-dimethylpyridinium perchlorate (0.006 mM, freshly prepared) in chlorobenzene (4 ml) is added drop by drop in 30 min with simultaneous distillation of solvent (4 ml). The reaction mixture is stirred 1 h, with the addition of fresh solvent (10 ml) and simultaneous distillation so that the reaction volume remains constant and equal to 4 ml. After cooling and dilution with chloroform, the organic phase is washed with a saturated solution of sodium hydrogen carbonate, with water, dried over sodium sulfate, filtered and evaporate The residue is chromatographed on a column of silica gel (40 g). Elution by the mixture hexane:ethyl acetate (4:3, v/v) gives, in order of elution:

the product 22, (120 mg, 56%)

the disaccharide 40, crystallised in a mixture ether-hexane (112 mg, 30%, MP: 144°145° C., $[\alpha]_D^{20} = \times 35°$ (c: 1, chloroform), NMR (CDCl$_3$): in accordance with the expected structure.

Step $\beta$: removal of the monochloroacetyl group.

A mixture of the disaccharide 40 (56 mg, 0.06 mM) and of thiourea (7 mg, 0.1 mM) in pyridine (2.5 ml) and absolute ethanol (0.5 ml) is stirred at 100° C. for 30 min. After cooling and evaporation to dryness, the residue is taken up again with a mixture of water-chloroform (1:1, v/v 40 ml). The organic phase is washed with water, dried (sodium sulfate), filtered and evaporated. The residue is chromatographed on a silica gel column (2 g). Elution by the mixture ethyl acetate:hexane (2:2, v/v) gives the disaccharide 41, crystallised in ether (46 mg, 30%), M.P.: 146°-147° C. $[\alpha]_D = 44°$ (c: 1, chloroform), NMR (CDCl$_3$): in accordance with expected structure.

EXAMPLE 7

Synthesis of the tetrasaccharide 43 of the formula h to stirring at −20° C., then the temperature is allowed to rise again to ambient temperature of 15 h. After dilution with 50 ml of dichloromethane, the solids are drained and the filtrate is washed with an iced aqueous solution of 1M hydrochloric acid with water (twice). It is then dried over sodium sulfate, filtered and then evaporated.

The residue is chromatographed on a silica gel column (8 g, gel 230-400 mesh). Elution by the mixture hexane-ethyl acetate (4:3, v/v) enables recovery of 37 mg of tetrasaccharide 42 (yield 39%) in the form of a colorless glass. $[\alpha]_D^{20} = 56°$ (c=0.6; CHCl$_3$); the NMR spectrum confirms the expected structure.

By elution of the column with the mixture ethyl acetate-hexane (2:1, v/v), 23 mg of the starting product 41 is recovered (yield 44%).

(b) -O-dechloroacetylation reaction

A solution of 36 mg (23M) of the tetrasaccharide 42 in 1.25 ml of a mixture of pyridine and 0.25 ml of absolute ethanol is heated to 100° C. in the presence of 7 mg (100 μM) of thiourea for 20 min. After cooling and evaporation to dryness, the solid residue is taken up again with 20 ml of water and extracted with chloroform (5 times 5 ml). The organic phases are washed with an aqueous 10% sodium hydrogen sulfate solution, with water, dried over sodium sulfate, filtered and evaporated. The residue is chromatographed on a silica gel column (3 g). By elution with an ethyl acetatehexane mixture (3:2, v/v), 27 mg of the derivative 43 is obtained (yield 80%) in the form of a colorless glass $[\alpha]_D^{20} = +61°$ C. (c=0.8; chloroform); the NMR spectrum confirms the expected structure. (see FIG. 31).

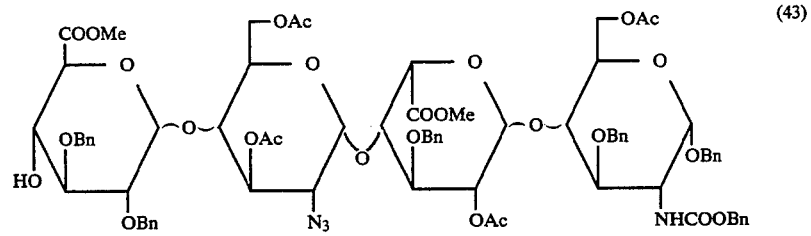

(43)

The tetrasaccharide 43 is prepared by carrying out: in step (a) the condensation of the disaccharides 20 and 41 whose synthesis is described in Examples 2 and 6 and by subjecting in the course of step (b) the tetrasaccharide 42 formed to a selective —O— dimonochloroacetylation reaction at the 4 position (see FIG. 9):

(a) Condensation reaction

A mixture of 64 mg (80M) of the bromide 20 freshly prepared, 51 mg (60 μM) of the compound 41 and 80 mg of molecular sieve 4 Å in powder in 1.5 ml of anhydrous dichloroethane is subjected to stirring for a half-hour at room temperature, under a dry argon atmosphere, then cooled to −20° C. Successively 20 ml (150M) of sym-collidine at 31 mg (120M) of silver triflate are added. The reaction mixture is subjected for 1

EXAMPLE 8

Figure 10:
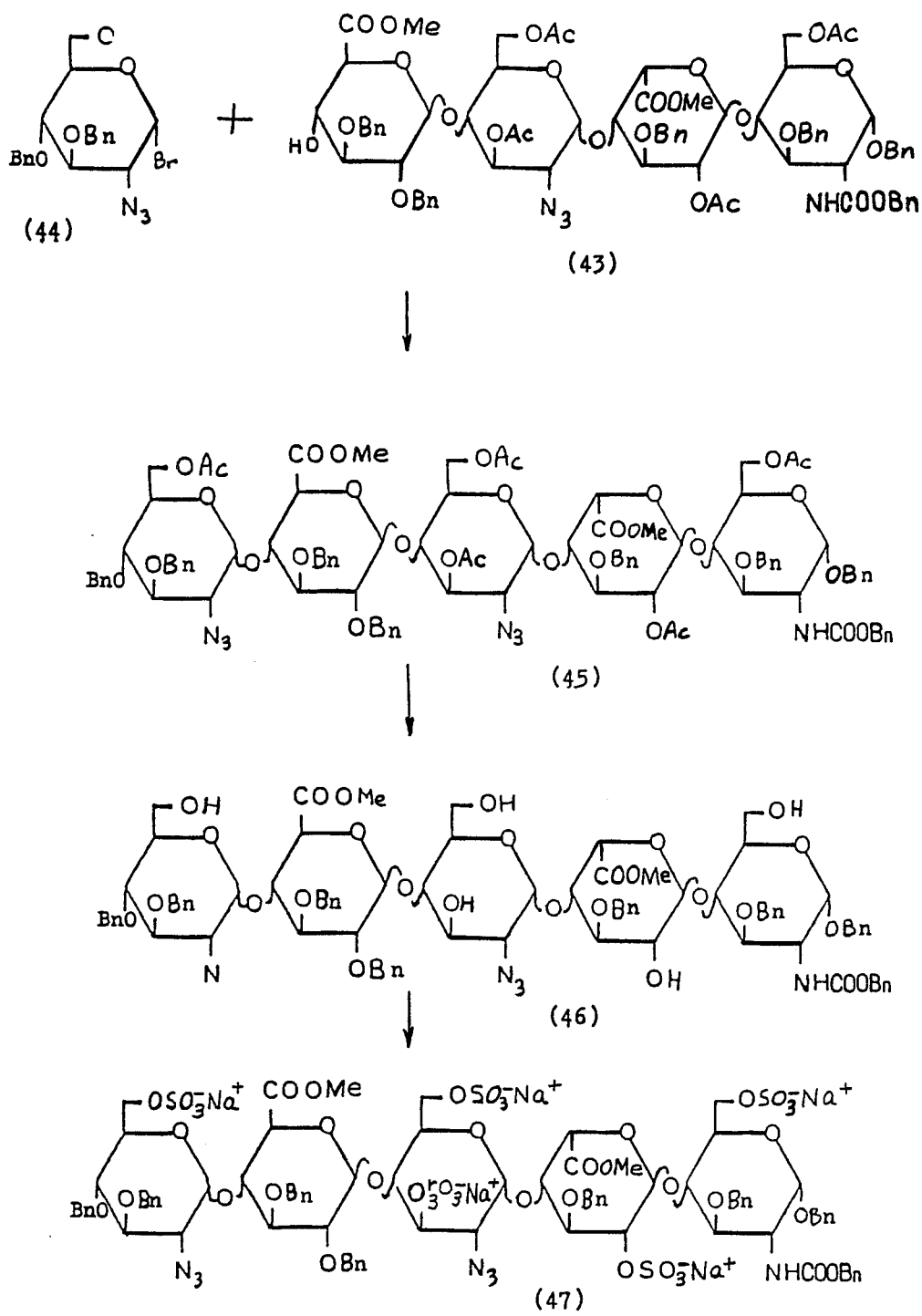

(see FIG. 10)

Synthesis of the pentasaccharide 45 of the formula

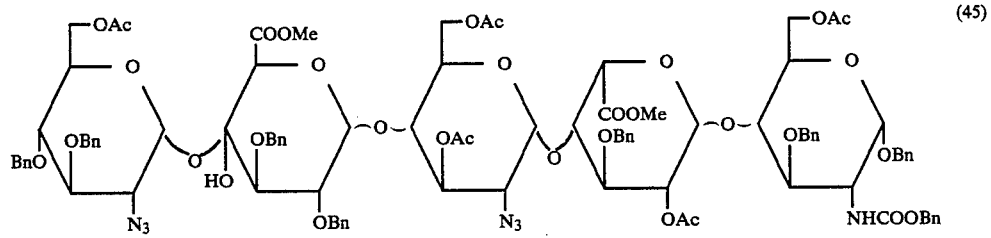

(45)

A condensation reaction is carried out between the tetrasaccharide 43 and the monosaccharide 44, which lead to the pentasaccharide 45.

A mixture of 27 mg (54 μM) of bromide 48 prepared according to H. PAULSEN und. W. STENZEL, Chem. Ber., 111 (1978) 2334-2347, of 26 mg (18 μM) of tetrasaccharide 43 and 50 mg of molecular sieve 4 Å in powder in 0.8 ml of dichloroethane is subjected to stirring for ½ h at room temperature under a dry argon atmosphere, then cooled to −20° C. 16 ml (120M) of sym-collidine and 26 mg (100 μM) of silver triflate are added successively and the reaction mixture is subjected to stirring for 18 h allowing the temperature to rise slowly to room temperature.

After dilution with 50 ml of dichloromethane, the solids are drained and the filtrate is washed with a 1M aqueous iced hydrochloric acid solution then with water (twice). It is then dried over sodium sulfate, filtered, and then evaporated.

The residue is chromatographed on silica gel column (5 g, 230–400 mesh gel). By elution with a hexane-ethyl acetate (4:3, v/v), mixture, 30 mg of pentasaccharide 45 is recovered in the form of a colorless glass (yield 90%) $[\alpha]_D^{20}$−'67° (c 1: chloroform). The NMR spectrum confirms the expected structure. In particular, for the anomeric protons of the glucosamine units displacements (δ, TMS) of 5.36 and 5.52 ppm are fround for the protons belonging to H, F and D respectively.

EXAMPLE 9

Preparation of the pentasaccharide 50

Figure 11:
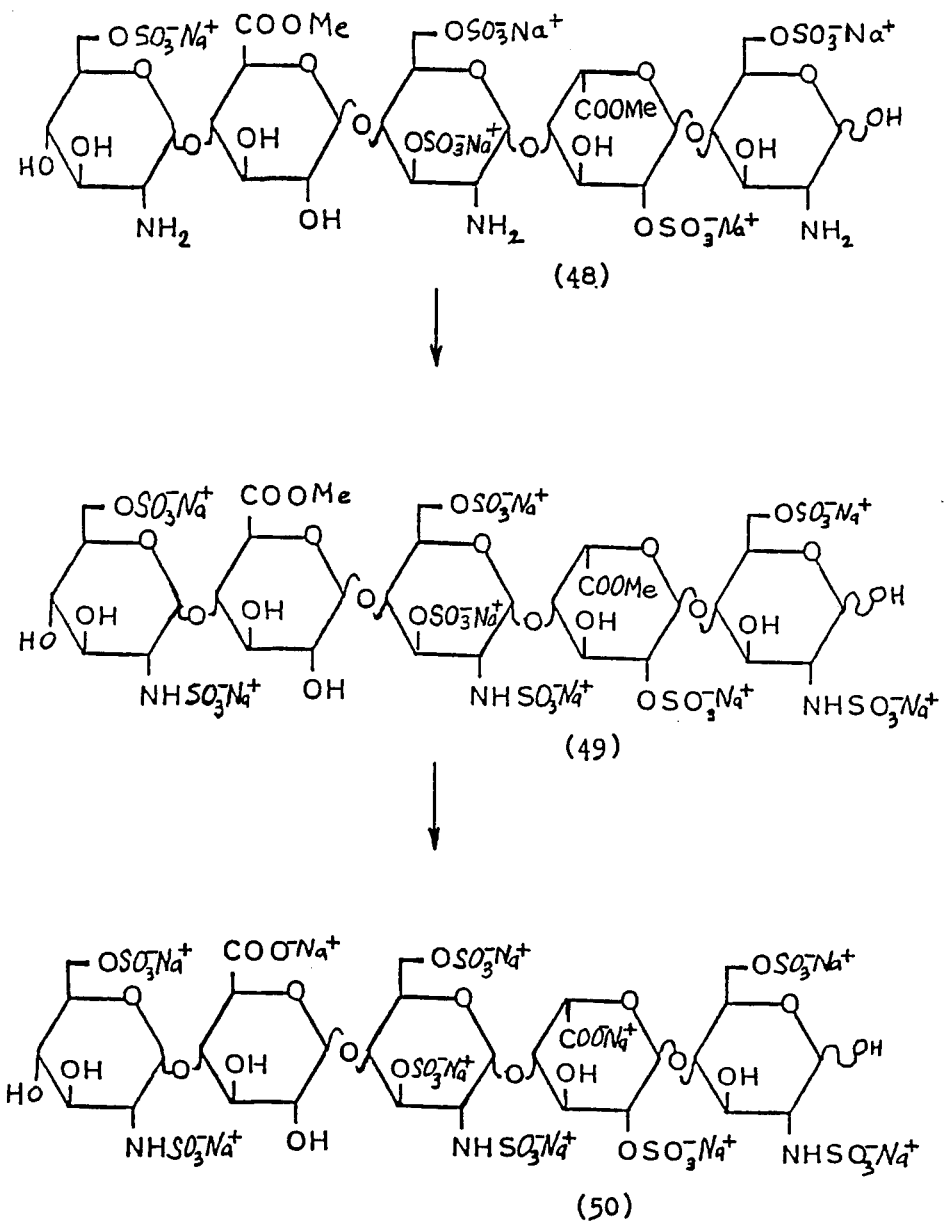

(see FIGS. 10 and 11)

Recourse is had to the following steps:

(a) removal of the acetyl groups (pentasacchride 46)

(b) sulfation of the thus-liberated —OH groups (pentasaccharide 47)

(c) hydrogenation to liberate the —OH groups protected by the benzyl groups and to convert the —N$_3$ group into a —N$_2$ group (pentasaccharide 48)

(d) sulfation of the NH$_2$ groups (pentasaccharide 49) then saponification of the —COOMe groups at the 6 position (pentasaccharide 50)

These steps are carried out as follows:

(a) removal of the acetyl groups of the derivative 45.

A solution of 28 mg of the pentasacchride 45 in a mixture of 2.5 ml of 1,2-diemthoxyethane and 0.8 ml of methanol is cooled to 0° C. with stirring. Then 1 ml of a 1M soda solution is added drop by drop, in 10 minutes. The reaction mix is subjected to stirring 1 hour at 0° C., then 12 hours at room temperature. After cooling to 0° C., 3 ml of 1M hydrochloric acid is added and the milky mixture is immediately extracted with chloroform (5 times 5 ml). The organic phases are washed with water, dried over sodium sulfate, filtered and evaporated. The residue is taken up again in 2 ml of methanol and treated with an ether solution of diazomethane (excess until the persistance of the yellow color) for a half-hour.

After evaporation to dryness, the residue is chromatographed on a silica gel column (2 g, 230–400 mesh gel). Elution by the mixture dichloromethane-methanol (15:1, v/v) enables the recovery of 18 mg of the pentasaccharide 46 (yield 72%) in the form of a colorless glass. $[\alpha]_D^{20}$−+57° (c=1; chloroform);

The expected structure is confirmed by the NMR spectrum.

(b) sulfation of the —OH groups

To a solution of compound 46 (22 mg) in di-ethylformamide (0.5 ml), is added the complex trimethylamine/SO$_3$ (22 mg, 2.5 eq/OH). The reaction mixture is heated at 50° C. for about 14 h. Then the complex trimethylamine/SO$_3$ (10 mg) is again added and the reaction is allowed to develop for 24 hours. To the reaction mixture are then added methanol (0.5 ml) and chloroform (0.5 ml). The solution is introduced at the top of a Sephadex LH$_{20}$ column equilibrated in a CHCl$_3$/CH$_3$OH (1/1; v/v) mixture. The fractions containing the sulfated product are grouped together and the solvent is evaporated. In this way a glass is obtained (30 mg). This glass is then chromatographed on silica gel (10 g) in a solvent constituted by 3 parts of the mixture ethyl acetate/pyridine/acetic acid/water, (6/2/0,6/1, v/v/v/v) and 2 parts of the mixture ethyl acetate/pyridine/acetic acid/water, (5/5/1/3, v/v/v/v).

The fractions containing the desired product are collected and concentrated. After evaporation of the solvents, the residue obtained is dissolved in methanol suplemented with water, then passed through a Dowex 50 W×4, Na+ column, equilibrated in a mixture methanol/water (50/50, v/v). In this way the sodium salt (compound 47 is obtained).

(c) hydrogenation

The product obtained above is dissolved in methanol (3.7 ml) supplemented with water (0.3 ml).

To this solution, is added the catalyst (Pd/C, 5%, 40 mg) and it is stirred under a hydrogen atmosphere for 5 days. After removal of the catalyst by filtration, analysis of the U.V. spectrum of the solution obtained shows the complete disappearance of the absorption due to the benzyl groups. The solvent is then evaporated, leaving a residue, namely the compound 48.

(d) sulfation of the —NH$_2$ groups, then saponification of the carboxyl groups.

Compound 48 is dissolved in water (4 ml). The pH is then adjusted to 9.5 then the complex trimethylamine/SO$_3$ (54 mg) is added to the solution. The pH is kept at 9.5 throughout the reaction by the addition of 0.1N soda.

After one night, a further addition of sulfating agent is made (27 mg). A last addition is carried out after 24 h.

After 48 h, soda is added (3M, 34 ml) to the compound 49 formed, then the solution is subjected to stirring for 3 hours at room temperature so as to hydrolyse the methylesters of the uronic acid type units. The reaction mixture is then neutralized and then concentrated to a volume of about 2 ml. The solution so obtained is placed at the top of a Sephadex G 25 column (100 ml) eluted with water. The fractions collected are analysed by UV absorption (206 nm) and by polarometry (265 nm). The fractions having optical activity are grouped, the solvent is removed and the residue taken up again by about 2 ml of water and freeze-dried.

In this way the derivative 50 is obtained in the form of a white powder (5.6 mg, 25% with respect to the product 45).

The NMR study confirms the expected structure. It is found in particular for the anomeric protons of the glucosamine units, that the displacements are (δ, TMS) 5.36, 5.45 and 5.52 ppm for the protons belonging to H, F and D respectively.

EXAMPLE 10

Synthesis of the disaccharide 51, namely methyl 1 prop-1'-ethyl2,3-di-O-benzyl-4-O[2-azido-3,4-di-O-benzyl-6-O-acetyl-α-D-glucopyranoside] uronate of the formula

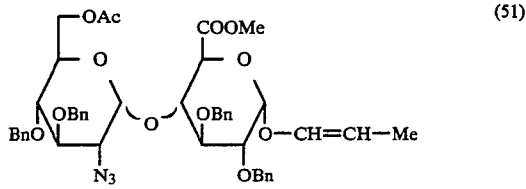

Figure 12:
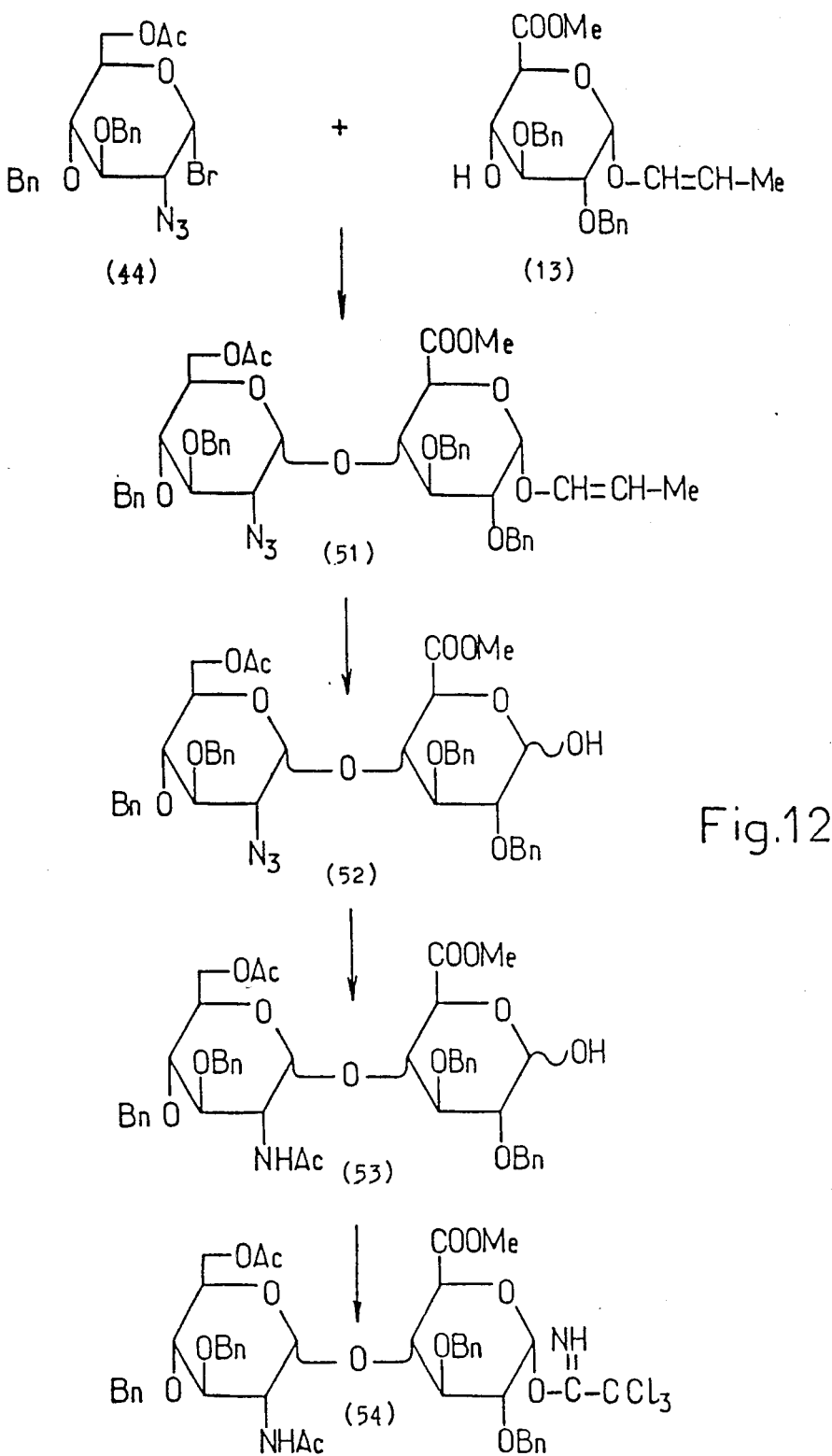

Reference will be made to FIG. 12.

To a solution of monosaccharide 13 (0.215 g; 0.5 mmole) in dichloromethane (3 ml), are added the monosacchride 44 (0.49 g; 1 mmol) in dichloromethane (3 ml) and then 4 Å sieve in powder form. The mixture is cooled to 0° C., then there is added sym-collidine (0.16 ml) and silver triflate (0.3 g). After 1 hour, the mixture is diluted with dichloromethane (50 ml). The solids are drained, and then the solution is washed with a 5% solution of sodium bicarbonate, with water, then with 10% acid potassium sulfate and again with water. In this way, there is obtained after evaporation 591 mg of residue. After purification on silica in a toluene/acetone 30/1 (v/v) mixture, 211 mg of pure disaccharide 51 are recovered.

This product is characterized by its elementary analysis.

EXAMPLE 11

Synthesis of the disaccharide 54, namely methyl (1-trichloroacetimidyl-2,3,-di-O-benzyl-4-O-]2-acetylamido-2-desoxy-3,4-di-O-benzyl-6-O-acetyl-α-D-glucpyurampside]uronate of the formula

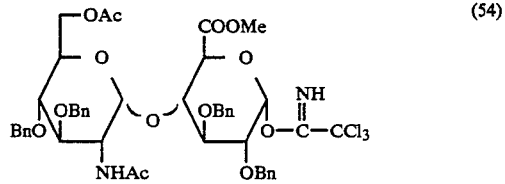

Reference will be made to FIG. 12 for the synthesis diagram.

To a solution of the disaccharide 51 (180 mg) in 6 ml of a mixture acetone/water (5/1; v/v), are added successively mercuric oxide (232 mg) and then drop by drop a solution of mercuric chloride in an acetone/water mixture (292 mg/2 ml).

After filtration, evaporation, taking up again with chloroform and washing with a 10% potassium iodide solution and with water, the disaccharide 52 is obtained (140 mg).

100 mg of the disaccharide 52 is dissolved in 0.6 ml of methanol. To this solution, are added ammonium formiate (160 mg) and 10% Pd/C catalyst (100 mg). After 5 minutes, the catalyst is removed and acetic anhydride added (10 drops). After evaporation, the product obtained is purified on silica in a toluene/acetone mixture (4/1; v/v). In this way 61 mg of disaccharide 53 are obtained.

The disaccharide 53 is characterized by its Rf on a silica plate (Merck, reference 5719) in two different solvents: chloroform/ethyl acetate, 3/2, v/v Rf=0.40 and toluene/acetone, 4/1, v/v; Rf=0.20.

The derivative 53 (60 mg) is dissolved in dichloromethane (1.5 ml). Then trichloroacetonitrile (75 l) and sodium hydride (1.5 mg) are added. After 15 minutes, the derivative 53 had disappeared to the advantage of the derivative 54. After filtration and evaporation, 5 is obtained (67 mg). The derivative 54 is characterized by its Rf on a silica plate (Merck, reference 5719) chloroform/ethyl acetate 2/1, v/v; Rf=0.59 (0.37 for the compound 53).

EXAMPLE 12

Synthesis of the derivative 57, namely methyl 1,6-anhydro-2,3-epoxy-4-O[2,3-di-O-benzyl-uronate]-α-D-glucopyranoside of the formula:

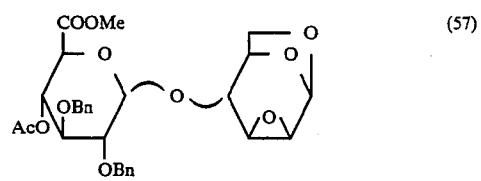

Figure 13:
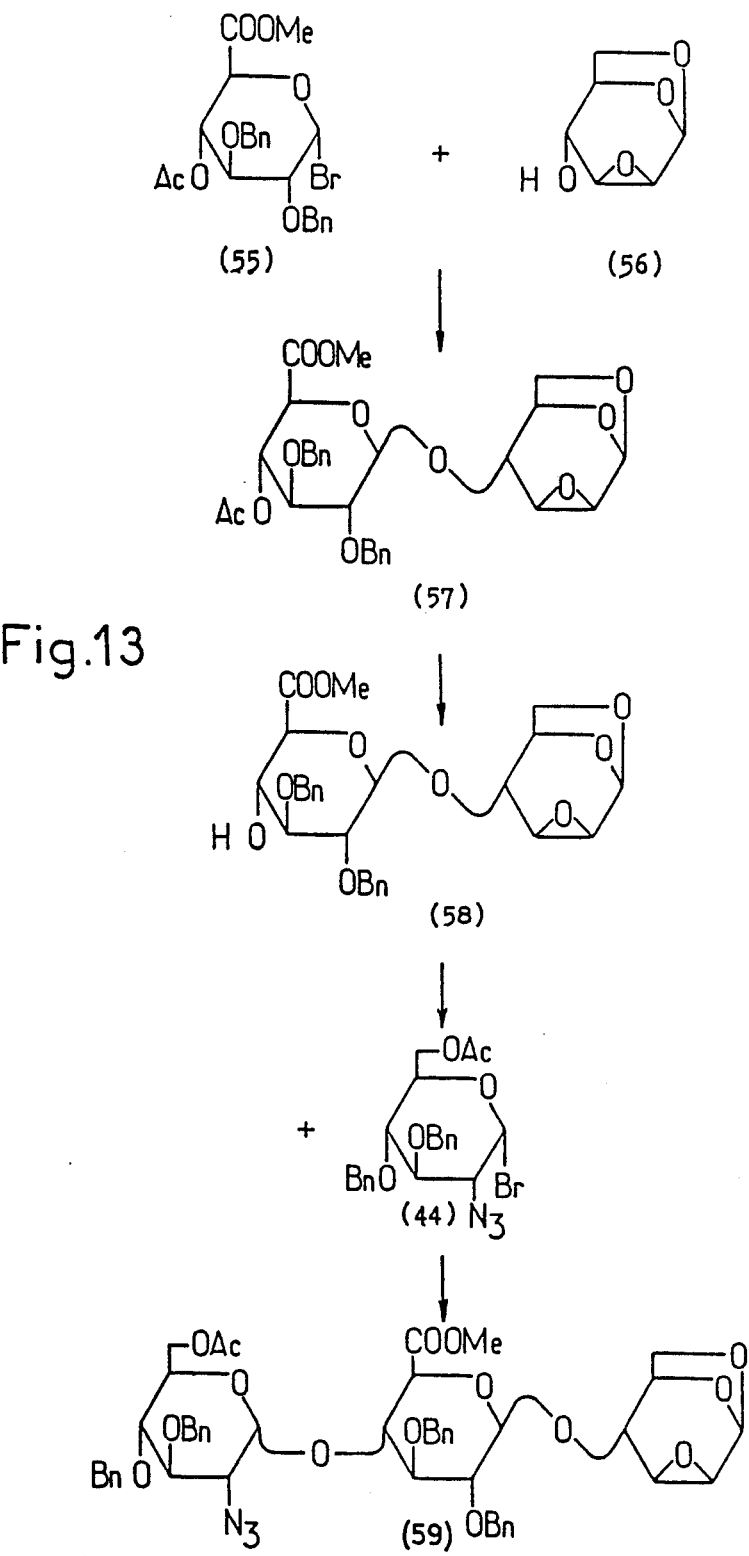
Figure 13A:
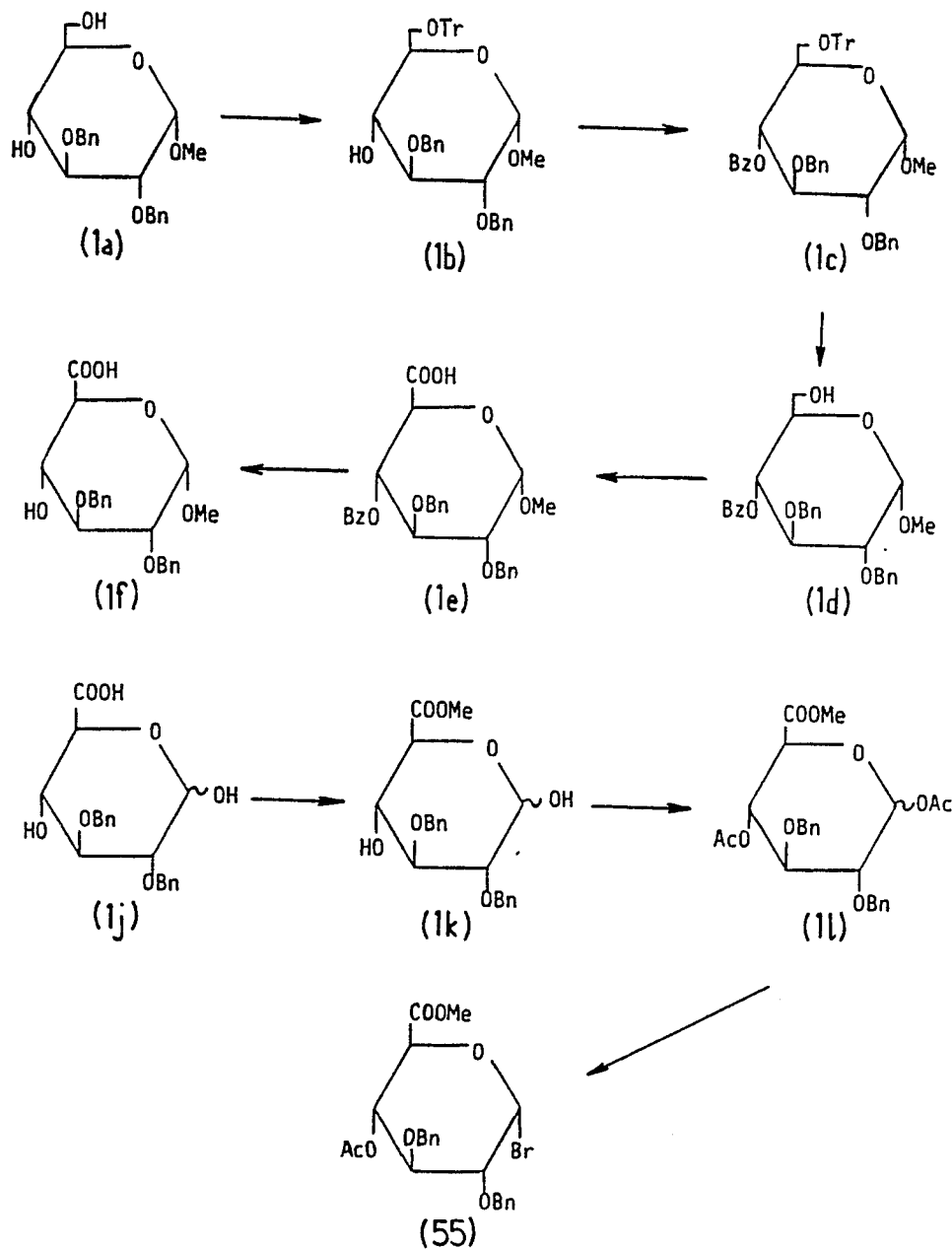
Figure 14:
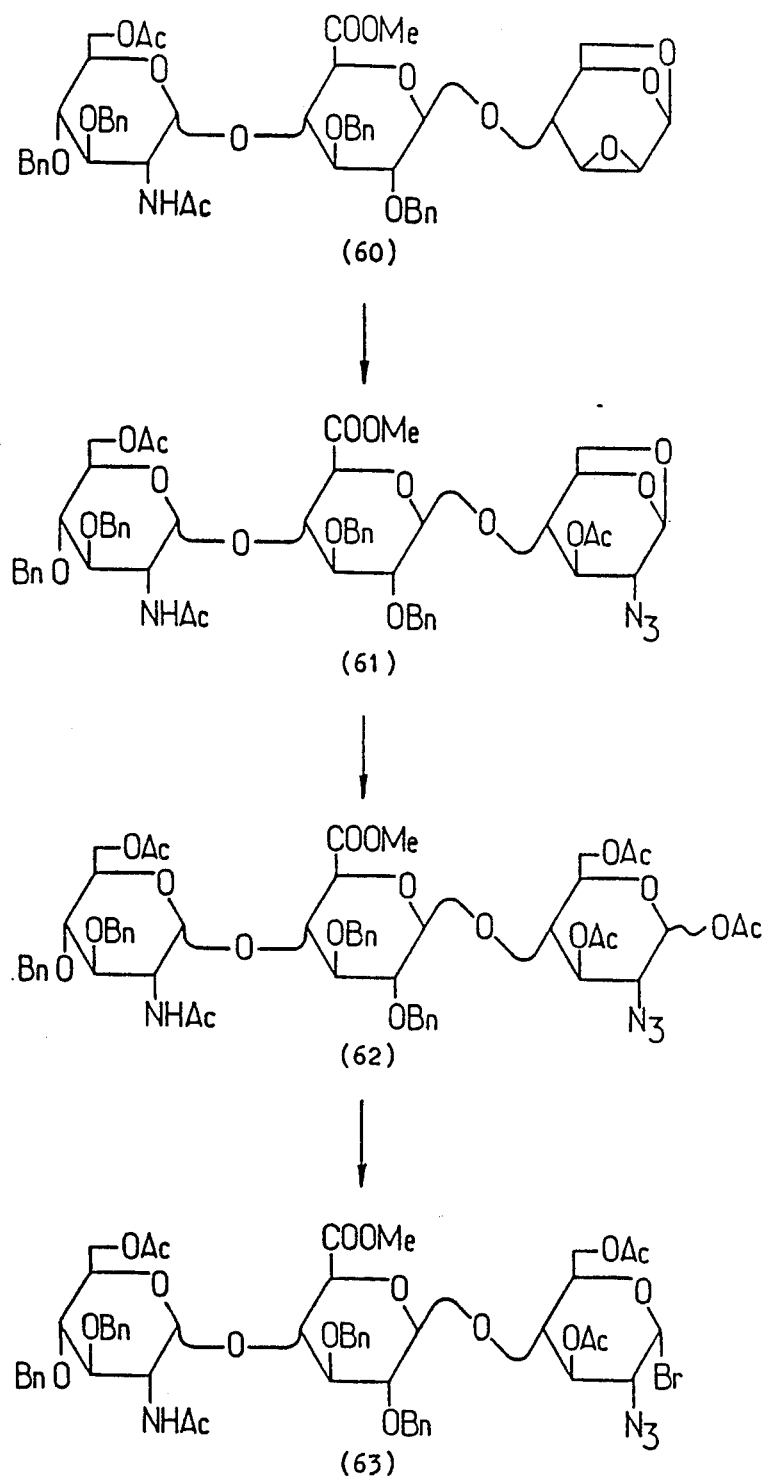

This synthesis is carried out from derivatives 55 and 56 (see FIG. 13).

(a) Preparation of methyl (bromo 2,3-di-O-benzyl-4-O-acetyl-D-glycopyranoside)uronate (compound 55)

SYNTHESIS OF COMPOUND 1d

To a solution of 1a (32 g; 85,5 mmoles) in pyridine (250 ml), is added trityl chloride (28, g; 1,2eq) and it is then heated to 80° C. A further addition of trityl chloride (4,6 g; 0,2 eq) is made after 3 hours of reaction. When the formation of 1b is complete (t.l.c. silica; methanol/chloroform, 1/20, v/v) the solution is cooled again to 0° C., then benzoyl chloride is added (15 ml; 1.5 eq). After one night, 1c is formed quantatively. Methanol (1.5 ml) is then added drop by drop to the reaction mixture and then concentrated to dryness. The residue obtained is taken up again in methanol (500 ml) reaction, the reaction mixture is transferred to a separating funnel containing ice water (21). The product 1d is extracted with chloroform then used as such in the following step.

A portion of this product was purified. Analysis of the IR spectrum confirms the structure. It is a colorless gum. $[\alpha]_D^{20} - 61°$ (chloroform).

SYNTHESIS OF THE COMPOUND 1j

The syrup obtained in the preceeding step (95 g) is disolved in acetone (1 l), then to the solution cooled to 0° C., is added drop by drop a solution of chromic oxide (52 g) in sulfuric acid 3.5M (220 ml). After 2 hours reaction, the reaction mixture is poured into ice water (1 l). The product 1e is extracted with chloroform (5×200 ml). The chloroform phase is washed until pH neutral, dried and concentrated to dryness.

To the residue obtained above, disolved in methanol (650 ml), is added drop by drop soda in aqueous phase is then (20 g in 50 ml), then the mixture is heated to 50° C. After one night, the solution obtained is partly concentrated, then poured into water (15 l). The aqueous phase is then washed with ether, then, after acidification with hydrochloric acid, the product 1f is extracted with ether. The ether phase is dried with sodium sulfate, then concentrated to dryness, giving a yellow mass (50 g) which contains 1e.

This residue (50 g) is dissolved in a mixture of acetic acid and trifluoroacetic acid (15/1, v/v, 615 ml). To this solution, stirred at 100° C., is added water (160 ml). After one night it is evaporated to dryness and the traces of acetic acid removed, and toluene evaporated, The residue formed in part from unhydrolised 1f and from 1g is dissolved in ether (400 ml).

To this solution, is added at 0° C., an ether solution of diazomethane until complete methylation (t.l.c. silica, etherhexane, 2/1, v/v). The excess diazomethane is then destroyed by acetic acid then the reaction mixture is concentrated to dryness.

The residue is purified on a silica gel column (200 g) eluted first with purechloroform, then by a chloroform-/ehter mixture, 3/1, v/v. In this way 1k is obtained (8.6 g; 22.2 mmoles, 26% with respect to 1a).

The derivative 1k is crystallised m.p. 122°–123° C. Elementary analysis and the NMR spectrum confirms its structure.

SYNTHESIS OF COMPOUND 1l

To a solution of 1k (3.9 g; 10 mmoles) in pyridine (50 ml), is added acetic anhydride (4 ml, 42 mmoles). After 2 hours, the reaction mixture is evaporated to dryness. In this way 1 is obtained (4.62 g; 98%).

SYNTHESIS OF COMPOUND 55

To a solution of 1l (1.4 g) in dichloromethane 30 ml and ethyl acetate (3 ml), is added titanium tetrabromide (1.5 g). The solution is stirred over-night at room temperature. After dilution with dichloromethane, reaction mixture is poured into iced water. The organic phase is washed with 5% bicarbonate in water, dried and concentrated. The residue is chromatographed on silica (50 g, ether/hexane, 1/1, v/v).

In this way the compound 55 is obtained (920 mg, 62%); it is a colourless syrup $[\alpha]_D^{20} = +97,5$ (c=1, chloroform). Elementary analysis and the NMR spectrum confirm the structure.

(b) A solution of the derivative 56 (432 mg, 3 mmoles) in dichloromethane (10 ml) is stirred at 0° C. in the presence of a 4 Å molecular sieve (0,5 g), drierite (1 g) and freshly prepared silver carbonate (0.42 g). After cooling to 0° C., is added, drop by drop, a solution of the compound 55 (490 mg, 1 mmole) in dichloromethane (6 ml). The reaction lasts two hours, the reaction mixture is then filtered. After evaporation to dryness and chromatography on silica gel of the residue, (solvent:ethyl acetate/chloroform, 1/6, v/v), the derivative 57 is obtained (285 mg; 51%).

The structure of derivative 57 is confirmed by its elementary analysis and its NMR spectrum. Rotary power: $[\alpha]_D^{20} = 39°$; chloroform; MP=156°–159° C.

EXAMPLE 13

Synthesis of the derivative 59, of the formula:

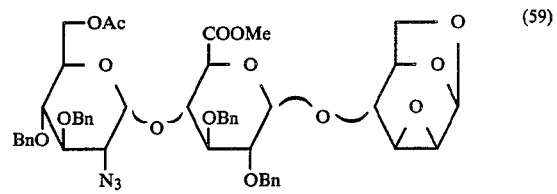

The trisaccharide 59 is prepared by the reaction of the disaccharide 58 (obtained by removal of the acetyl group at the 4 position of the compound 57 of Example 12), with the monosaccharide 44 by operating as follows (see FIG. 13):

Deacetylation reaction of the compound 57:

To a solution of the disaccharide 57 (260 mg) in methanol (25 ml), is added, at 0° C., a solution of 1N soda (25 ml). After one hour, the mixture is acidified by the addition of 1N hydrochloric acid (30 ml). The product is extracted with chloroform. After evaporation, the residue is crystallised in a ethyl acetate/hexane mixture. 167 mg are obtained (yield 70%) of the derivative 58.

Rotary power: $[\alpha]_D^{20} = -31°$; chloroform, MP=167°–170° C. The analysis found is correct. The structure of the derivative 58 is moreover confirmed by its NMR spectrum.

condensation of the disaccharide 58 with the monosaccharide 44:

To a solution of compounds 44 (300 mg) and 58 (155 mg) in dichloromethane (5 ml), are added successively 4 Å sieve in powder from (500 mg), then collidine (100 µl) and silver triflate. After 15 minutes, the solution is diluted with dichloromethane (50 ml), filtered, washed successively with water, a solution with 10% of acid potassium sulfate and with water. After drying and concentration, the residue is chromatographed on silica gel in an ethyl acetate/chloroform mixture (1/10, v/v). In this way the derivative 59 is obtained in the form of white foam.

This derivative 59 is characterised by its elementary analysis, its NMR spectrum and its rotatory power $[\alpha]_D^{20} = +25°$; chloroform).

EXAMPLE 13 A:

Synthesis of the trisaccharide of formula

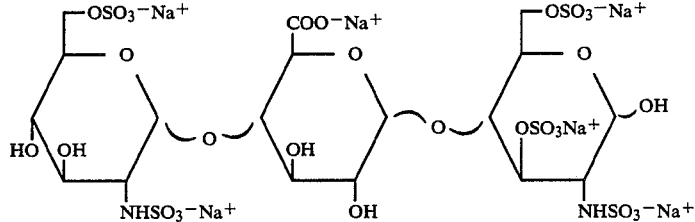

The monosaccharide 20 is reacted with methanol under the conditions described for the synthesis of tetrasaccharide EFGH above. In this way a β-methylglycoside is obtained. The MCA group is removed conventionally and then the disaccharide is subjected to the action of the monosaccharide 44 under the conditions described above for the development of the pentasaccharide.

The trisaccharide obtained is then subjected to conventional reactions for the purpose of protection and functionalisation. The structure is confirmed by the NMR spectrum.

EXAMPLE 14

Synthesis of the trisaccharide 62 of the formula:

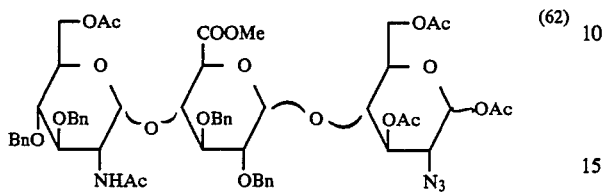

This trisaccharide 62 is prepared by the following steps (see FIG. 14):

(a) conversion of the N₃ group at 2 position of the glusosamine unit into an —NHAc group.

(b) opening of the 2,3 epoxy bridge of the unit at the reducing end.

(c) opening of the anhydro-1,6 bridge of the same unit.

(a) Passage from —N₃ to —NHAc:

To a solution of the derivative 59 (10 mg) in a mixture of DMF/ethanol (1/1:1 ml), are added the catalyst Pd/CaCO₃, 5% (5 mg). The suspension is stirred under hydrogen pressure of 1 atmosphere for 96 hours.

After filtration of the catalyst and evaporation, the residue is dissolved in methanol and acetylated by addition of a drop of acetic anhydride. The derivative 60 is obtained quantitatively.

The derivative 60 ischaracterised by its NMR specrum, its elementary analysis, its rotatory power: $[\alpha]_D^{20} = +35.5°$; chloroform.MP: 147°–149° C.

(b) Opening of the epoxy bridge:

The derivative is first saponified as indicated for the synthesis if the derivative 58, and this in order to remove the acyl group at the 6 position of the nonreducing terminal unit and the methyl-ester group at the position of the intermediate unit.

After extraction, the residue is disolved in DMF and is heated to 120° C., in the presence of sodium azide, for 48 hours. After evaporation, extraction with chloroform, washing with 0.1N HCl, with water, drying and evaporation of the solvent, a residue is obtained which is treated with diazomethane, then acetylated (pyridine acetic anhydride), giving thus the compound 61.

(c) Opening of the anhydro bridge:

The compound 61 is acetolysed under the usual conditions (acetic anhydride, sulfuric acid) at −20° C. After treatment of the reaction mixture, the derivative is obtained.

EXAMPLE 15

Synthesis of the derivative 63 of formula:

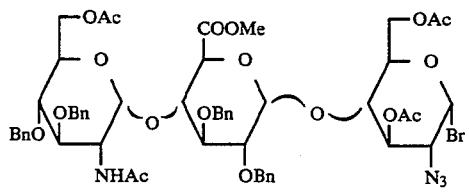

Treatment of the derivative 62 obtained in Example 14 with titanium tetrabromide in a solution of dichloromethane and ethyl acetate leads to the halogen 63 of which the structure is confirmed by its NMR spectrum. Its elementary analysis is correct (see FIG. 14).

EXAMPLE 16

Synthesis of the monosaccharide 68 or methyl 2-acetamido-3-6-di-O-benzyl-2-desoxy-α-D-glucopyranoside of the formula:

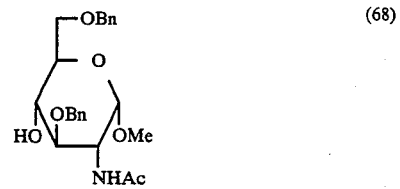

This synthesis was carried out in the following 4 steps from the monosaccharide 64 prepared by the technique of A. Neuberger, Journal of Chemical Society 1941, pages 50–51:

1. Benzylation of the —OH group at the 3 position,
2. Elimination of the benzylidene radical to liberate the —OH groups at the 4 and 6 positions,
3. Tosylation of the —OH GROUP at the 6 position,
4. Displacement of the —OTs group at the 6 position by a benzylate (see FIG. 15).

Step 1: benzylation reaction.

To a solution of the compound 64 (6.5 g, 20.10 mM) in dimethylformamide (120 ml), barium hydroxide octahydrate (3.6 g) and barium oxide (166 g), were added. After 10 minutes stirring at room temperature, benzyl bromide (4.5 ml) was added drop by drop. The reaction continued over-night. After dilution with chloroform (100 ml) the reaction mixture was filtered over Celite. The filtrate was concentrated to dryness, and in this way a white residue is obtained whose analysis by thin layer chromatography indicates that it contains a single substance, namely the derivative 65, which is used as such in the following step.

Step 2: removal of the benzylidene group.

The residue obtained above is disolved in a mixture of methanol (370 ml) and water (130 ml). To this solution, is added paratoluene sulfonic monohydrate (3 g), then the mixture is taken to reflux for one hour. After cooling, the major portion of the methanol was evaporated, then water (250 ml) was added. After washing with a small amount of chloroform (100 ml ) The aqueous phase was subjected to the following treatment:

(1) Precipitation of barium salts with sulfuric acid;
(2) Filtration of the barium sulfate formed;
(3) Removal of the excess of acid by means of an IRA resin 45 (OH⁻).

After removal of the resin and concentration, a slightly yellow residue (5.7 g) is obtained, namely the derivative 66. This derivative is employed as such in the preparation of the compound 67.

Step 3: Tosylation reaction.

This derivative 66 is disolved in a mixture of dichloromethane (150 ml) and DMF (10 ml). To this solution, is added tosyl chloride (5.6 g, 30 mM), then dimethylaminopyridine (121 mg) and finally triethylamine (5 ml). The reaction develops protected from moisture and under a dry nitrogen flow.

After 18 hours reaction, iced water is added and then the mixture is left with stirring for 14 hours approximately.

The reaction mixture was then diluted with dichloromethane and then the dichloromethane phase was washed successively with 2M hydrochloricacid, saturated sodium bicarbonate, then with water until pH neutral. After drying over sodium sulfate and filtration, the solvent was evaporated. The residue obtained was purified on a silica gel column (200 g) diluted with an ethyl acetate-hexane mixture (4/1, v/v).

The fractions containing the derivative 67 were grouped together.

After removal of the solvents, a solid residue is obtained (4.6 g) which is used directly in the synthesis of compound 68.

Step 4: benzylation reaction.

The derivative 67 obtained above is disolved in anhydrous dimethylformamide (50 ml). To this solution, is added a molar solution of sodium benzylate in benzyl alcohol (30 ml). The mixture is then heated to 90° C. for one hour. After cooling to room temperature, the mixture is then concentrated to dryness. It is then taken up again with chloroform (400 ml), the chloroform phase is washed with water, saturated sodium chloride, dried, then concentrated to dryness.

The residue is chromatographed on a silica gel column (200 g, chloroform/ethyl acetate, 1/1, v/v).

This way the derivative 68 is obtained (2.3 g). The yield with respect to compound 64 is 27.6%.

The compound 68 is crystalline, MP 149°-150° C., $[\alpha]_{20}^D = 87°$ (C=1, chloroform). Analysis of the infrared spectrum and elementary analysis confirm the expected structure for the product 68.

EXAMPLE 17

Figure 15:
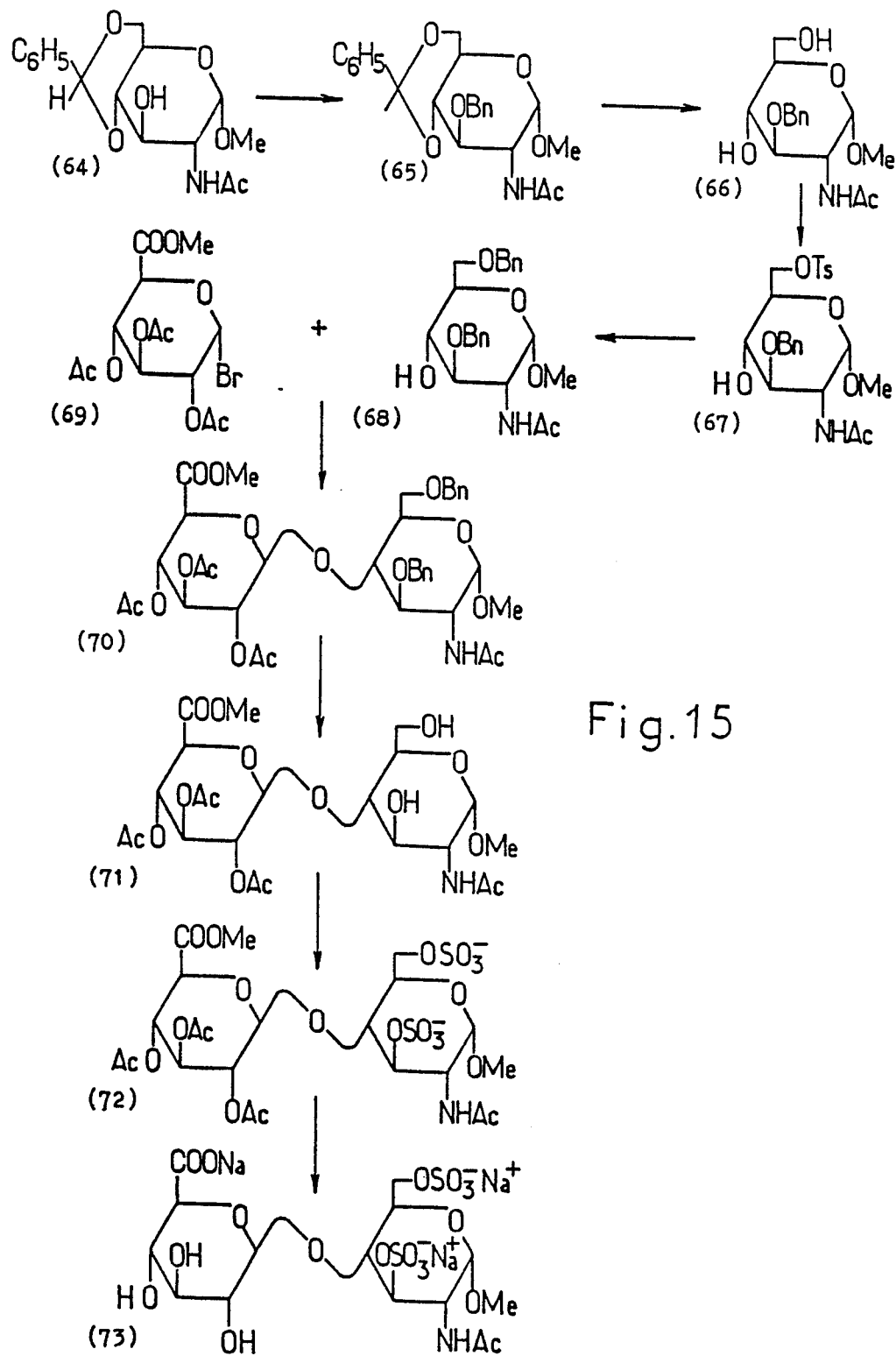

Synthesis of the disaccharide 73 (see FIG. 15).

This synthesis includes:

(1) Condensation of derivatives 68 and 69 leading to the disaccharide 70.

(2) Removal of the benzyl groups leading to the derivative 71.

(3) Sulfation of the —OH group of the derivative 71, leading to the derivative 72, followed by salification of the anionic groups and removal of the acetyl groups.

(1) Synthesis of the disaccharide 70.

This synthesis is carried out from the monosaccharides 68 and 69.

The halide is prepared by the technique of G. N. Bollenback Journal of American Chemical Society, 77 (1955), p. 3312.

To a solution of monosaccharide 68 (450 mg, 1.1 mM), in dichloroethane (30 ml) is added mercuric bromide (400 mg, 1 1 mM). After distillation of about 10 ml of dichloroethane, to the reaction mixture is added molecular sieves in powder (4 Å).

The halide 69 (1.1 g, 2.75 mM) in dichloromethane (10 ml) is then added. After distillation of 10 ml of dichoroethane, the reaction mixture is left to reflux for about 14 hours at a temperature of 90°-100° C. After cooling, the reaction mixture is diluted with dichloromethane (100 ml), then the solids are removed by filtration over pleated filters. The organic phase is washed with a solution of 10% potassium iodide (2×25 ml), then with a 5% solution of sodium bicarbonate (2×25 ml) and finally with water until pH neutral. After drying over sodium sulfate, filtration and concentration, the residue is purified on a silica gel c lumn (150 g) eluted, successively, with three acetone-ether mixtures (1/5 then 1/4, then 1/2, v/v).

In this way the disaccharide 70 is obtained pure (390 mg) in the form of crystals. MP=189°-190° C.; $[\alpha]_{20}^D = +60°$ (c=0.4 chloroform). The infrared spectrum, the same as the NMR spectrum and the elementary analysis confirm the expected structure.

(2) Synthesis of the disaccharide 71.

To a solution of the derivative 70 (100 mg) in methanol (20 ml), is added catalyst (Pd/C, 5%, 100 mg) and the suspension so obtained is stirred under hydrogen flow for three days.

The catalyst is then removed by filtration. After evaporation, a residue is obtained (73 mg, 97%) constituted by the disaccharide 71. The NMR spectrum confirms the expected structure of this compound.

It will be noted that the disaccharide 71 is the precursor of the basic unit of heparane-sulfate. It suffices to deprotect it to submit it to a saponification reaction, as reported below for producing the derivative 73 from the derivative 72.

(3) Synthesis of the disaccharide 73.

To a solution of compound 71 (70 mg) in dimethylformamide (2 ml), is added the sulfation agent (trimethylamide-sulfur-trioxide complex) (75 mg). After one night, a further addition of complex (35 mg) is made. After 6 hours, the reaction is terminated, the mixture is evaporated to dryness, taken up again with chloroform, neutralised with triethylamine and evaporated.

Chromatography on a silica gel column (20 g, methanol/chloroform, 1/2, v/v) enables isolation of the pure sulfated derivative 72 which is in the form of a white powder. This derivative is used directly in the synthesis of the deprotected disaccharide 73.

To a solution of the derivative 72 (71 mg) in methanol (9 ml), is added water (4 ml), then, drop by drop, a 1M soda solution (1 ml). After 4 hours stirring at room temperature, the reaction mixture is passed over an Amberlite IR 120 H+ column. The solution so obtained is neutralised and then salts are removed by passage over a Sephadex G25 column diluted with water. The fractions containing the sulfated disaccharide are grouped together.

After freeze drying, the derivative 73 is obtained in the form of a white powder (46 mg) $[\alpha]_{20}^D = 34.5°$ (c=1, water).

Conductimetric analysis indicates for this derivative a ratio sulfate/carboxyl equal to 2. Elementary analysis, the same as NMR analysis of carbon 13, confirm the expected structure for this product.

EXAMPLE 18

Synthesis of the compounds 75, 76 and 77 with a D-glucosamine structure (see FIG. 16).

Compound 75: Methyl 3-O-benzyl-4,6-O-benzylidene-2-benzyloxycarbonylamino-2-desoxy-α-D-glucopyranoside.

A solution of compound 74 (prepared according to Zu Yong Kyi, Sci. Sinica (Peking), 5(1956)461–467, CA 52 (1958)3694) (451 mg, 1 mM) in anhydrous N,N-dimethylformamide (10 ml) is stirred at room temperature protected from moisture for 5 h in the presence of anhydrous barytes (613 mg), barium hydroxide octahydrate (158 mg) and benzyl bromide (0.15 ml). The reaction mixture is then diluted with chloroform (50 ml), the organic phase is washed with 50% iced acetic acid, with water, dried (sodium sulfate), filtered and evaporated.

The solid residue is recrystallised in ethanol (461 mg, 91%); MP: 202°–203° C.; $[\alpha]_D = +46°$ (c: 1, chloroform).

Compound 76: Methyl-3-O-benzyl-2-benzyloxycarbonylamino-2-desoxy-α-D-glucopyranoside.

A suspension of the compound 76 (300 mg) in 60% acetic acid (10 ml) is stired at 100° C. for 30 min. The solution is then cooled, evaporated to dryness, evaporated with water (4×10 ml), The solid residue is dried under vacuum and recrystallised in 2-propanol to give the compound 76 (220 mg, 89%), MP: 151°–152° C., $[\alpha]_D = +94°$ (c: b 1, methanol)

Compound 77

Methyl 6-O-benzoyl-3-O-benzyl-2-benzyloxycarbocarbonylamino-2-desoxy-α-D-glucopyranoside A solution of compound 76 (835 mg, 2 mM) in a mixture of anhydrous pyridine (5 ml) and dichloromethane (12 ml) is stirred at room temperature protected from moisture in the presence of benzoyl cyanide (400 mg, 3 mM) for 5 h. The excess of reagent is then destroyed by the addition of methanol (5 ml) and stirring for 30 min. The reaction mixture is evaporated to dryness, evaporated with toluene and dried under vacuum. The solid residue is recrystallised in a ethyl acetate hexane mixture to give the compound 77 (935 mg) 90%) M.P.: 154°–155° $[\alpha]_D = +74°$ (c: 1, chloroform).

EXAMPLE 19

Synthesis of the compound 78 and 79 with L-iduronic acid structure (see FIG. 16)

Compound 78: 4-O-acetyl-3-O-benzyl-1,2-O-methoxyethylidene-β-L-methyl idopyranuronate.

A solution of bromide 36 obtained by Example 5, in step β (freshly prepared from 0.425 g, 1 mM, of a mixture of acetates (34 and 35) in anhydrous dichloromethane (10 ml) is stirred at room temperature under a dry argon atmosphere. Sym-collidine (0.66 ml, 5 mM) and anhydrous methanol (0.40 ml, 10 mM) are successively added, the reaction mixture is stirred 20 h under these conditions. After dilution with dichloromethane (50 ml), the organic phase is washed with a saturated aqueous solution of sodium hydrogenenocarbonate, with water, dried, (sodium sulfate), filtered and evaporated. The residue is chromatographed on a silica gel column (20 g). Elution by the mixture hexane:ethyl acetate (3:2 v/v, containing 0.5% of triethylamine) gives the compound 78 in the form of a pure syrup. (302 mg, 76% from acetates 34 and 35), $[\alpha]_D = -21°$ (c: 1, chloroform) NMR (CDCl$_3$):δ: 5.52(d, 1H, H-1, J$_{1,2}$: 3 Hz).

Compound 79: O-benzyl-1,2-O-tert-butoxyethylidene-β-L-methyl idopyranuronate

A solution of the orthoester 37 obtained in Example 5 in step γ (484 mg, 1.1 mM) in anhydrous methanol (15 ml) is cooled to −20° C. with stirring and in a dry argon atmosphere. Anhydrous potassium carbonate (60 mg) is added, and the reaction mixture is stirred 5 h under these conditions. The solids are drained, the filtrate evaporated and the residue taken up again in chloroform (50 ml). The organic phase is washed with iced water (three times) dried (sodium sulfate), filtered and evaporated. The residue is chromatographed rapidly on a silica gel column (25 g). Elution with a mixture hexane:ethyl acetate (2:1, v/v, containing 0.5% of triethylamine), gives, in order of elution:

The unsaturated compound 39 (31 mg, 7%) syrup, $[\alpha]_D = +103°$ (c: 1, chloroform), NMR (CDCl$_3$): δ: 6.27 (d.ded., 1H, H-4, J$_{3,4}$: 5 Hz, J$_{2,4}$: 1 Hz), 5.67 (d, 1H, H-1, J$_{1,2}$: 4 Hz).

A principal fraction (271 mg, 62%) which is crystallized in a hexane-ether mixture to give the compound 79 (123 mg, 28%), MP: 68°–69°; $[\alpha]_D = -19°$ (c: 1, chloroform), NMR (CDCl$_3$): δ:

In the course of chromatography on silica, and during the crystallisation tests of 79, a novel compound of Rf slightly higher than that of 79 appears. Chromatography on silica gel of the mother liquors from crystallisation of 79 enabled the isolation of some pure fractions of this novel compound 80 (41 mg, 11%), syrup, $[\alpha]_d = +21°$ (c: 1, chloroform), NMR (CDCl$_3$):δ: 5.83 (d, 1H, H-1, J$_{1,2}$: 4.5 Hz).

In the scope of the succession of synthesis envisaged according to the invention, in order to avoid the formation of 80, the crude syrup of 37 is not chromatographed, but used immediately for the following reaction:

EXAMPLE 20:

Preparation of the disaccharides 81, 82 and 83 (see FIG. 17)

Compound 81: Methyl 6-O-benzoyl-3-O-benzyl-2-benzyloxycarbonylamino-2-desoxy-4-O-(2,4-di-O-acetyl-3-O-benzyl-α-L-methyl idopyranuronyl)-α-D-glucopyranoside.

A solution of the orthoester 78 (80 mg, 0.2 mM) obtained in Example 19 and the alcohol 77 (52 mg, On1 mM) obtained in Example 18 in anhydrous chlorobenzene (8 ml) is heated to 140° C. with stirring and a slight flow of dry argon. After slow distillation of 6 ml of solvent, a solution of 2,6 dimethyl pyridinium perchlorate (0.002 mM freshly prepared according to N. K. Kochetox, A. F. Bochkov, T. A. Sokolovskaia and V. J. Sntatkova, Carbonhdr. Res., 16 (1971) 17–27, in chlorobenzene (2 ml) is added, drop by drop, in 15 min. with simultaneous distillation of solvent (2 ml). The reaction mixture is then stirred for 1 h, under these conditions, with the addition of fresh solvent (10 ml) and simultaneous distillation so that the reaction volume remains constant and equal to 2 ml. After cooling and dilution with chloroform, the organic phase is washed with saturated sodium hydrogenocarbonate solution, with water, dried (sodium sulfate), filtered and evaporated. The residue is chromatographed on a silica gel column (15 g). Elution by the mixture hexane:ethyl acetate (4:3, v/v) gives, in order of elution:

the starting substance 77 (20 mg, 38%), a homogeneous fraction in thin layer chromatography (54 mg). The NMR spectrum of this fraction shows the presence of several O-methyl (δ: 3.35–3.50) signals due to the methyl glycosides derived from the rearrangement of the orthoester 78. This fraction is crystallized in an ethanol-water mixture and recrystallised in a ethyl acetate hexane mixture to give 81 (44 mg, 50%), MP: 120°–121° C., $[\alpha]_D = +17°$ (c: 1, chloroform), NMR (CDCl$_3$): in accordance with the expected structure.

Compound 81: Methyl 6-O-benzoyl-3-O-benzyl-2-benzyloxycarbonylamino-2-desoxy-4-O-(2-O-acetyl-3-O-benzyl-4-O-chloroacetyl-α-L-methyl idopyranuronyl)-α-D-glucopyranoside.

A solution of the orthoester 38 (120 mg, 0.25 mM) obtained in Example 5 and the alcohol 77 (66 mg, 0.125 mM) in anhydrous chlorobenzene (8 ml) is heated to 140° C. with stirring and a slight flow of dry argon. After slow distillation of 6 ml of solvent, a solution of 2,6-dimethylpyridinium perchlorate (0.0025 mM) in chlorobenzene is added drop by drop in 15 min. with simultaneous distillation of solvent (2 ml). The reaction mixture is stirred for 1 h and then treated under the conditions described for the preparation of 81. The residue is chromatographed on a column of silica gel (15 g). Elution with the mixture hexane:ethyl acetate (7:4, v/v) gives, in order of elution:

the product 77 (40 mg, 60%), the disaccharide 82, crystallized in a ether-hexane mixture, (26 mg, 30%), MP: 143°-144° C., $[\alpha]_D = +$(c: 1, chloroform), N.M.R. (CDCl$_3$): in accordance with the expected structure.

Compound 83: O-dechloroacetylation and acetylation of the disaccharide 82.

A mixture of the disaccharide 82 (12 mg) and of thiourea (5 mg) in pyridine (1.2 ml) and absolute ethanol (0.3 ml) is stirred at 100° C. for 30 min. After cooling, the reaction mixture is evaporated to dryness and the residue is taken up again with a water-chloroform mixture (1:1, v/v, 20 ml). The organic phase is washed with water, dried (sodium sulfate), filtered and evaporated. The residue is washed on a silica gel column (1 g). Elution with the mixture ethyl acetate:hexane (1:1, v/v) gives the disaccharide 83 (3 mg) in the form of a pure syrup which has not been analysed, but acetylated immediately (pyridine:acetic anhydride 2:1, v/v, 1.5 ml). After 15 h at ambient temperature, the reaction mixture is evaporated to dryness and the residue is applied to a silica gel column (0.5 g). Elution by the mixture ethyl acetate:hexane (1:1, v/v) gives the disaccharide 81 (7 mg), crystallized in an ether-hexane mixture MP: 120°-120.5° C., MP of the mixture with 81: 120°-121° C.

EXAMPLE 21

Figure 18:
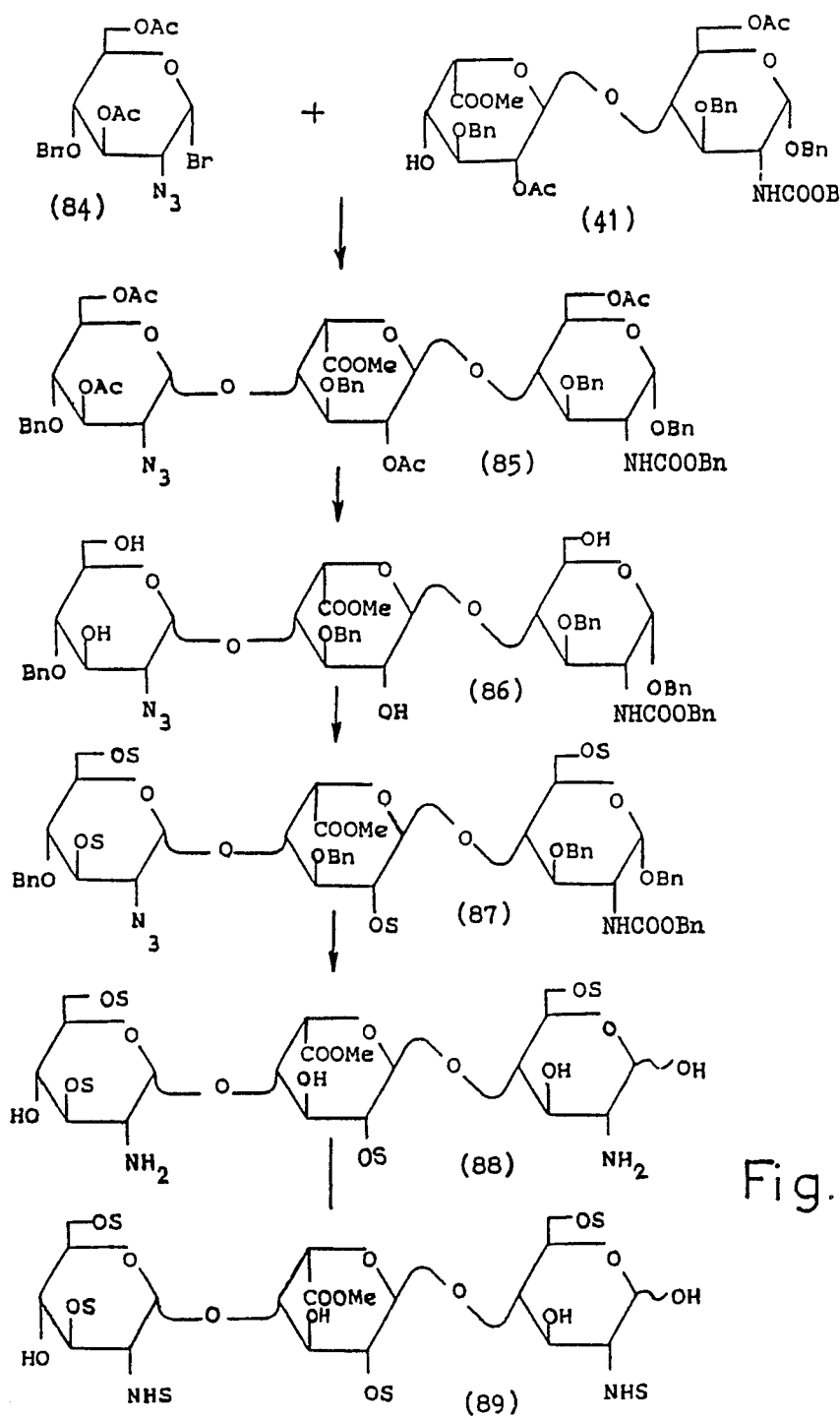

Synthesis of the trisaccharide 85 (see FIG. 18).

A solution of the bromide 84 (prepared according to H. PAULSEN and W. STENZEL, Chem. Ber 111 (1978) 2334-2347, 110 mg, 0.25 mM) and of the alcohol 41 (prepared according to Example 6, 113 mg, 0.13 mM) in anhydrous dichloromethane (2.5 ml) is stirred protected from light under a dry argon atmosphere in the presence of a 4 Å molecular sieve (powder 100 mg) for 30 min. After cooling to 20° C., symcollidine (70 μL, 055 mM) and silver triflate (78 mg, 0.30 mM) were added successively and stirring was maintained under these conditions for 2 hours. The reaction mixture was then diluted with dichloromethane (50 ml), the solids were drained, and the filtrate was washed with 0.1M solution of iced hydrochloric acid with water, with a saturated aqueous sodium hydrogencarbonate solution, with water, dried (sodium sulfate), filtered and evaporated.

The residue was chromatographed on a silica gel column (18 g). Elution by the mixture hexane:ethyl acetate (4:3, v/v) gives the trisaccharide 85 in the form of a colorless glass which it has not been possible to crystallize (139 mg, 88%); $[\alpha]_D = +83°$ (cl, chloroform); NMR spectrum (90 Mhz, CDCl$_3$): δ: 7.25 (m, 25H, 5Ph.); 5.44 (d. de d., 1H, H$_3''$, J$_2''$ $_3''$: 10.5 Hz, J$_3''$, $_4''$: 9 Hz); 5.26 (d, 1H, H$_1''$, J$_1''$, $_2''$ $_3''$: 3.5 Hz); 3.59 (s, 3H, COOMe); 3.06 (d. de d., 1H, H$_2''$, J$_1''$, $_2''$: 3.5 Hz, J$_2''_3''$: 10.5 Hz); 2.12, 2.08, 2.01 and 1$^2$.97 (4s, 12H, 4 OAc).

EXAMPLE 22

Synthesis of the trisaccharide 89 (see FIG. 18)

By the four following steps:
(a) removal of the acetyl groups,
(b) sulfation,
(c) hydrogenation,
(d) sulfation of the amino functions (a) Removal of the methyl groups leading to the trisaccharide 89:

A solution of trisaccharide 85 (122 mg) in a mixture of 1,2-dimethoxyethane (6 ml) and methanol (2 ml) is stirred at 0° C. An aqueous 1M solution of soda (2 ml) is added drop by drop in 10 Min and the reaction mixture is stirred 6 hours at 0° C. 1M hydrochloric acid is then added drop by drop until pH=0 (appearance of a white precipitate). The mixture is poured into ice water (100 ml) and extracted with chloroform (5 times 10 ml). The organic phases are washed with ice water, dried (sodium sulfate), filtered and evaporated. The syrupy residue is dissolved in methanol (2 ml) and treated with an ether solution of diazomethane until persistance of the yellow color. After 30 min., the reaction mixture is evaporated to dryness. The residue is chromatographed on a silica gel column (10 g). Elution by the mixture ethyl acetate/hexane (2:1, v/v) gives the trisaccharide 86 in the form of a colorless foam which it has not been possible to crystallize (85 mg 81%); $[\alpha]_D = +77°$ (cl, chloroform), NMR spectrum (90 MHz, CDCl$_3$): absence of OAc signals (towards δ=2 ppm). Elementary analysis: in accordance with the structure sought.

(b) Sulfation leading to the trisaccharide 87

To a solution of the derivative 86 (41 mg) in DMF (2 ml) is added the complex trimethylamine/sulfur trioxide (TMA/SO$_3$; 60 mg; 2.5 equivalents per OH). After one night at 50° C., the reaction is complete. Methanol (0.5 ml) is added and then the solution is placed on a Sephadex LH-20 column (1.5×25 cm) equilibrated in a chloroform/methanol mixture (1:1; v/v). Elution by the same mixture enables the product of the reaction to be separated from the excess of reagent and from the reaction solvent. The residue obtained is bhromatographed on a silica gel column (10 g), eluted by an ethyl acetate/pyridine/acetic acid/water mixture (98:56:13:32; v/v/v/v). The pure product obtained is dissolved in methanol, then passed through a Dowex 50W×4, Na+ (5 ml) resin column. After evaporation and drying, the derivative 87 (58 mg, 100%) is obtained. It is homogeneous in tlc (ethyl acetate/pyridine/acetic acid/water; 5:5:1:3; v/v/v/v and ethyl acetate/methanol/acetic acid; 7:3:0.1: v/v/v).

$[\alpha]_D^{20} = +55°$ (methanol). The NMR spectrum is compatible with the structure sought.

(c) Hydrogenation leading to the trisaccharide 88.

A solution of the compound 87 (20 mg) in a mixture of methanol (2 ml) and water (0.5 ml) is stirred for 96 hours at a hydrogen pressure of 0.2 bar, in the presence of 5% Pd/C (20 mg). The catalyst is then removed by filtration. Ultra-violet analysis confirms the absence of aromatic nuclei. After evaporation, the product is employed in the synthesis of the trisaccharide 89.

(d) Sulfation leading to the trisaccharide 89.

The derivative 88 obtained previously is dissolved in water (2 ml). The pH of the solution is adjusted to 9.5 then it is kept at this value by means of a pH-stat. The complex TMA/SO$_3$ (14 mg; 5 eq./NH$_2$). After one night, the same amount of complex is added. After 48 hours, the pH is brought to 12 by means of 2M soda, then it is kept at this value for 2 hours. After neutralization with hydrochloric acid, the reaction mixture is chromatographed on a Sephadex G-25 column, eluted with water. The compound 89 is detected by a color reaction with carbazole, characteristic of uronic acids (Bitter et Muir, *Anal. Biochem.* 4 (1962) 330–334). These fractions containing 89 are groups together and passed through a Dowex resin column 50W×4, Na+eluted with water. After freeze-drying, 89 is obtained (4.5 mg).

Colorimetric analysis of the glucide constituents gives 2.55 mole of uronic acid per 5.15 moles of glucosamine (ratio ½).

The NMR spectrum of this product confirms the structure (sequence, anomerism of the linkages, substitutions by sulfates).

EXAMPLE 23

Synthesis of the disaccharide 92 of the formula

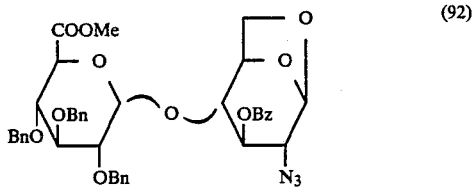

(92)

Reference will be made of FIG. 19

The product 91 (1 g), in solution in dichloromethane (50 ml), is stirred in the presence of drierite (6 g) and freshly prepared silver carbonate (4.5 g), for 1 hour in an argon atmosphere. Then the halide 90 (2.8 g) dissolved in dichloromethane (10 ml) is added, after 1½ hours 2.8 g of the halide 90 is again added. After one night the solids are removed by filtration and the residue obtained after evaporation of the solvents is purified on a silica column in the solvent ethyl acetate/chloroform (1/30; v/v).

In this way the product 92 is obtained (866 mg; yield 42%). It is crystallised in a hexane/ethyl acetate mixture.

MP: 104°–106° C.; $[\alpha]_D^{20}=0°$ (c=1; chloroform).

Elementary analysis and the NMR spectrum are in agreement with the desired structure.

EXAMPLE 24

Synthesis of the derivative 94 of the formula

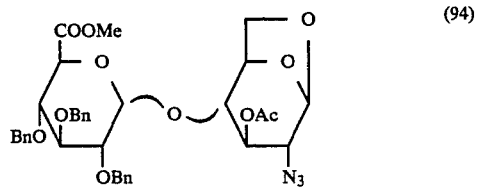

(94)

Figure 19:
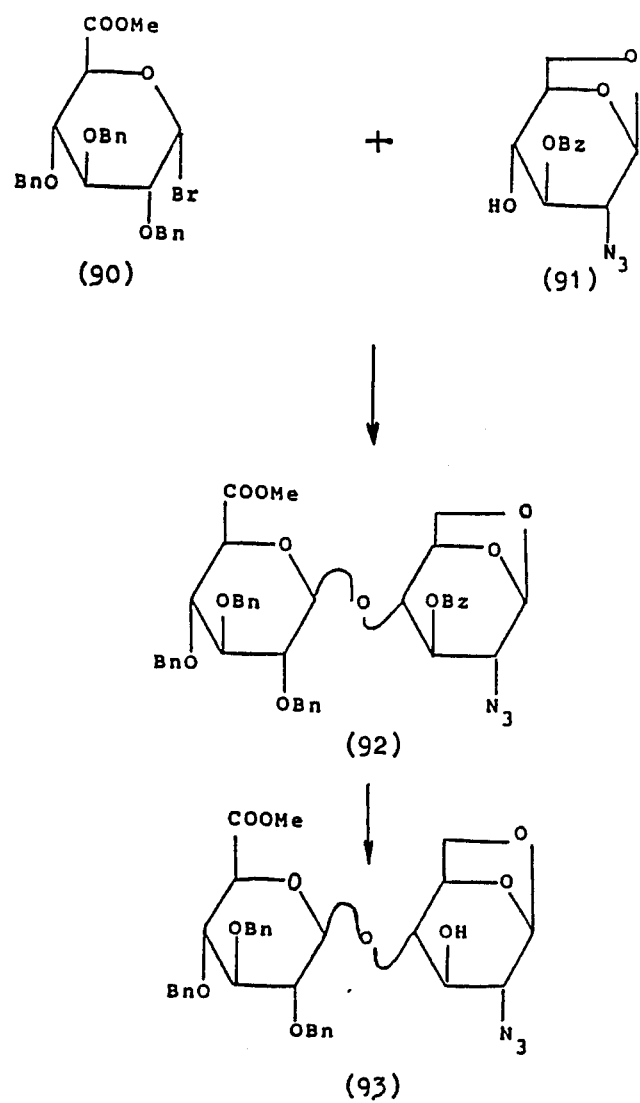

Reference will be made to FIGS. 19 and 20.

The derivative 92 (1.5 g) is dissolved in a mixture of chloroform and methanol (1/1; v/v). Then 2 ml of sodium methanolate is added (2M in methanol). After 20 minutes, the solution is neutralized by addition of Dowex 50 resin leading to the derivative 93 which is not isolated. After filtration and evaporation, conventional methylation by diazomethane in ether enables the fraction of carboxylic acid possibly liberated to be reesterified. After evaporation the residue is treated with a mixture of pyridine (20 ml) and acetic anhydride (2 ml) over night. After evaporation, the residue is crystallized in ethyl acetate/hexane giving the product 94 (1.125 g; yield 81.6%).

M.P.: 103°–105° C.; $[\alpha]_D^{20}=+5.2°$ (c=1; chloroform).

Elementary analysis and the NMR spectrum are in agreement with the desired structure.

As a modification, the derivative 94 is prepared by operating as described above but by employing the derivative 95 instead of the derivative 91.

EXAMPLE 25

Synthesis of the derivative 97 (see FIG. 20)

In a first step, opening of the anhydride bridge is carried out; then in a following step, a bromination reaction is carried out.

1. Opening the 1,6-anhydro bridge.

The compound 94 (1 g) is dissolved in acetic anhydride (10 ml) then cooled to −20° C. under argon. To the cold solution is added concentrated sulfuric acid (100 μl). After 30 minutes, the reaction mixture is diluted with chloroform (150 ml) then poured into an aqueous sodium bicarbonate solution (26.5 g in 400 ml). After the release of gas the chloroform phase is washed twice with a saturated solution of NaCl then dried and concentrated. After chromatography on silica (50 g) in a mixture of ethyl acetate and chloroform 1/20 v/v, the compound 96 is obtained (995 mg; yield 86.7%).

This compound is in the form of a white foam.

The spectrum and elementary analysis confirm the production of the desired structure.

2. Bromination

To titanium tetrabromide (213 mg) is added a solution of the derivative 96 (0.2 g) in dichloromethane/ethyl acetate (9/1; v/v 4 ml). After one night with stirring followed by dilution with dichloromethane, it is poured onto a mixture of water and ice (50 ml), and then washed with two times 50 ml of ice water. After drying and evaporation the syrup obtained is chromatographed on silica in the solvent ethyl acetate/chloroform 1/20; v/v. In this way the derivative 97 is obtained with a yield of 25 to 50%.

NMR spectrum: (ppm, CDCl₃): 2.04; 2.11:2 singlets of 3 protons 2-OAc; 3.7:1 singlet of /protons COOMe; 6.33:1 doublet of 1 proton H₁; $J_{1,2}=3.5$ Hz.

EXAMPLE 26

Synthesis of the tetrasaccharide 98 (see FIG. 20)

A solution of bromide 97 (50 mg, 60M) and alcohol 41 prepared by Example 6 (43 mg, 50 μm) in anhydrous dichloromethane (1 ml) is stirred protected from light in a dry argon atmosphere in the presence of a molecular sieve 4 Å (powder, 100 mg) for 15 minutes. After cooling to −10° C., sym-collidine (11 μl, 80 μM) and silver trifluoromethanesulfonate is added (Ag triflate, 18 mg, 70 μM) successively, and stirring is maintained under these conditions for 3 hours. The reaction mixture is then diluted with dichloromethane (30 ml), the solids are drained, and the filtrate is washed with an 0.1M solution of iced hydrochloric acid, with water, with a saturated aqueous solution of sodium hydrogencarbonate, with water, dried (sodium sulfate), filtered and evaporated.

The residue is chromatographed on a silica gel column (7 g). Elution by the mixture hexane-ethyl acetate (4:3, v/v) gives 56 mg of tetrassacharide 98 (yield 70%)

in the form of a colorless glass which it has not been possible to crystallize.

Characteristics of the NMR spectrum: (270 MHz, CDCl$_3$): δ: 7.25 (m, 35 H, 7 Ph); 5.35 (d.ded., 1 H, H$_3''$ J$_2''$, $_3''$: H$_z$, J$_3''$, $_4''$ 0 Hz; 5.27 (d., 1H,H$_1'''$ J$_1''$, 2'': 3.5H); 5.31 (d., 1H, H$_1'''$ J$_1'''$ $_2'''$: 7.5 H$_z$); 3.68 (s, 3H, COOMe IDO); 3.59 (s, 3H, COOMe gluco); 3.37 (d.de d., 1H, H$_2'''$ J$_1'''$, 2''': 7.5 H$_z$, J$_2'''$3''': 9.5H$_z$) 3.18 (d.de d., 1H, H$_2''$, J$_1''$,$_2''$: 3.5 H$_z$, J$_2''$, $_3''$: 11 Hz); 2.06 AND 1.97 (2s, 9 and 3 H, 4 OAc).

This spectrum is reported in FIG. 33.

EXAMPLE 27

Figure 21:
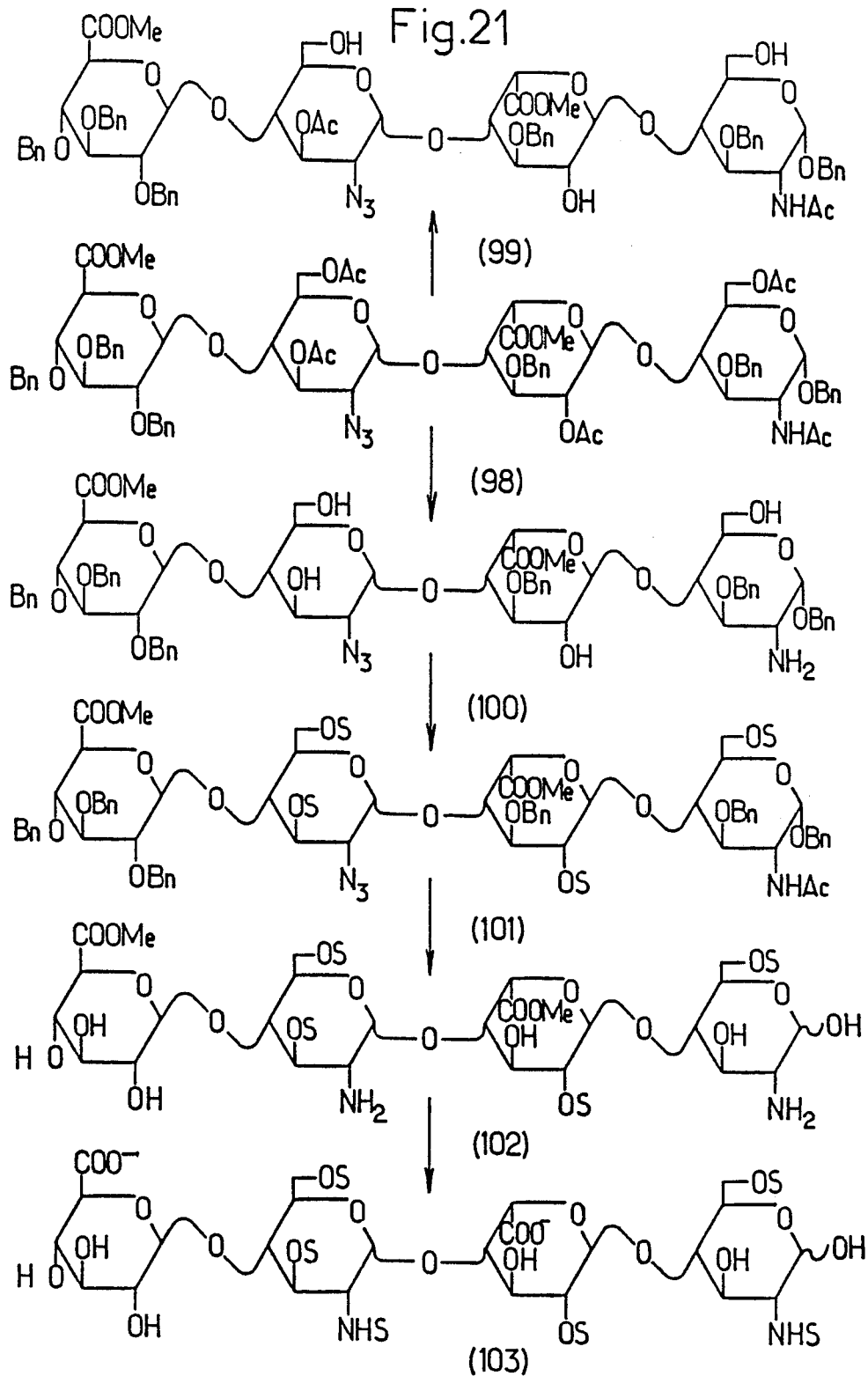

Synthesis of the tetrasaccharide 99 (see FIG. 21)

A solution of tetrasaccharide 98 (28 mg) in anhydrous methanol (3 ml) is cooled to −15° C. under a dry argon atmosphere. Anhydrous potassium carbonate (12 mg) is added and the mixture is stirred 6 hours under these conditions. the solids are then drained, the filtrate was evaporated and the residue is taken up again with chloroform (15 ml). The organic phase is washed with a saturated aqueous solution of sodium chloride, washed with water, dried (sodium sulfate), filtered and evaporated.

The residue is chromatographed on a column gel (2 g). Elution with ethyl acetate/hexane (3:2, v/v) gives the tetrasaccharide 99 in the form of a colorless glass (22 mg, 85%).

NMR spectrum (270 MHz, CDCl$_3$): δ: 7.30 (m, 35H, 7Ph); 5.37 (d, 1H, H$_1''$, J$_1''$, 2'': 3.5 Hz); 5.29 (d. de d., 1H, H$_3''$, J$_2''$, 3'': 10 Hz, J$_3''$, 4'': 8.5 Hz); 5.09 (d, 1H, H$_1$, J$_{1,2}$: 3.5 Hz); 3.57 (s, 3H, COOMe ido); 3.43 (s, 3H, COOMe gluco); 2.06 (s, 3H, OAc), This compound 99, which is a derivative mono-O-acetylated (at the 3 position on the 2nd unit) of the tetrasaccharide 103 is a potential intermediate for the synthesis of an analogue of this tetrasaccharide which will not be sulfated at the 3 position of the second unit.

EXAMPLE 28

Synthesis of the tetrasacchride 103 (see FIG. 21)

The following steps (a) to (d) are resorted to:
(a) removal of the acetyl groups,
(b) sulfation,
(c) hydrogenation,
(d) sulfation of the amino groups, (a) removal of the acetyl groups resulting in the derivative 103:

A solution of the tetrasaccharide 98 (40 mg) in a mixture of 1,2-dimethoxyethane (3 ml) and methanol (1 ml) is cooled to −15° C. An M aqueous solution of soda (1 ml) is added drop by drop in 10 min.; the reaction mixture is stirred 5 hours at 0° C. M hydrochloric acid is then added drop by drop to pH=0 and the mixture is poured into ice water (50 ml). After extraction with chloroform (5 times 5 ml), the organic phases are washed with water, dried (sodium sulfate) filtered and evaporated.

The residue is dissolved in methanol (1 ml) and treated with an ether solution of diazomethane until persistance of the yellow colour. After 30 min. the reaction mixture is evaporated to dryness. The residue is chromatographed on a silica gel column (3 g). Elution by the mixture ethyl acetate/hexane (2:1, v/v) gives the tetrasaccharide 100 (27 mg, 75%); MP 126°–127° C. (ethanol); [α]$_D$=+55° (cl, chloroform). NMR spectrum (90 MHz, CDCl$_3$): total absence of signals OAc (towards δ=2).

Elementary analysis: in accordance with the desired structure.

(b) Sulfation leading to the derivative 101.

To a solution of the derivative 100 (2.4 mg) in DMF (1 ml) is added the complex TMA/SO$_3$ (24 mg.). After one night at 50° C., the sulfation reaction is complete.

Methanol (0.5 ml) is added to the reaction mixture and then the latter is deposited on a Sephadex LH-20 column equilibrated in chloroform methanol (1:1, v/v). The fractions containing 101 are grouped together. After evaporation to dryness, the residue is chromatographed on silica gel (10 g) in the mixture ethyl acetate/pyridine/acetic acid/water (160:77:19:42; v/v/v/v). The pure fractions are grouped together. After concentrating to dryness, the residue is passed through a Dowex 50 W×4, Na+ column eluted with water. The product obtained (30 mg) is homogeneous in thin layer chromatography in the above solvent. Its NMR spectrum confirms the structure. [α]$_D^{20}$=+39° (1, methanol).

(c) Hydrogenation leading to the derivative 102.

A solution of the derivative 101 (10 mg) in a mixture of methanol (1.8 ml) and water (0.2 ml) is stirred under hydrogen pressure of 0.2 bar in the presence of 5% Pd/C (10 mg). After 96 hours, the catalyst is removed by filtration. Ultra-violet analysis confirms the absence of aromatic rings. After evaporation, the derivative 102 is used as such for the preparation of the derivative 103.

(d) Sulfation leading to the derivative 103.

The derivative 102 obtained in the preceeding step, is dissolved in water (2 ml). The pH of this solution is adjusted to 9.5; it is kept to this value through-out the sulfation. The complex TMA/SO$_3$ (14 mg) is added. A second addition is made after 24 hours (14 mg). After 48 hours, the pH is brought to 12, then to 7 two hours later. The reaction mixture is then chromatographed on a Sephadex G-25 column (50 ml). The fractions containing the derivative 103 (detection by colour reaction of the uronic acids) are grouped together, passed through a Dowex 50 W×4 Na+ resin column then lyophilised. In this way the tetrasaccharide 103 (2 mg) is obtained.

Colorimetric analysis of the constituents of the derivative 103 gives 1.84 moles of glucosamine for 2.06 uronic acid moles.

The structure of derivative 103 (sequence, anomerism, position of the sulfate groups) is confirmed by the NMR spectrum (270 MHz, TMS): δ for the anomeric protons respectively of the 1st, 2nd, 3rd and 4th units, 4.72; 5.30; 5.55; and 5.67.

EXAMPLE 29

Figure 22:
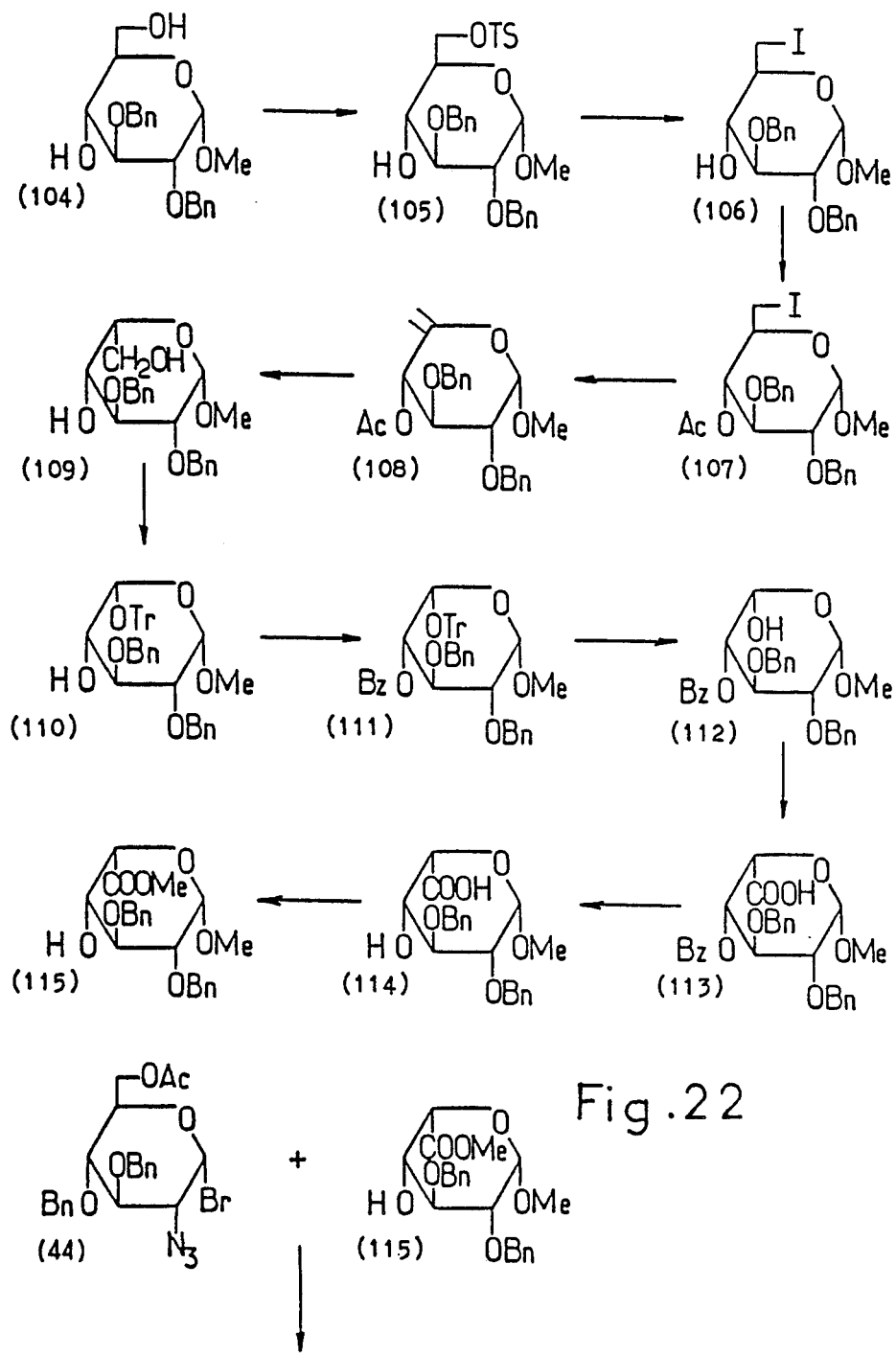

Synthesis of the monosaccharide 115 (see FIG. 22).

This synthesis is carried out by the following steps 1 to 7.

Step 1: synthesis of the monosaccharide 105

This monosaccharide is prepared from the compound 104 obtained by the technique of N. L Holder and B. Fraser-Reid, Canadian Journal of Chemistry, 51 (1973) page 3357. To a solution of the compound 104 (1 g, 12.67 mM) in dichloromethane (20 ml), is added tosyl chloride (0.55 g), then dimethyllaminopyridine (16 mg) and finally triethylamine (0.7 ml). After stirring under a flow of nitrogen protected from moisture, for about 14 hours, the reaction is stoped by the addition of ice and water. After dilution of the reaction mixture with dichloromethane (50 ml), the dichloromethane phase is washed with 2M hydrochloric acid, then a saturated solution of sodium bicarbonate, and finally with water until pH neutral. After drying and evaporation, a residue is obtained, namely the derivative 105 (1.4 g, 97%) which is used as such in the synthesis of the derivative 106.

Step 2: Synthesis of the derivative 106.

The monosaccharide 105 (31.8 g) and sodium iodide (39 g) are dissolved in acetonitrile (250 ml), then the solution is brought to reflux for 3 hours. After cooling the reaction mixture, the white precipitate formed is filtered. The filtrate is concentrated, the residue is taken up again with chloroform, then the chloroform phase is washed with water until pH neutral, dried over sodium sulfate and concentrated to dryness. A syrup is obtained which is chromatographed on a column of silica gel (200 g, ether-hexane, 1/1, v/v). In this way the iodised derivative is obtained (24.7 g, 71.5%). $[\alpha]_{20}{}^D = 24°$ (1, chloroform). The infra-red spectrum, the NMR spectrum and elementary analysis confirm the structure of 106.

Step 3: synthesis of the derivative 107.

To a solution of the derivative 106 in anhydrous pyridine (200 ml), is added acetic anhydride (43 ml). After about 14 hours stirring, the reaction is terminated The reaction mixture is concentrated to dryness, then the residue is purified on a silica gel column, under pressure, in an ethyl acetate/hexane solvent (1/6, v/v). The pure fractions are grouped together. In this way the product 107 is obtained (16.4 g, 70%). This product is in the form of a syrup. $[\alpha]_{20}{}^D = +4.5°$ (1.3, chloroform). Elementary analysis as well as analysis of the infrared spectrum confirm the structure.

Step 4: synthesis of the derivative 108.

To a solution of the derivative 107 (4 g) in pyridine (100 ml), cooled to 0° C., is added silver fluoride (AgF, 6.9 g). After two and one half hours, the reaction mixture is poured into a mixture containing chloroform and ether (1/4, v/v, 1 l). The suspension obtained is passed through a folded filter. The filtrate is concentrated to dryness, then the residue is taken up again with chloroform (500 ml). The chloroform phase is washed with acid potassium sulfate in 10% solution in water, then with water until pH neutral. After drying over sodium sulfate and concentration to dryness, a residue is obtained (2.7 g), which is chromatographed on a silica column (200 g) (eluent: ethyl acetate-hexane, 1/4, v/v. The fractions containing the product 108 are grouped together and after revaporation of the solvents, a crystalline product is obtained (1.62 g, 54%). MP: 81°–82° C., $[\alpha]_{25}{}^D = -20°$ (1, chloroform). Analysis of the infrared spectrum, elementary analysis and analysis of the nuclear magnetic resonance spectrum confirm the structure of the compound 108.

Step 5: synthesis of the derivative 109.

Product 108 (2 g) is dissolved in methanol (20 ml) and chloroform (20 ml). To this solution, is added sodium methanolate (2M, 2 ml). After 1.5 hour, the de-acetylation reaction is terminated. The reaction mixture is diluted with chloforom. The chloroform phase is washed with water until pH neutral, dried, then evaporated to dryness. In this way a residue is obtained, the compound 108 (1.8 g, 100%). It is immediately dissolved in tetrahydrofurane (50 ml), then borum hydride (BH₃, 1M) in tetrahydrofurane; (10 ml) is then added. After one hour of reaction, the excess boron hydride is destroyed by the addition of ethanol. At the end of gaseous release, the reaction mixture is diluted by the addition of tetrahydrofurane (100 ml). 3M soda (12ml) is then added, followed by hydrogen peroxide (120 volumes, 8 ml). After two hours heating to 50° C., the reaction is stopped. The solution is poured into chloroform (500 ml), then the organic phase so obtained is washed with water, with 2M hydrochloric acid, finally with water until pH neutral. In this way a very milky chloroform phase is obtained which becomes limpid in the course of drying over sodium sulfate. After filtration, the chloroform is evaporated and then the residue obtained is chromatographed on silica (200 g chloroform-methanol, 30/1, v/v).

In this way the derivative of the idose 109 (1.05 g, 55%) is obtained. This product is in the form of a syrup. $[\alpha]_{20}{}^D = +85.5°$ (1, chloroform). Elementary analysis as well as NMR Analysis confirm the expected structure.

Step 6: Synthesis of the derivative 112.

This synthesis is carried out from derivative 109 in a single step (the intermediates 110 and 111 are not isolated). To a solution of derivative 109 (2.25 g, 6 mM) in dichloromethane (50 ml), are added successively dimethylaminopyridine (60 mg; 0.24 mM) triethylamine (1.7 ml; 12 mM) and trityl chloride (2.5 g; 9 mM). After about 14 hours, the reaction is terminated. In this way the derivative 110 is obtained in solution. Then to the reaction mixture dimethylaminopyridine (150 mg), is added and triethylamine (1.7 ml) and then benzoyl chloride (1.05 ml). After 6 days, dichloromethane is removed by passage of a current of nitrogen and replaced by dimethylformamide (40 ml). The reaction mixture is heated to 70° C. during one night. Then benzoyl chloride (1 ml) and triethylamine (1.7 ml) are again added, and heating is then maintained at 70° C. for two days. Dimethylformamide is then evaporated, then the residue is taken up again with chloroform, the chloroform phase is washed with water, with a saturated sodium bicarbonate solution, then with a 2M hydrochloric acid solution, and finally with water until pH neutral. After drying, the chloroform is evaporated, which permits the compound 111 to be obtained.

The latter is immediately subjected to a reaction to eliminate the trityl group in order to obtain the derivative 112. The residue containing the derivative 111 is dissolved in 25 ml chloroform and to this solution is added 10 ml of a paratoluenesulfonic acid monohydrate solution in methanol (1M). After 4 hours of reaction at room temperature, the reaction is terminated. The reaction mixture is then diluted with chloroform, washed with water, dried and then evaporated to dryness. The residue obtained is chromatographed on silica gel (200 g, ether-hexane, 3/1, v/v). The derivative 112 is thus obtained in a pure state (1.5 g; 52%). This derivative is in the form of a syrup $[\alpha]_{20}{}^D = -8°$ (1, chloroform) Analysis of the infrared spectrum and of the NMR spectrum confirm the structure of the expected product.

Step 7: synthesis of the compound 115.

This synthesis is carried out directly from the derivative 112 without isolating the intermediates 113 and 114. To a solution of the compound 112 (1.2 g) in acetone (20 ml), is added, drope by drop, after cooling to 0° C., a solution (2.9 ml) of chromium oxide (CrO₃; 1.17 g) in sulfuric acid 3.5M (5 ml). After 30 minutes stirring at 0° C., the temperature is brought back to room temperature. Reaction develops over three hours. The reaction mixture is then poured into a separating funnel containing iced water (100 ml). The product formed is extracted with chloroform (3×50 ml). The chloroform phase is washed with water until pH neutral, then dried over sodium sulfate, filtered and concentrated to dryness. The residue obtained (compound 113) is dissolved in methanol (130 ml). To this solution soda 3M (17 ml) is added then the mixture is left under stirring for about 14 hours. After acidification with sulfuric acid, the compound 114 is extracted with ether, then immediately methylated with diazomthane by the conventional method to give the compound 115. After evaporation of the ether, the compound 115 is obtained pure by mean of silica gel chromatography (50 g; ether-hexane; 4/1; v/v). The pure fractions containing the derivative 115 are grouped together and the solvents are removed. In this way the derivative 115 of iduronic acid is obtained (587 mg, 59% with respect to derivative 112). This product is in the form of a syrup.

$[\alpha]_{25}^D = +98°$ (2.65, chloroform).

NMR analysis, infrared analysis and elementary analysis confirm the expected structure.

EXAMPLE 30

Figure 23:
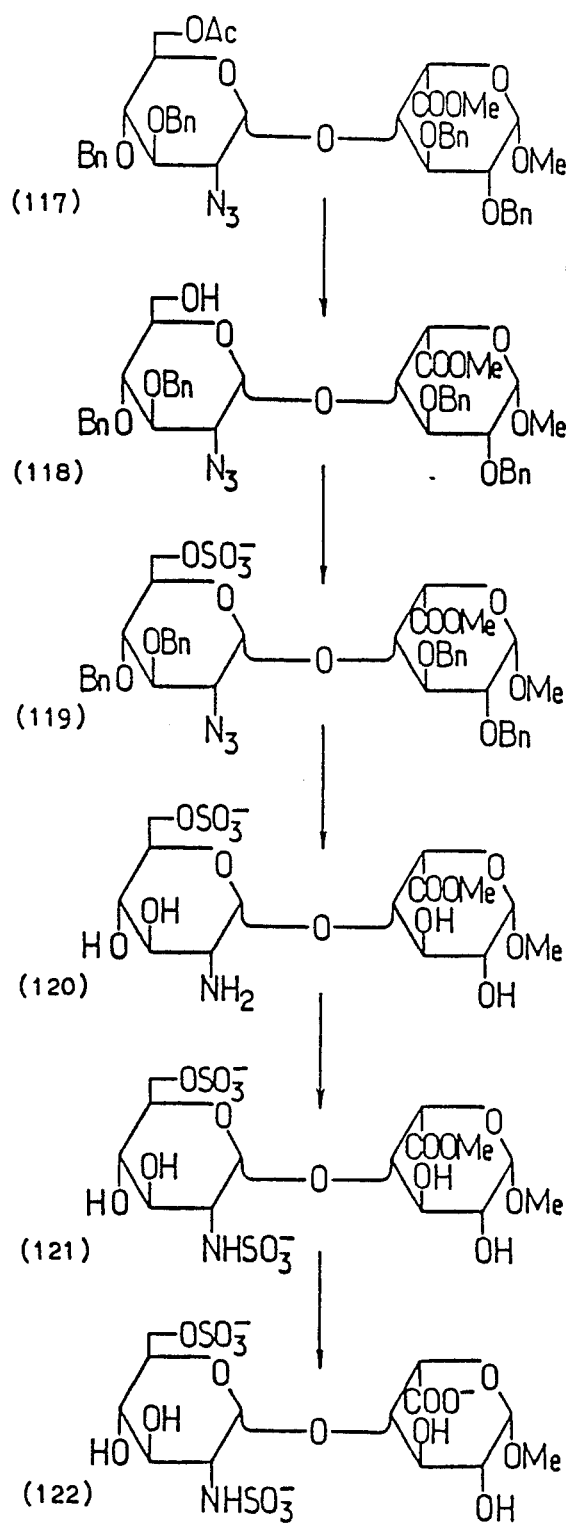
Figure 25:
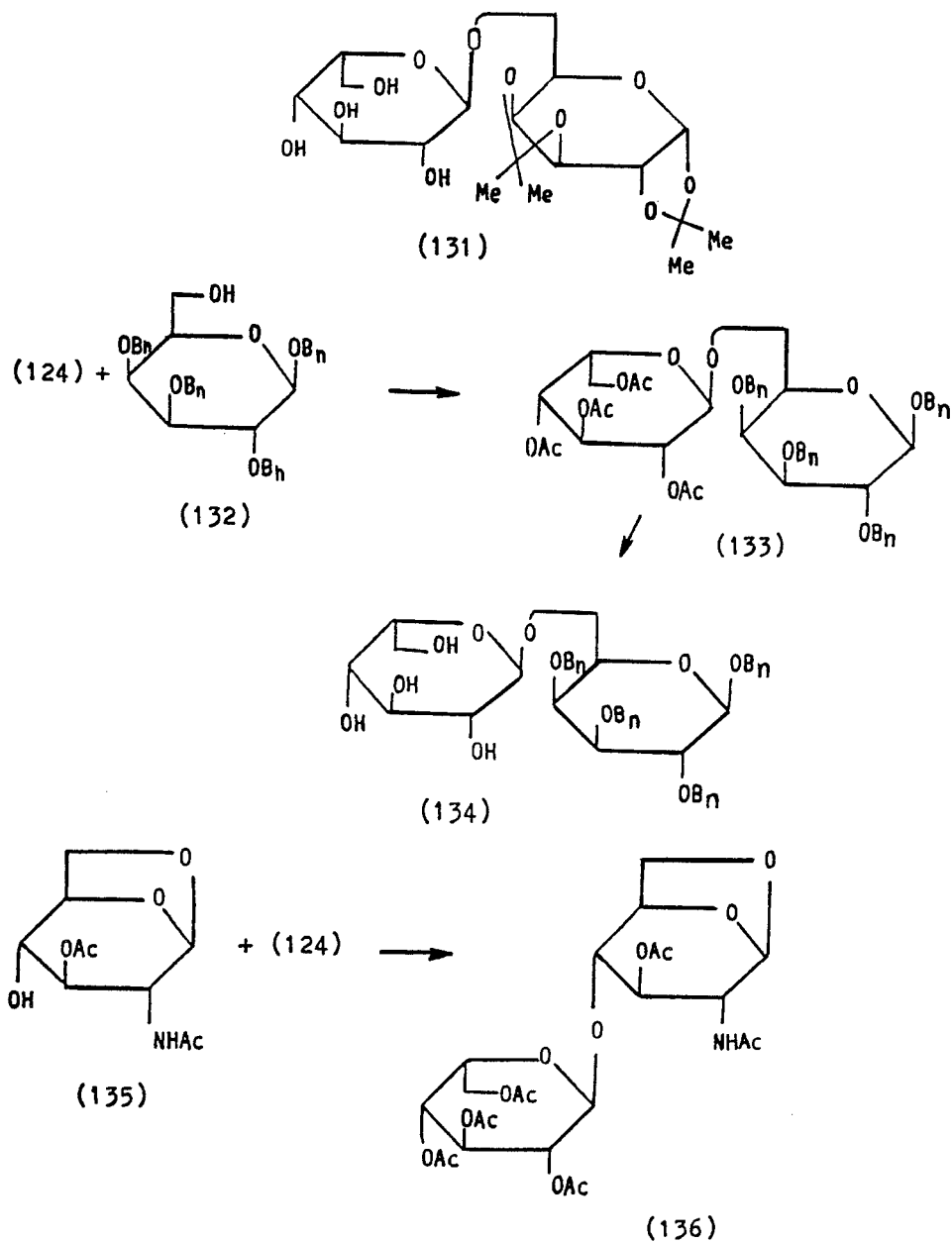

Synthesis of the disaccharide 117 (see FIGS. 22 and 23).

This synthesis is carried out from the monosaccharide 115 prepared as above and from the monosaccharide 44 prepared by the technique of H. Paulsen and W. Stenzel, chemische Berichte 111 (1978) 2234–2247.

To a solution of the compound 115 (200 mg, 0.5 mM) in dichloromethane (10 ml), are added successively the compound 44 (0.450 g) sym-collidine (150 ml) and silver triflate (260 mg.)

The reaction mixture is kept at 0° C. under a nitrogen flow and with stirring protected from moisture and from light for 3 hours.

It is then diluted with dichloro ethane (100 ml) then the solids are eliminated by filtration on pleated filters. The solution obtained is washed with a saturated solution of sodium bicarbonate with water and with 2M sulfuric acid, then again with water until pH neutral.

After drying over sodium sulfate and evaporation of the dichloromethane, the residue obtained is chromatographed on silica gel (50 g; chloroform/ethyl acetate; 15/1; v/v).

In this way the pure derivative 117 is obtained (327 mg, 82%). The product is in the form of a syrup.

$[\alpha]_{20}^D = +57°$ (1, chloroform).

NMR analysis the same way as elementary analysis confirm the structure and the anomerism of the disaccharide 117.

EXAMPLE 31

Synthesis of the disaccharide 122 (see FIG. 23).

The following steps are applied:
removal of the acetyl groups,
sulfation,
hydrogenation,
sulfation of the primary amine group.
removal of the Me group from the —COOH radical resulting in the compound 118.

The disaccharide 117 (260 mg) is dissolved in methanol (5 ml) and 1M soda (1 ml) is added drop by drop. At the end of the reaction, the reaction mixture is introduced to the top of a Dowex 50 resin column in the HT form (5 ml). The effluent is concentrated to dryness, taken up again with methanol, and the free acid product, obtained at the end of the saponification of the derivative 117 is methylated by the addition of diazomethane. In this way the derivative 118 is obtained which is purified by means of a silica gel column (20 g; ether/hexane 8/1; v/v). The yield of compound 118 is 92 mg. This product is engaged directly in the synthesis of derivative 119.

Sulfation leading to the disaccharide 119.

The product 118 obtained above (92 mg) is dissolved in dimethylformamide (5 ml) then trimethylamine/sulfur trioxide complex (25 mg) is added. The solution is brought to 50° C. for about 14 hours. After evaporation of dryness, the residue is taken up again with chloroform, then the chloroform phase is washed with water, dried and concentrated to dryness. The solid obtained is purified on a silica gel column (15 g; eluent: methanol/chloroform; 1/4 v/v). After evaporation of the pure fractions, the sulfated disaccharide 119 is obtained (58 mg; 55.6%).

Hydrogenation leading to the disaccharide 120.

The disaccharide 119 (58 mg) is dissolved in a methanol-water mixture (15 ml+2 ml). Then catalyst (Pd/C 5%; 60 mg) is added and this suspension is then subjected to stirring under a hydrogen atmosphere for 48 hours. At this stage, the complete disappearance of the benzyl groups borne by the derivative 119 is noted, in the same way as reduction of the azide group of the derivative 119 to an amino group. The catalyst is removed by filtration, then the reaction mixture is concentrated to dryness.

In this way the disaccharide 120 is obtained which will be treated directly to obtain the product 121 and 122.

Sulfation of the group —NH$_2$ leading to the disaccharide 122.

The disaccharide 120 is dissolved in water (6 ml). To this solution the complex trimethylamine/sulfur trioxide (25 mg), is added, whilst keeping the pH at 9.5 by addition of soda (0.1N). After 45 hours reaction 1N soda is added to bring the pH to 12. Then it is kept to this value for one hour. The solution of 121 is then neutralized with 1N hydrochloric acid, then passed to a Dowex 50 column (5 ml) in the Na+ form. The eluate from this column is introduced into a column G1×2 (16 ml, 1.6×8 cm). The column is eluted with a gradient of sodium chloride of 0 to 3M. The fractions containing the disaccharide 122 in the form of sodium salts are collected together, concentrated, then the product is desalted by passage over a Sephadex G25 column (50 ml) eluted with water. In this way the disaccharide 122 is obtained (27 mg, 68%). Apres lyophilisation, the product is in the form of a white powder.

$[\alpha]_{20}^D = +95.5°$ (1.3; water).

The NMR analysis of carbon 13 confirm the expected structure for the product 122.

EXAMPLE 32

Preparation of the 2-O-(α-L-idopyranosyl)-D-galactose (compound 128) (see FIG. 24).

This synthesis is carried out by the following 4 steps (a) to (d).

(a) Preparation of 2,3,4,6-tetra-O-acetyl-α-L-idopyranosyl bromide (compound 124)

A solution of 5 g of penta-O-acetyl-α-L idopyranose (compound 1, prepared according to P. PERCHEMLIDES, T. OSAWA, E. A. DAVIDSON and R. W. JEANLOZ, Carbohydr. Res., 3 (1967) 463), in anhydrous dichloromethane (100 ml) was saturated at 0° C. with hydrobromic gas. After 2 hours at room temperature, the reaction medium was poured on to ice and extracted with chloroform. The organic phase was washed with water, dried (calcium chloride) and evaporated. The residue was crystallized in the dichloroethane-ether-pentane, mixture giving the bromide 124(5 g, 95%, MP 126°-127° C. $[\alpha]_D = -120°$ (c; 0.75, chloroform).

(b) Preparation of benzyl 3,4,6-tri-O-benzyl-2-O (2,3,4,6-tetra-O-acetyl-α-L-idopyronosyl)-β-D-galactopyranoside (compound 126)

A solution of 200 mg of benzyl-3,4,6-tri-O-benzyl-β-D-galactopyranoside (compound 125 prepared by the method of J. C. JACQUINET and P. SINAY described in Tetrahedron, 32 (1976) 1963) in anhydrous dichloromethane (10 ml) was stirred under dry nitrogen at 90° C. in the presence of a molecular sieve 4 Å (300 mg) and mercuric bromide (80 mg), until the volume was reduced to half. A solution of bromide 124 (300 mg) in dichloroethane (10 ml) was added over 3 hours, the volume of the reaction mixture being kept constant by a continuous distillation of the dichloroethane. 3 hours after the end of the addition, the reaction medium was cooled to ambient temperature, diluted with chloroform (100 ml), filtered, washed successively with an aqueous solution 10% of potassium iodide, with a dilute aqueous solution of sodium hydrogenocarbonate, with water, dried (sodium sulfate) and evaporated. The residue is purified by chromatography on a silica gel column (30 g) by means of a mixture ethyl-hexane acetate (1:1, v/v), giving the disaccharide 126 in the state of a syrup (290 mg, 90%), $[\alpha]_D = -57°$ (c: 1,1 chloroform). Analysis calculated for $C_{48}H_{54}O_{15}$: C, 66.20; H, 6.25; O, 27.55. Found: C: 65.98; H, 6.13; O, 27, 35%.

(c) Preparation of benzyl-3,4,6-tri-O-benzyl-2-O-(α-L-idopyranosyl)-β-D-galactopyranoside (compound 127)

The disaccharide 126 (200 mg) was dissolved in anhydrous methanol (100 ml) and a M solution of sodium methylate in anhydrous methanol (0.2 ml) was added. After one hour, the reaction medium was neutralised by means of Dowex 50 (H+) resin, filterered and evaporated. The residue was purified by chromatography on a silica gel column (10 g) by means of the mixture dichloroethane-acetone (7:3, v/v) giving the disaccharide 127 (154 mg, 95%) in a pure state, $[\alpha]_D = -43°$ (c: 1,4 chloroform). Analysis calculated for $C_{40}H_{46}O_{11}$: C, 68.36; H, 6.60: O, 25.04; found: C, 68.38; H, 6.64; O, 25,27%).

(d) Preparation of 2-O-(α-L-idopyranosyl)-D-galactose (compound 128)

The disaccharide 127 (200 mg) was hydrogenated for 48 hours in ethanol (10 ml) containing acetic acid (0.1 ml), in the presence of 10% palladium on charcoal (50 mg). The product was purified by chromatography on a silica gel column (15 g), by means of the mixture methanol-chloroform (4:1, v/v), giving the free disaccharide 6 in the form of a hygroscopic white powder (97.5 mg, 100%), $[\alpha]_D = +28°$ (c: 1,2, methanol)+15° (10 min)→+93° (2 h) (c 1.2 water). Analysis calculated for $C_{12}H_{22}O_{11}$: C, 42.10; H, 6.48 found: C, 41.71; H, 6.48%.

EXAMPLE 33

Synthesis of 1,2: 3,4-di-O-isopropylidene-6-O (α-L-idopyranosyl)-α-D-galacto pyranose (compound 131)

Firstly the 1,2: 3,4-di-O-isopropylidene-6-O (2,3,4,6-tetra-C acetyl-α-L-idopyronosyl)-α-D-galactopyranose (compound 130) was prepared.

A solution of 300 mg of 1,2: 3,4-di-O-isopropylidene-α-D-galactopyranose (compound 129) prepared according to R. C. HOCKETT H. G. FLETCHER and J. B. AMES in J. Am. Chem. Soc., 63 (1941) 2516) in anhydrous dichloethane (20 ml) was stirred under dry nitrogen at 90° C. in the presence of a molecular sieve 4 Å (500 mg) and mercuric bromide (300 mg), until the volume was reduced to half. A solution of bromide 124 (550 mg) in dichloroethane (10 ml) was added and after 24 hours, a further addition of bromide 124 (125 mg) in dichloroethane (2 ml). 24 h after the latter addition, the reaction medium is treated as described above for the preparation of the disaccharide 126. Purification by chromatography on a silica gel column (50 g) by means of the mixture dichloroethane-acetone (9:1, v/v) leads to the disaccharide 130, which is crystallized in the mixture dichloroethane/pentane (650 mg, 95%), MP 160°-161° C., $[\alpha]_D = -86°$ (c: 1, chloroform). Analysis calculated for $C_{26}H_{38}O_{15}$: C, 52.88; H, 6.48; O, 40.64. Found: C, 52.89; H, 6.41; O, 40.63%.

The derivative 130 is then applied for the preparation of 1,2: 3,4-di-O-isopropylidene-6-O (α-L-idopyranosyl-α-D-galactopyranose (compound 131), by proceeding as follows: The disaccharide 130 (300 mg) is desacetylated by the technique previously described for the preparation of the disaccharide. Purification by chromatography on a silica gel colummn (15 mg) by means of the mixture methanol-chloroform (4:1, v/v) leads to the disaccharide 131 obtained in the form of an amorphous hygroscopic powder (204 mg, 95%), $[\alpha]_D = -63°$ (c: 0,7, methanol). Analysis calculated for $C_{18}H_{30}O_{11}$: C, 51.18; H, 7.16; 0, 41.66. Found: C, 50.86 (see FIGS. 24 and 25).

EXAMPLE 34

Preparation of benzyl-2,3,4-tri-O-benzyl-6-O-(α-L-idopyranosyl)-β-D-galactopyranoside (compound 134)

First benzyl-2,3,4-tri-O-benzyl-6-O (2,3,4,6-tetra-O-acetyl-α-L-idopyranosyl)-β-D-galactopyranoside (compound 133) was prepared.

A solution of 200 mg of benzyl-2,3,4-tri-O-benzyl-β-D-galactopyranoside (compound 132, prepared according to K. MIYAT and R. W. JEANLOZ, Carbohydr. Res., 21 (1972) 45), in anhydrous dichloroethane (15 ml) was stirred under dry nitrogen 90° C. in the presence of a 4 Å molecular sieve (300 mg) and mercuric bromide (80 mg), until the volume was reduced to 5 ml. A solution of bromide 124 (160 mg) in dichloroethane (10 ml) was added and the reaction medium was stirred at 90° C. for 24 h. Treatment similar to that described previously for the preparation of the disaccharide 126 resulted in a residue which was purified by chromatography on a silica gel column (30 g) by means of the mixture dichloethane-acetone (12:1, v/v), giving the disaccharide 133 (227 mg; 70%), $[\alpha]_D = -30°$ (c: 1, chloroform). Analysis calculated for $C_{48}H_{54}O_{15}$: C, 66.20; H, 6.25; O, 27.55. Found: C, 65.96; H, 6.23; O. 27 66%.

The compound 133 was then applied for the preparation of benzyl-2,3,4-tri-O-benzyl-6-O-(α-L-idopyranosyl)-β-D-galactopyranoside (compound 134) by proceeding as follows: The disaccharide 133 (200 mg) was desacetylated by the technique described previously for the preparation of the disaccharide 127.

Purification by chromatography on a column of silica gel (10 g) by means of the mixture chloroform-methanol (9:1, v/v) leads to the disaccharide 134 obtained in amorphous form (147 mg, 90%), $[\alpha]_D = -88°$ (c: 0,8, chloroform). Analysis calculated for $C_{40}H_{46}O_{11}$: C, 68.36; H, 6.60; O, 25.04 Found: C, 68.74; H, 6.68; O, 25.37% (see FIG. 25).

EXAMPLE 35

Preparation of 2-acetamido-1,3,6-tri-O-acetyl-4-O-(2,3,4,6-tetra-O-acetyl-α-L-idopyranosyl 2-desoxy-β-D-glucopyranose (compound 138) (FIG. 26)

The preparation of this compound was carried out by the following steps (a) to (c).
(a) Preparation of 2-acetamido-3-O-acetyl-1,6-anhydro-2-desoxy-4,O-(2,3,4,6-tetra-O-acetyl-α-L-idopyranosyl-β-D-glucopyranose (compound 136)

A solution of 1 g of 2-acetamido-3-O-acetyl-1,6 anhydro-2-desoxy-β-D-glucopyranose (compound 135 prepared according to F. SCHMITT and P. SINAY, Carbohydr. Res., 29 (1973) 99.) in anhydrous nitrobenzene (40 ml) was stirred for 2 h at 130° C. in the presence of a 4 Å molecular sieve in powder form (1 g), previously activated for 48 h at 250° C. A solution of bromide 124 (1.43 g) in dichloroethane (10 ml) is added and the reaction medium is kept at 130° C. for 10 h. A further addition of bromide 124 (0.7 g) in dichloroethane (5 ml) is then made and the reaction continued for 24 h. Treatment similar to taht described for the preparation of disaccharide 126 leads to a compound which is purified by chromatography on a silica gel column (200 g) by means of a mixture ethyl-acetate-ether (5:1, v/v), giving the disaccharide 136 (1.8 g, 85%), $[\alpha]_D=70.6°$ (c: 1, chloroform). Analysis calculated for $C_{24}H_{33}O_{14}N$: C, 51.52; H, 5.94 N, 2.50; O, 40.03. Found C, 51.35; H, 5.89; N, 2.51; O, 40.05%.
(b) Preparation of 2-acetamido-1,6-anhydro-2-desoxy-4-O-(α-L-idopyranosyl)-β-D-glucopyranose (compound 137)

The disaccharide 136 (500 mg) is de-acetylated by the technique described previously for the preparation of disaccharide 127. A purification by chromatography on a silica gel column (40 g) by means of the mixture ethyl acetate-methanol (2:1, v/v) leads to the disaccharide 137 (300 mg, 90%), $[\alpha]_D=-65°$ (c: 1,6, methanol). Analysis calculated for $C_{14}H_{23}O_{10}N$, 0,5 $H_2O$: C, 44.92; H, 6.46; N, 3.74. Found: C, 44.95; H, 6.61; N, 4.27%
(c) Preparation of 2-acetamido-1,3,6-tri-O-acetyl-4-O-(2,3,4,6-tetra-O-acetyl-α-L-idopyranosyl) 2-desoxy-β-D-glucopyranose (compound 138)

The disaccharide 136 (150 mg) is acetolysed at ambient temperature for 12 hours in the presence of a mixture (5 ml) of acetic anhydride-acetic acid and concentrated sulfuric acid (7:3:0, 1, v/v). The reaction medium is then poured into iced water and stirred for 4 hours, then extracted with chloroform (100 ml). The chloroform phase is washed with dilute aqueous solution of sodium hydrogenocarbonate, with water, dried (sodium sulfate) and evaporated. The residue is purified by chromatography on a silica gel column (10 g) by means of the mixture ethyl acetate-ether (5:1, v/v) giving the disaccharide 136 which is crystallized in the mixture ethyl acetate-pentane (120 mg, 64%), MP 120° C., $[\alpha]_D=40°$ (c: 1, chloroform). Elementary analysis calculated for $C_{28}H_{39}O_{18}N$: C, 49.63; H, 5.80; O, 42.50; N, 2.07; Found: C, 49.68; H, 5.91; O, 42.16; N, 2.12%

EXAMPLE 36

Synthesis of 2-acetamido-2-desoxy-4-O-(α-L-idopyranosyl)-D-glucopyranose (compound 139) (FIG. 26).

The disaccharide 138 (100 mg) is desacetylated by the previously described technique for the preparation of the disaccharide 127. Purification by chromatography on a silica gel column (5 g) by means of the mixture methanol-chloroform (3:2, v/v) results in the disaccharide 139 which is crystallized in aqueous ethanol (48 mg, 85% MP 143°–145° C., $[\alpha]_D=-20°-31°$ (c 0.8, water-methanol, 19:1, v/v, after 14 h. Analysis: calculated for : $C_{14}H_{25}NO_{11}$, 0.5 $H_2O$: C, 42,86; H, 6.68; N, 3.57 Found: C, 42.83; H, 6.68; N, 3.59%.

EXAMPLE 37

Figure 27:
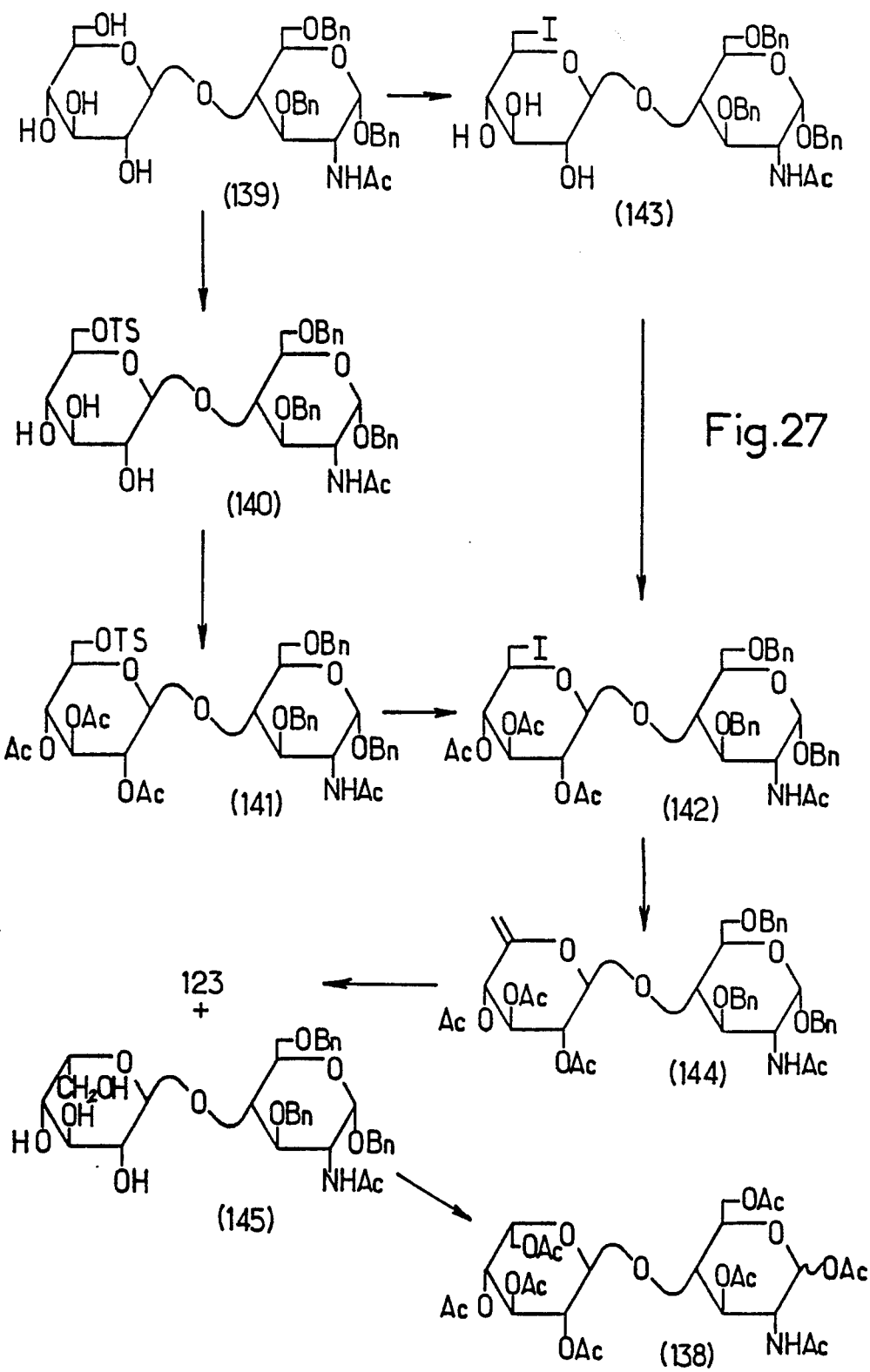

Modification in the preparation of the compound 138 by the step 1 to 6 (see FIG. 27)

1. Preparation of benzyl 2-acetamido-3,6-di-O-benzyl-2-desoxy-4-O-(6-O-tosyl-β-D-glucopyranosyl)-α-D-glucopyranoside (compound 140)

A solution of the compound 139 (0.2 g) in pyridine (5 ml) is cooled to 0° C. Tosyl chloride (0.07 g) dissolved in pyridine (2 ml) is then added. The reaction is left at room temperature for 24 hours. After addition of several drops of water, the mixture is stirred for half-hour before being poured onto ice. After taking up again with chloroform (0.2 l), the chloroform phase is washed successively with a 10% aqueous solution of $KHSO_4$, with water, a saturated solution of $NaHCO_3$ and water. After drying over sodium sulfate and concentrating to dryness, the residue was chromatographed on silica gel (20 g) in a ethyl acetate/methanol mixture (15/1, v/v). In this way pure compound 140 was obtained (150 mg; 60%). $[\alpha]_D^{20}=+74°$ (1,1 chloroform). Elementary analysis calculated for $C_{42}H_{49}O_{13}NS$ (807,912) C, 62.40; H, 6.11; N, 1.73; O, 25.74; S, 3.97. Found: C, 62.77; H, 6.13; N, 1.73; O, 24.98; S, 3.48. The NMR spectrum confirms the desired structure.

2. Preparation of benzyl 2-acetamido-3,6-di-O-benzyl-2-desoxy-4-O-(2,3,4-tri-O-acetyl-6-O-tosyl-β-D-glucopyranosyl)-α-D-glucopyranoside (compound 141)

To a solution of compound 139 (200 g) in pyridine (5 ml), acetic anydride (5 ml) is added. After one night at room temperature, the reaction mixture was concentrated to dryness. The residue was chromatographed on a silica gel column (25 g) in an ethyl acetate/hexane mixture (3/1, v/v). This way the compound 141 was obtained (208 mg, 90%) in the form of a syrup. $[\alpha]_D^{20}=+70°$ (1, chloroform). Elementary analysis calculated for $C_{48}H_{55}NSO_{16}$ (934,023) C, 61.78; H, 5.94; N, 1.5; O, 27.41; S, 3.43. Found: C, 61.58; H, 5.91; N 1.27; S, 3.23. The NMR spectrum confirms the desired structure.

3. Preparation of benzyl 2-acetamido-3,6-di-O-benzyl-2-desoxy-4-O(2,3,4-tri-O-acetyl-6-desoxy-6-iodo-β-D-glucopyranosyl)-α-D-glucopyranoside (compound 142)
 (1) From compound 141

To a solution of compound 141 (150 mg) in acetone (5 ml), sodium iodide (150 mg) is added. The mixture is heated to 70° C. in a sealed tube for 7 hours. After evaporation to dryness, the residue is taken up again with water and chloroform. The chloroform phase was washed with water and dried over sodium sulfate. After evaporation to dryness, the residue was crystallized in a chloroform/pentane mixture (102 mg, 70%). m.p.

173°-174° C. $[\alpha]_D^{20} = +78.5°$ (1.2 chloroform). Elementary analysis calcul. for: $C_{41}H_{48}O_{13}NI$ (889,733) C, 55.34; H, 5.44; N, 1.57; O, 23.38; I, 14.28. Found: C, 54.98; H, 5.52; N, 1.45; O, 23.57; I 14.10. The NMR spectrum corresponds to the desired structure.

(2) From compound 139 via the compound 143

A solution of compound 139 (1 g) and N-iodo-succinimide (1 g) in DMF (50 ml) was stirred at 0° C. for 30 minutes. Triphenylphosphine (1.2 g) was then added slowly in one hour. After heating at 50° C. for one hour, methanol (1 ml) was added and then the reaction mixture was concentrated to dryness. The product was extracted with chloroform. The chloroform phase washed with water, with a solution of sodium triosulfate then again with water. After drying and evaporation of the chloroform, the residue was deposited on a silica gel column (50 g). The compound 143 contaminated with triphenylphosphine was eluted by an ethyl acetate methanol mixture (15/1, v/v).

After evaporation of the chromatography solvent and drying the derivative 143 is dissolved in pyridine (10 ml) then acetylated with acetic anhydride (10 ml). After conventional treatment, the derivative 142 is crystallized in a mixture chloroform/pentane. The yield with respect to compound 139 is 85%. This compound is in every respect similar to that obtained from compound 141.

4. Preparation of benzyl 2-acetamido-3,6-di-O-benzyl-2-desoxy-4-O-(2,3,4-tri-O-acetyl-6-desoxy-β-D-xylo-hex-5-(enopyranosyl)-α-D-glucopyranoside-2 (compound 144)

To a solution of compound 142 (400 mg) in anhydrous pyridine (5 ml), silver fluoride (400 mg) is added. The suspensionis stirred in the dark for 48 hours. The mixture is then poured with stirring with ether (200 ml). After filtration, the ether phase is washed with a 10% solution of NaHSO$_4$, then with a 10% solution of NaHCO$_3$ finally with water. After drying and concentrating to dryness, The residue is crystallized in chloroform/ether mixture (206 mg; 60%) m.p. 184°-185° C. $[\alpha]_D^{20} = +70°$ (1.4 chloroform). Elementary analysis calcul. for: $C_{41}H_{47}NO_{13}$ (761,821): C, 64.69; H, 6.22; N, 1.84. Found: C, 64.5; H, 5.96; N, 1.79. The NMR spectrum is in accordance with the desired structure.

5. Preparation of benzyl 2-acetamido-3,6-di-O-benzyl-2-desoxy-4-O-(α-L-idopyranosyl-α-D-glucopyranoside (compound 145)

The compound 144 (380 g) is dissolved in freshly distilled tetrahydrofurane (8 ml). After cooling to 0° C. in a nitrogen atmosphere, boron hydride (BH$_3$, 1M in THF, 1 ml) is added and then the temperature is allowed to rise again to room temperature. After one hour of reaction, a further addition of hydride is made (1 ml). After 30 minutes, ethanol is added drop by drop. When the release of gas has ceased, the mixture is diluted with THF (10 l). Soda (3M, 1.2 ml) is added followed by oxygen peroxide (120 vol; 0.8 ml). After two hours at 50° C., the solution is poured into chloroform. The chloroform phase is washed with aqueous hydrochloric acid solution (0.1N) then with water. After drying (Na$_2$SO$_4$) and concentration to dryness, the residue is chromatographed on a silica gel column (45 g) in a ethyl acetate/methanol mixture (15/4; v/v). The derivative 145 is first eluted (63 mg; 15%) followed by the derivative 139 (225 mg; 54%). The derivative 145 is crystallized in a mixture of ethyl acetate/methanol m.p. 191° C. $[\alpha]_D^{20} = +64.4°$ (1, methanol). Elementary analysis calcul. for $C_{35}H_{43}NO_{11}$, $H_2O$: C, 62.57 H, 6.75; N, 2.08. Found C, 62.42; H, 6.55; N, 1.88.

6. Preparation of 2-acetamido-1,3,6-tri-O-acetyl-2-desoxy-4-O (2,3,4,6-tetra-O-acetyl-α-idopyranosyl)-D-glucopyranose-(compound 138)

A solution of the derivative 145 (35 mg) in methanol (10 ml) is stirred in the presence of a catalyst (Pd/C, 5%; 25 mg) in hydrogen atmosphere for 48 hours. After filtration and evaporation, the residue (17 mg) is acetylated with a pyridine/acetic anhydride mixture (2 ml/1 ml). After conventional treatment, the residue is chromatographed on a silica gel column (10 g) eluted with ethyl acetate. After crystallisation, compound 138 is obtained (14 mg; 32%). m.p. 191° C. $[\alpha]_D^{20} = +8°$ (0.6, chloroform).

EXAMPLE 38

Synthesis of the trisaccharide 149 of the formula

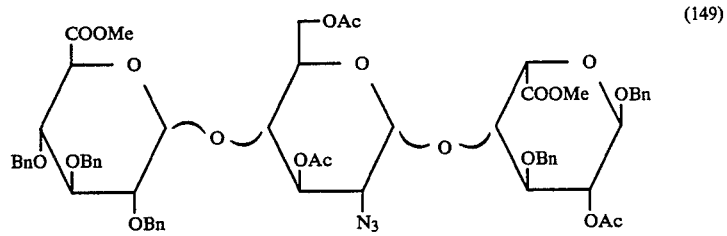

(149)

Figure 28:
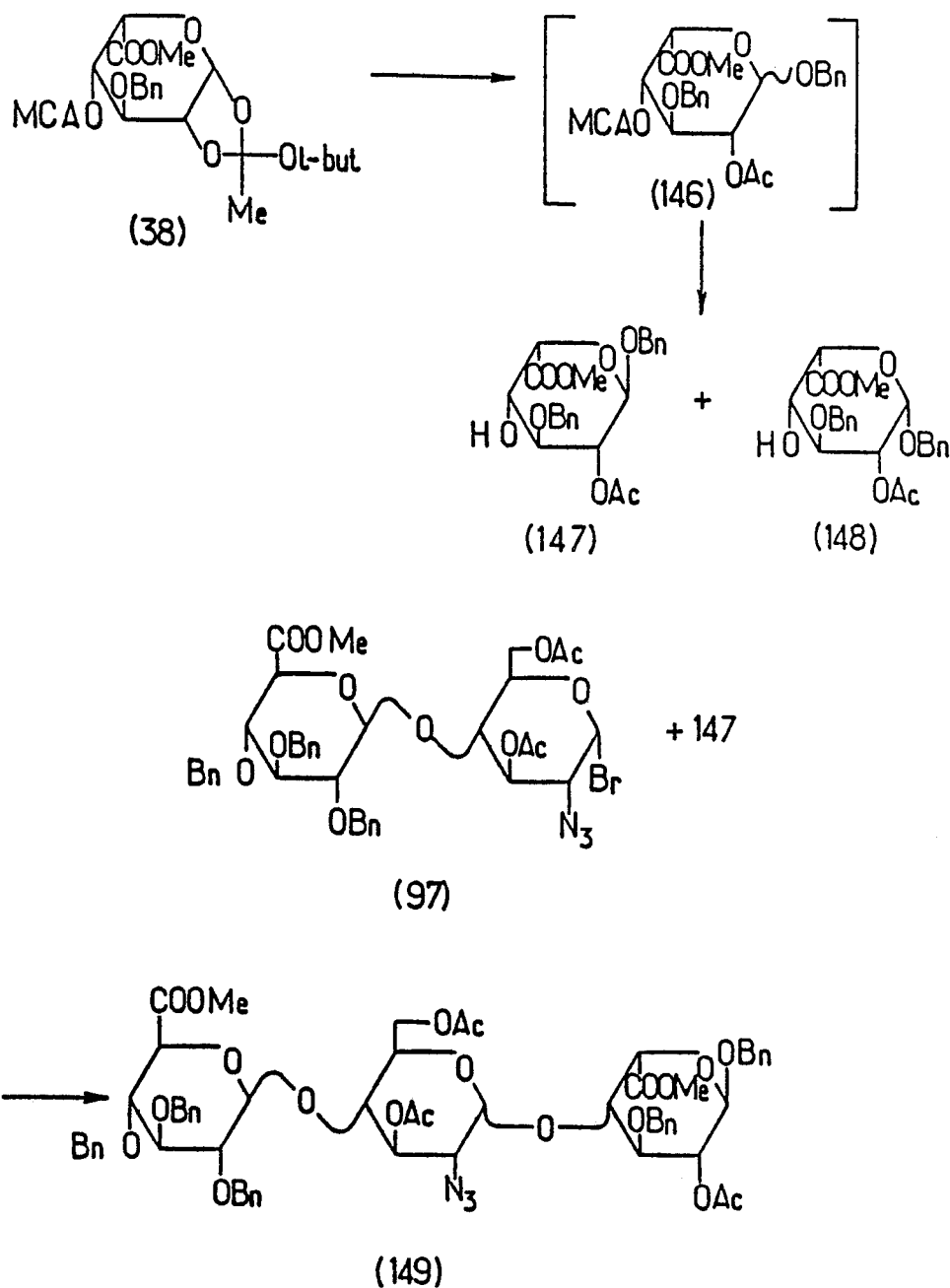
Figure 29:
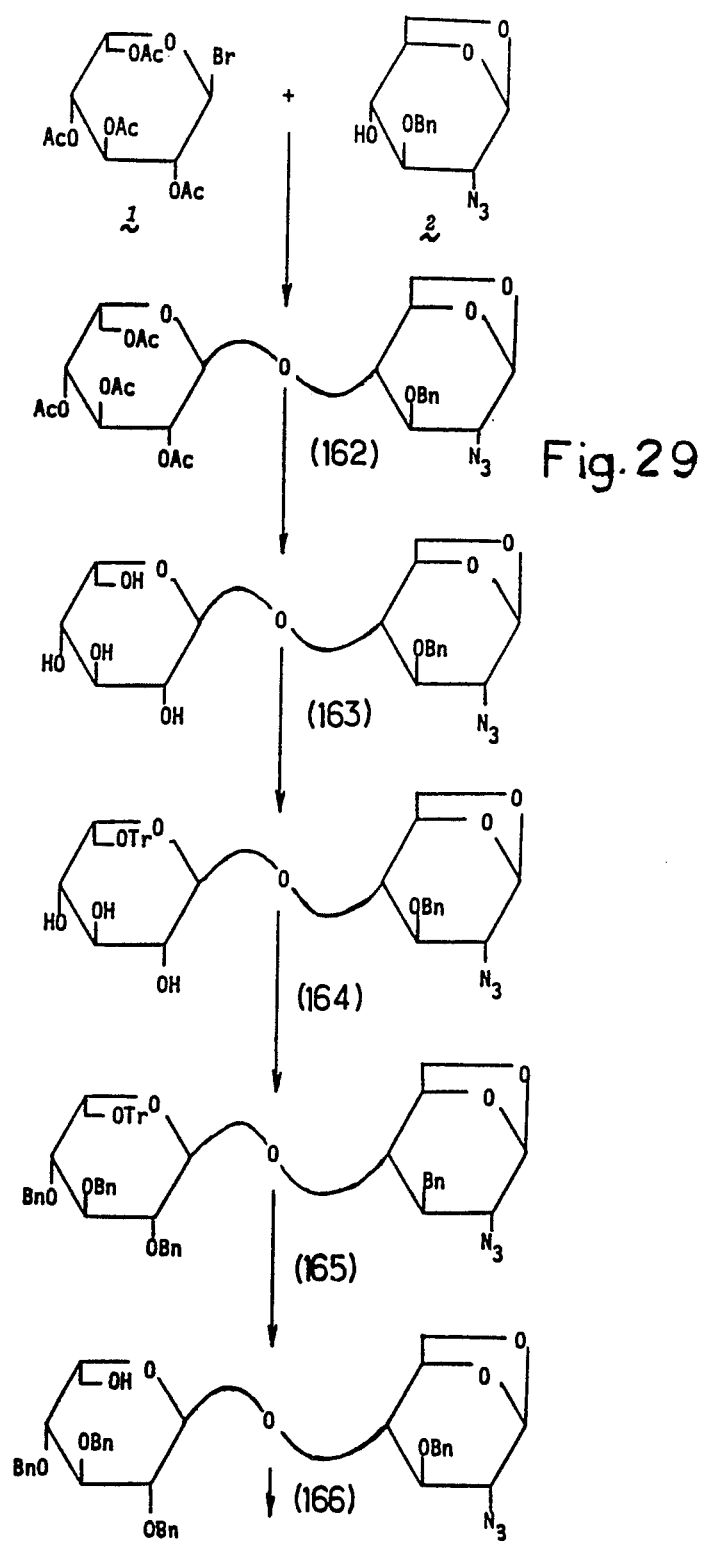
Figure 30:
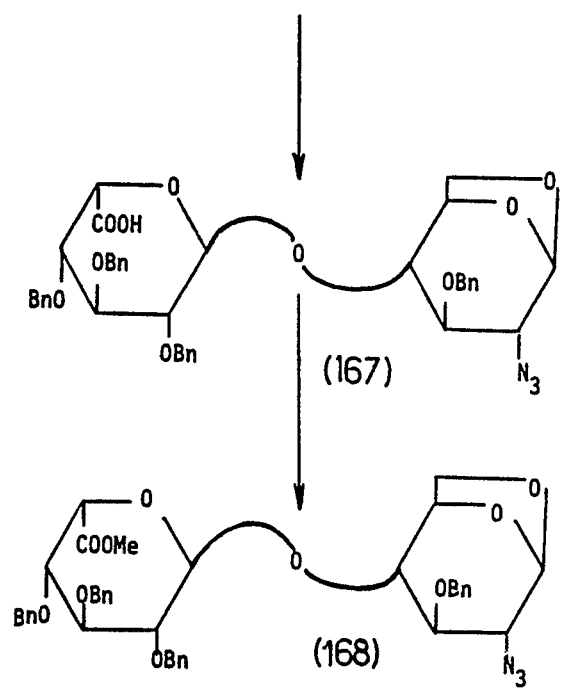
Figure 31:
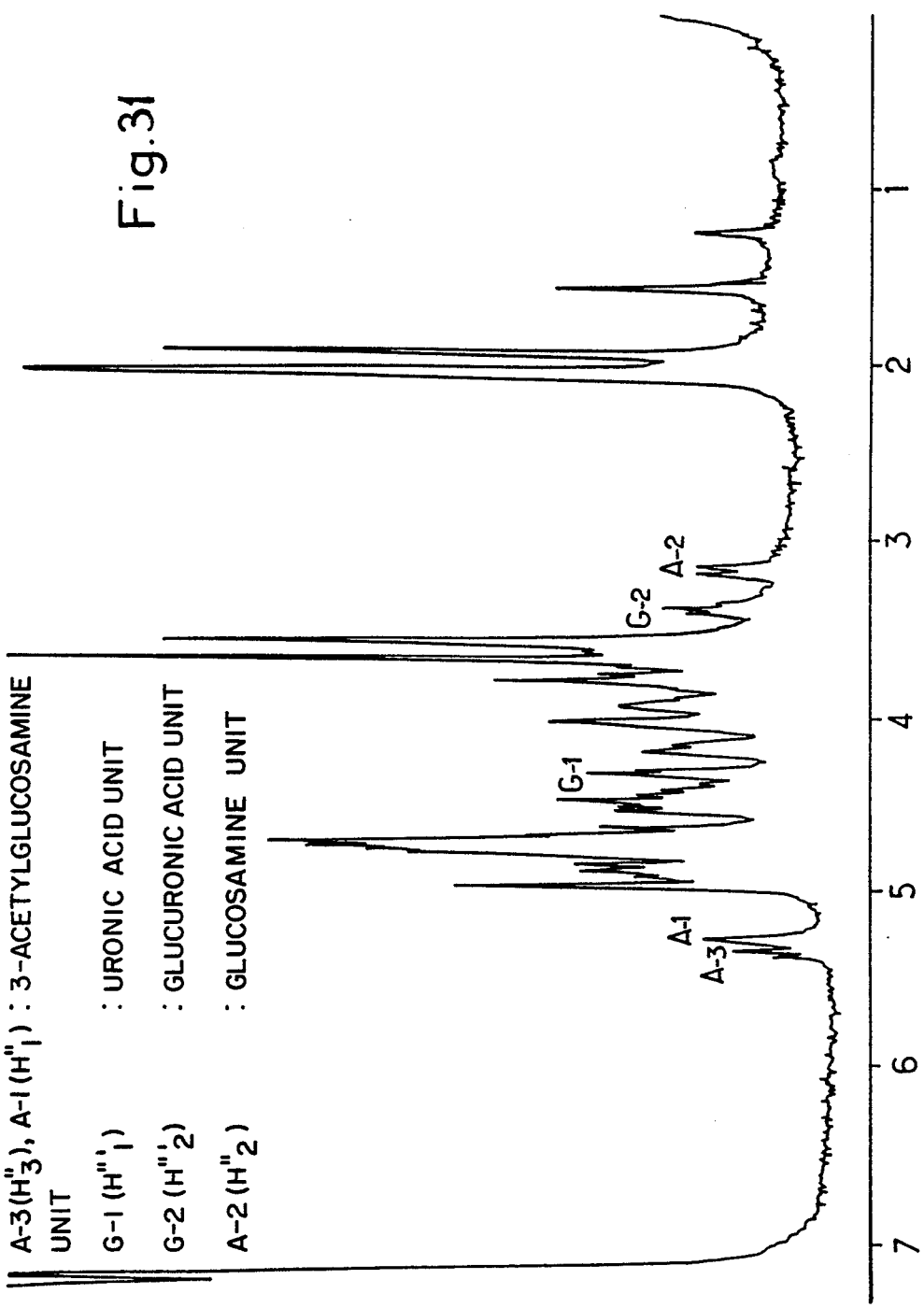

This synthesis is carried out in 3 steps (see FIG. 28). First, glycosylation of the orthoester of a derivative of L-iduronic acid is carried out. Then selectively the monochloroacetyl group, then one of the alcohols formed is reacted zith a disaccharide.

(1) Glycosylation of the orthoester 38 with benzyl alcohol

A solution of the orthoester 38 (118 mg 0.25 mM) obtained according to Example 5 and benzyl alcohol (0.15 ml, 15 mM, freshly distilled) in anhydrous chlorobenzene (10 ml) is heated to 140° C. protected from moisture. After slow distillation of 8 ml of solvent, a solution of 2,6-dimethylpyridinium perchlorate (2.5 μM) in chlorobenzene (2 ml) is added drop by drop in 30 min with simultaneous distillation of solvent (2 ml). The reaction mixture is then stirred for 30 min under these conditions, with the addition drop by drop of fresh solvent and simultaneous distillation, so that the reaction volume remains constant and equal to about 2 ml. After cooling the dilution with chloroform (50 ml), the organic phase is washed with 5% aqueous solution of sodium hydrogen carbonate, with water, dried (sodium sulfate) filtered and evaporated.

The residue is chromatographed on a silica gel column (8 g). Elution by the mixture hexane-ethyl acetate (2:1, v/v) enables a fraction to be obtained coating the mixture 146 of glycosides and which has not been separated at this stage (102 mg, 81%), N.M.R. (90 MHz, CDCl$_3$): δ: 7.30 (m, 10H, 2 Ph, 3.98 (s, 2H, Cl—CH$_2$—CO), 3.74 (s, 3H, COOMe), 3.08 and 2.03 (2s, 3H in total, OAc from β and α; β:≃ 2:1).

(2) Selective O-demonochloroacetylation

A solution of the preceding mixture 146 (102 mg) in pyridine (5 ml) and absolute ethanol (1 ml) is heated to 100° C. for 20 min in the presence of thiourea (25 mg). After cooling, the reaction mixture is evaporated to dryness and the residue is taken up again with a water-chloroform mixture (1:1, v/v, 50 ml). The organic phase is washed with water, dried (sodium sulfate), filtered and evaporated.

The residue is chromatographed on a silica gel column (10 g). Elution with the mixture ethyl acetate-hexane (4:3, v/v) enables the isolation (in order of elution) of:

the glycoside 148 (26 mg, 25%), colorless syrup, [α]$_D$+70° (c 1, chloroform) N.M.R. (90 MHz, CdCl$_3$): δ: 7.30 (m, 10H, 2 Ph); 5.05 m, 1H, H$_2$); 4.90 (d, 1H, H$_1$, 1.2 J=2 H$_z$); 3.78 (s, 3H, COOMe); 3.12 (1H, OH, exchanged with D$_2$O); 2.05 (s, 3H, OAc).

the α glycoside 147 (54 mg, 50% from 38) colorless syrup, [α]$_D$−65° (c1, chloroform) N.M.R. (90 MHz, CdCl$_3$): δ: 7.30 (m, 10H, 2 Ph); 5/05 (2H, H$_1$ and H$_2$, very weak coupling constants for J$_{1,2}$≦1 Hz); 3.78 (s, 3H, COOMe); 2.80 (1H, OH, exchanged with D$_2$O); 2.06 (s, 3H, OAc).

(3) Glycosylation of the alcohol 147 by means of the disaccharide 97

A solution of the alcohol 147 (22 mg, 50M), and of the bromide 97 obtained according to example 6 (57 mg, 70M) in anhydrous dichlomethane (1.5 ml) is stirred protected from light and moisture in the presence of 4 Å molecular sieve (powder, 50 mg). The reaction mixture is cooled to −20° C. and sym-collidine (110 l) and the silver triflate (26 mg, 100M) are added successively. The reaction mixture is stirred 2 h under these conditions, diluted with dichloromethane (50 ml) the solids are drained and the filtrate is washed with an iced aqueous solution of 0.1M HCl, with water, with a 5% aqueous solution of sodium hydrogencarbonate, with water, dried (sodium sulfate), filtered and evaporated.

The residue is chromatographed on a silica gel column (8 g, gel 230–400 mesh). Elution by the mixture toluene-ace ethyl acetate (5:1, v/v) enables the isolation of the trisaccharide 149 in the form of a colorless syrup (50 mg, 86%).

Figure 32:
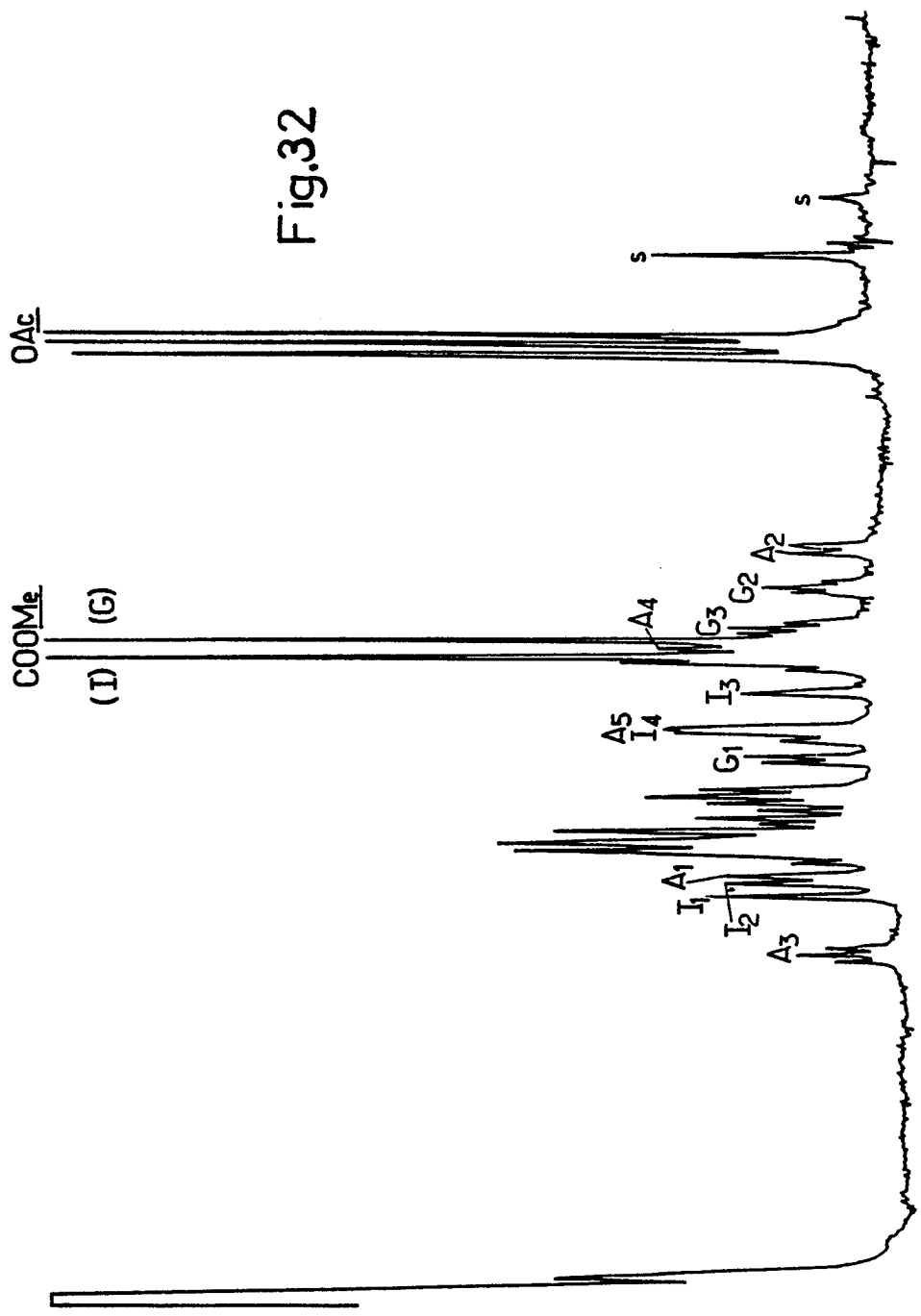

The N.M.R. spectrum (270 MHz, CDCl$_3$) is in accordance with the expected structure. This spectrum is shown in FIG. 32.

EXAMPLE 39

Fixation of the tetrasaccharide on BSA

To a solution of bovine serum albumin (BSA: 7 mg; 0.1 μple) and of tetrasaccharide (15 mg; 10 μmoles) in a sodium phosphate buffer (0.15M; pH 7.0; 2.5 ml), is added sodium cyanoborohydride (13 mg; 200 μmoles) and the solution taken to 37° C. for five days. The reaction mixture is then chromatographed on a Sephadex G-50 (1×100 cm) column, eluted with water, so as to separate the salts and the pentasaccharide not fixed to the protein-oligosaccharide conjugate. Under these conditions, a fixation of 12 moles of tetrasaccharide per mole of BSA is obtained.

The same reaction can be carried out on an insoluble support usuch as 2-aminoethyl-polyacrylamide or 2-aminoethyl-cellulose, or any other support containing a primary amine function.

In the same way, by operating in the presence of antithrombin III (instead of BSA), under the conditions defined above, a fixation of the oligosaccharide on antithrombin III, and through this a permanently activated antithrombin III is obtained (BJORK et al., FEBS Letters, 143 (1982), 96–100).

SYNTHESIS OF THE DISACCHARIDE 163

To a solution of compound 2 (5.6 g) and of mercuric cyanide (3.5 g) in dichloroethane (40 ml), are added, after distillation of about ml of solvent, 4 Å molecular sieve (1 g) then the compound 1 (3.44 g; 8.82 mmoles). After one night with stirring the solids are removed by filtration, then washed with dichloromethane. The latter is then joined with the solution and then the organic phase obtained is washed with a saturated potassium iodide solution, then with water. After drying and concentrating to dryness, the syrup obtained (10 g) is deacetylated in the presence of sodium methanolate (2M, 1 ml) in methanol (20 ml). The compound 163 obtained (2.7 g) after chromatography on silica gel (50 g; chloroform/methanol; 20/1; v/v), is a syrup ([α]$_D^{20}$= −12° (1,1 chloroform) which is used as such in the synthesis of 5.

SYNTHESIS OF THE COMPOUND 164

The disaccharide 163 (2.7 g) is dissolved in anhydrous DMF (27 ml) then successively to this solution are added trityl chloride (4.42 g) dimethylaminopyridine (135 mg) then triethylamine (2.7 ml). After two days at room temperature, the reaction mixture is concentrated under vacuum. Then the residue is chromatographed on silica gel (50 g; hexane then hexane/ethyl acetate; 2/1 then 1/1; v/v). In this way 164 is obtained (2.6 g). It is a syrup; [α]$_D^{20}$= −16.3° (1,3; chloroform).

SYNTHESIS OF THE DISACCHARIDE 166

The syrup obtained at the end of the preparation 164 (2.4 g) is dissolved in DMF (40 ml). Then barium hydroxide octahydrate (1.64 g), barium oxide (7.08 g) and finally benzyl bromide (2 ml), are added. After 4 hours of reaction, methanol is added followed by chloroform

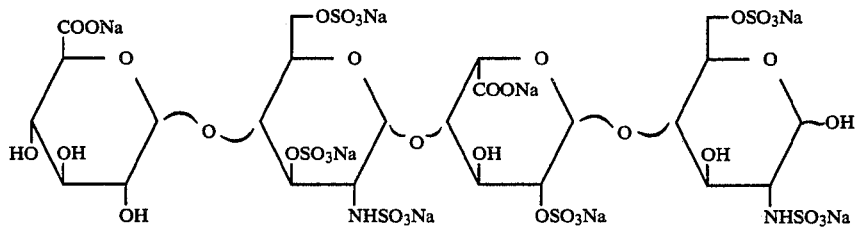

(100 ml). The solids are drained and then the chloroform phase is concentrated to dryness. The disaccharide 165 obtained at this stage is directly converted into 166.

For this, the residue is taken up again in dichloromethane (20 ml) then a solution of $BF_3$ in methanol (2 ml) is added, at 0° C., protected from moisture. After 4 hours of reaction, the reaction mixture is diluted with dichloromethane then washed with an aqueous sodium bicarbonate solution. After drying and concentration, the residue is chromatographed on a silica gel column (100 g; hexane/ethyl acetate; 4/1 then 1/1, v/v). In this way 166 is obtained $[\alpha]_D^{20} = -2°$ (0,7 chloroform).

SYNTHESIS OF THE COMPOUND 168

The derivative 166 is dissolved in acetone (20 ml). Then there is added, at 0° C., a chromic oxide (VI) (670 mg) solution in 3.5M sulfuric acid (3 ml). After 1.5 hours, ice and water are added to the reaction mixture, then the oxidized product is extracted with chloroform. The chloroform phase is washed with water, dried, and concentrated to dryness. The residue, dissolved in ether is methylated by the addition of diazomethane thus yielding 168 which is purified on silica gel (hexane/ethyl acetate; 4/1 then 1/1; v/v). It is a syrup $[\alpha]_D^{20} = -8.5°$ (1, chloroform). The elementary analysis and the IR spectrum confirm the expected structure for 168.

REMARK: 168 may be acetolysed and converted into a halide in the manner described in Example 25 (passage from 94 to 97).

We claim:

1. A process for synthesizing a mucopolysaccharide condensation product having from 2-12 saccharides which process comprises condensing a first protected saccharide with a second protected saccharide to form a condensation product having a 1-4 alpha linkage between the first protected saccharide and the second protected saccharide, wherein the first protected saccharide is selected from the group consisting of a D-glucosamine unit and an oligosaccharide comprised of alternating D-glucosamine and uronic acid units linked in the manner found in heparin and having a terminal D-glucosamine at the reducing end, and wherein the second protected saccharide is selected from the group consisting of a uronic acid unit and an oligosaccharide comprised of alternating D-glucosamine and uronic acid units linked in the manner found in heparin and having a terminal uronic acid at the non-reducing end, further wherein any uronic acid unit is selected from the group consisting of D-glucuronic acid and L-iduronic acid and further wherein any D-glucosamine units have nitrogen containing groups at carbon 2, which nitrogen containing groups can be treated to form an amine.

2. A process for synthesizing a protected heparinic condensation product having from 2-12 saccharide units and having semi-permanent protecting groups and permanent protecting groups as substituents at carbon positions thereon to allow selective positioning of functional groups at desired positions, and further having other protecting groups which form an ester at carboxyl groups, and having nitrogen containing groups as substituents at position 2 of D-glucosamine units, which process comprises the step of condensing a first protected saccharide with a second protected saccharide to form a protected condensation product, wherein the first protected saccharide is selected from the group consisting of a protected D-glucosamine unit and an oligosaccharide comprised of alternating protected D-glucosamine and uronic acid units linked in the manner found in heparin and having a terminal D-glucosamine at the reducing end, further wherein the first protected saccharide has a reactive group as a substituent at carbon 1 at the reducing end which reactive group allows a stereospecific linkage during the condensation, and wherein the second protected saccharide is selected from the group consisting of a protected uronic acid unit and an oligosaccharide comprised of alternating protected D-glucosamine and uronic acid units linked in the manner found in heparin and having a terminal uronic acid at the nonreducing end, wherein any uronic acid units are selected from the group consisting of D-glucuronic acid and L-iduronic acid, and wherein the protected condensation product formed has a 1-4 alpha linkage between the first protected saccharide and the second protected saccharide, the protected condensation product further having at least one each of semi-permanent protecting groups, permanent protecting groups, other protecting groups, and nitrogen containing groups as substituents at carbon positions thereon which protecting groups and nitrogen containing groups were present on the first protected saccharide and second protected saccharide, which semi-permanent protecting groups are removable in the presence of permanent protecting groups, are stable during the condensation, and allow a stereospecific linkage during the condensation, which permanent protecting groups are stable and do not migrate to different carbon positions during the removal of the semi-permanent protecting groups and the introduction of functional groups to replace the semi-permanent protecting groups, which functional groups are selected from the group consisting of $-O-SO_3$ groups and $-O-PO_3$ groups, and which permanent protecting groups also are removable in the presence of the functional groups, are stable during the condensation, and allow a stereospecific linkage during the condensation, and which other protecting groups form an ester at the carboxyl group of the uronic acid units and are stable during the condensation, and which nitrogen containing groups are substituents at carbon 2 of the D-glucosamine units, can be treated to form an amine, are stable during the condensation, and allow a stereospecific linkage during the condensation.

3. A process for synthesizing a protected heparinic condensation product having from 2-12 saccharide units and having semi-permanent protecting groups and permanent protecting groups as substituents at carbon positions thereon to allow selective positioning of functional groups at desired positions, further having other protecting groups which form an ester at the carboxyl groups, and nitrogen containing groups as substituents at carbon positions thereon, which process comprises condensing a first protected saccharide with a second protected saccharide to form a protected condensation product wherein the first protected saccharide is selected from the group consisting of a protected uronic acid unit and an oligosaccharide comprised of alternating D-glucosamine and uronic acid units linked in the manner found in heparin and having a terminal uronic acid at the reducing end, further wherein the first protected saccharide has a reactive group as a substituent at carbon 1 at the reducing end which reactive group allows the condensation to occur and which allows a stereospecific linkage during the condensation, and wherein the second protected saccharide is selected from the group consisting of a protected D-glucosamine unit and an oligosaccharide comprised of alternating protected D-glucosamine and uronic acid units linked in the manner found in heparin and having a terminal D-glucosamine at the nonreducing end, wherein any uronic acid units are selected from the group consisting of D-glucuronic acid and L-iduronic acid, and wherein the protected condensation product formed has a 1-4 beta linkage between the first protected saccharide and the second protected saccharide where the first protected saccharide is a D-glucuronic acid or an oligosaccharide having a terminal D-glucuronic acid, and wherein the protected condensation product formed has a 1-4 alpha linkage between the first protected saccharide and the second protected saccharide where the first protected saccharide is an L-iduronic acid or an oligosaccharide having a terminal L-iduronic acid, the protected condensation product further having at least one each of semi-permanent protecting groups, permanent protecting groups, other protecting groups, and nitrogen containing groups as substituents at carbon positions thereon which protecting groups and nitrogen containing groups were present on the first protected saccharide and second protected saccharide, which semi-permanent protecting groups are removable in the presence of permanent protecting groups, are stable during the condensation, and allow a stereospecific linkage during the condensation, which permanent protecting groups are stable and do not migrate to different carbon positions during the removal of semi-permanent protecting groups and the introduction of functional groups to replace the semi-permanent protecting groups, which functional groups are selected from the group consisting of —O—SO$_3$ groups and —O—PO$_3$ groups, and which permanent protecting groups also are removable in the presence of the functional groups, are stable during the condensation, and allow a stereospecific linkage during the condensation, and which other protecting groups form an ester at the carboxyl groups of the uronic acid units, and are stable during the condensation, and which nitrogen containing groups comprise nitrogen containing groups at carbon 2 of the D-glucosamine units, which nitrogen containing groups can be treated to form an amine, are stable during the condensation, and allow a stereospecific linkage during the condensation.

4. A process for synthesizing a protected heparinic condensation product having from 2-12 saccharide units and having semi-permanent protecting groups and permanent protecting groups as substituents at carbon positions thereon to allow selective positioning of functional groups at desired positions, further having other protecting groups which form an ester at the carboxyl groups and further having nitrogen containing groups at position 2 of D-glucosamine units which process comprises a first step of condensing a first protected saccharide with a second protected saccharide precursor to form a protected condensation product wherein the first protected saccharide is selected from the group consisting of a protected uronic acid unit and an oligosaccharide comprised of alternating protected D-glucosamine and uronic acid units linked in the manner found in heparin and having a terminal uronic acid at the reducing end, further wherein the first protected saccharide has a reactive group as a substituent at carbon 1 at the reducing end which reactive group allows a stereospecific linkage during the condensation, and wherein the second protected saccharide is a glucose derivative which is a D-glucosamine precursor, which D-glucosamine precursor has one or more precursor groups as substituents which are selected from the group consisting of a 1, 6 anhydro group and a 2, 3 epoxy group, further wherein any uronic acid units are selected from the group consisting of D-glucuronic acid and L-iduronic acid, and wherein the protected condensation product formed has a 1-4 beta linkage between the first protected saccharide and the second protected saccharide where the first protected saccharide is a D-glucuronic acid or an oligosaccharide having a terminal D-glucuronic acid, and wherein the protected condensation product formed has a 1-4 alpha linkage between the first protected saccharide and the second protected saccharide where the first protected saccharide is an L-iduronic acid or an oligosaccharide having a terminal L-iduronic acid, the protected condensation product further having protecting groups and precursor groups as substituents at carbon positions thereon, which protecting groups and precursor groups were present on the first and second protected saccharide, further comprising the second step of treating any 1,6 anhydro precursor group to form semi-permanent protecting groups or permanent protecting groups at carbons 1 and 6 and treating any 2, 3 epoxy precursor group to form a semi-permanent protecting group or a permanent protecting group at carbon 3 and a nitrogen containing group at carbon 2, which semi-permanent protecting groups are removable in the presence of permanent protecting groups, and which permanent protecting groups are stable and do not migrate to different carbon positions during the removal of semi-permanent protecting groups and the introduction of functional groups to replace the semi-permanent protecting groups, which functional groups are selected from the group consisting of —O—SO$_3$ groups and —O—PO$_3$ groups, and which permanent protecting groups also are removable in the presence of the functional groups, and which other protecting groups form an ester at the carboxyl groups of the uronic acid units and are stable during the condensation, and which nitrogen containing groups occupy carbon 2 of the D-glucosamine units, can be treated to form an amine, are stable during the condensation and allow a stereospecific linkage during the condensation.

5. A process according to claim 4 wherein the second protected saccharide is a glucose derivative which is a D-glucosamine precursor which contains a 1, 6 anhydro group, wherein the 1,6 anhydro group is treated with an acetolysing agent to obtain —O-acetyl semi-permanent protecting groups.

6. A process according to claim 5 wherein the D-glucosamine precursor also contains a 2, 3 epoxy group, wherein the 2, 3 epoxide group is opened with a nucleophile and the resulting OH is acetylated at the position 3 carbon to obtain an —O-acetyl semi-permanent protecting group at carbon 3 and an azide nitrogen containing group at carbon 2.

7. A process according to claim 5 wherein the D-glucosamine precursor also contains a 2, 3 epoxide group, wherein the 2, 3 epoxide group is opened with a nucleophile and the resulting OH is benzylated at the position 3 carbon to obtain an —O-benzyl permanent protecting group at carbon 3 and an azide nitrogen containing group at carbon 2.

8. A process according to claim 6 or 7 wherein the nucleophile is sodium azide and the nitrogen containing group is $N_3$.

9. A process according to claim 4 wherein the D-glucosamine unit contains a 1,6 anhydro group, comprising treating with an acetolysing agent in order to obtain an —O-acetyl group at carbon 1 of the D-glucosamine, further comprising the step of removing the acetyl group and replacing it with a reactive group in order to allow the protected condensation product to be elongated.

10. A process according to claim 9 wherein the reactive group is selected from the group consisting of bromine and chlorine.

11. A process as in claim 2, 3 or 4 wherein the functional groups are —O—$SO_3$ groups.

12. A process as in claim 11 wherein the semi-permanent protecting groups are substituents at one or more carbon positions at any of carbons 3 and 6 of D-glucosamine units, and carbons 2 and 3 uronic acid units, and wherein the permanent protecting groups are substituents at the carbons 3 and 6 of the D-glucosamine units and carbons 2 and 3 of the uronic acid units which are not occupied by the semi-permanent protecting groups.

13. The process of claim 12 wherein
 (a) The nitrogen containing groups are selected from the group consisting of
  1. $N_3$,
  2. NH-lower acyl, and
  3. NHCO-lower arylalkyl;
 (b) the protecting groups which form an ester at the carboxyl are selected from the group consisting of
  1. lower alkyl, and
  2. lower aryl;
 (c) the semi-permanent protecting groups are —O-lower acyl;
 (d) the permanent protecting groups are —O—benzyl; and
 (e) the reactive group is selected from the group consisting of
  1. halogen,
  2. O-lower imidoyl, and
  3. an orthoester formed between carbon 1 and carbon 2 of D-glucosamine.

14. The process of claim 13 wherein
 (a) The nitrogen containing groups are selected from the group consisting of
  1. $N_3$,
  2. NH-acetyl, and
  3. NHCO-benzyl;
 (b) the protecting groups which forms an ester at the carboxyl are methyl;
 (c) the semi-permanent groups are —O-acetyl;
 (d) the permanent protecting groups are —O-benzyl; and
 (e) the reactive group is selected from the group consisting of
  1. Br,
  2. Cl,
  3. an orthoester having between 3 and 6 carbons, and
  4. $C(NH)CCl_3$.

15. The process of claim 13 wherein the condensation reaction is between a halide and an OH and is carried out in a solvent medium in the presence of a catalyst.

16. The process of claim 15 wherein the solvent is an organic solvent selected from the group consisting of dichloromethane and dichloroethane and the catalyst is selected from the group consisting of a silver and a mercury salt.

17. The process of claim 16 wherein the catalyst is selected from the group consisting of trifluoromethane, silver carbonate, silver oxide, mercuric bromide and mercuric cyanide.

18. The process of claim 3 or 4 wherein the reactive group is 1,2-O-methoxyethylidene, and the condensation is carried out in a solvent which boils above 100 degrees centigrade in the presence of a catalyst.

19. The process of claim 14 wherein the reactive group is O-lower imidoyl and the condensation reaction is carried out in the presence of a catalyst at a temperature below or equal to 0 degrees centigrade.

20. A process as in claim 2 or 3 wherein the carbon 1 at the reducing end of the protected condensation product is occupied by a protecting group which is selected from the group consisting of a semi-permanent protecting group and a permanent protecting group.

21. A process as in claim 2 or 3 wherein the carbon 4 at the non-reducing end of the protected condensation product is occupied by a protecting group which is selected from the group consisting of a semi-permanent protecting group and a permanent protecting group.

22. A process as in claim 2 or 3 further wherein the carbon 1 at the reducing end of the protected condensation product is occupied by an inert protecting group, which inert protecting group is stable during the condensation and during removal of the permanent protecting groups.

23. A process for synthesizing a protected heparinic condensation product which can be elongated, having from 2 12 saccharide units and having semi-permanent protecting groups and permanent protecting groups as substituents at carbon positions thereon to allow selective positioning of functional groups at desired positions, and further having other protecting groups which form an ester at carboxyl groups, and having nitrogen containing groups as substituents at position 2 of D-glucosamine units, and further having temporary groups positioned thereon to allow elongation of the protected condensation product, which process comprises condenses a first protected saccharide with a second protected saccharide to form a protected condensation product
 wherein the first protected saccharide is selected from the group consisting of a protected D-glucosamine unit and an oligosaccharide comprises of alternating protected D-glucosamine and uronic acid units linked in the manner found in heparin and having a terminal D-glucosamine at the reducing end, further wherein the first protected saccharide has a reactive group as a substituent at carbon 1 at the reducing end which reactive group allows the condensation to occur and also allows a stereo-specific linkage during the condensation, and wherein the second protected saccharide is selected from the group consisting of a protected uronic acid unit and an oligosaccharide comprised of alternating protected D-glucosamine and uronic acid units linked in the manner found in heparin and having a terminal uronic acid at the nonreducing end, wherein any uronic acid is selected from the group consisting of D-glucuronic acid and L-iduronic acid, and wherein the protected condensation product has a 1-4 alpha linkage between the first protected saccharide and the second protected saccharide, the protected condensation product further having at least one each of semi-permanent protecting groups, permanent protecting groups, temporary protecting groups, other protecting groups, and nitrogen containing groups as substituents at carbon positions thereon which protecting groups and nitrogen containing groups were present on the first protected saccharide and second protected saccharide, which semi-permanent protecting groups are removable in the presence of permanent protecting groups, are stable during the condensation, and allow a stereospecific linkage during the condensation, which permanent protecting groups are stable and do not migrate to different carbon positions during introduction of functional groups to replace the semi-permanent protecting groups, which functional groups are selected from the group consisting of —O—$SO_3$ groups and —O—$PO_3$ groups, and which permanent groups also are removable in the presence of the functional groups, are stable during the condensation, and allow a stereospecific linkage during the condensation, which other protecting groups form an ester at the carboxyl grups of the uronic acid units, and are stable during the condensation, which temporary protecting groups are substituents at any of carbon 1 at the reducing end of the protected condensation product and carbon 4 at the non-reducing end of the protected condensation product and are removable in the presence of the semi-permanent protecting groups and permanent protecting groups in order to permit elongation of the protected condensation product, and which nitrogen containing groups are substituents at carbon 2 of the D-glucosamine units, can be treated to form an amine, are stable during the condensation, and allow a stereospecific linkage during the condensation.

24. A process for synthesizing a protected heparinic condensation product which can be elongated, having from 2-12 saccharide units and having semi-permanent protecting groups and permanent protecting groups as substituents at carbon positions thereon to allow selective positioning of functional groups at desired positions, and further having other protecting groups which form an ester at carboxyl groups, and having nitrogen containing groups as substituents at position 2 of D-glucosamine units, and further having temporary groups positioned thereon to allow elongation of the protected condensation product, which process comprises condensing a first protected saccharide with a second protected saccharide to form a protected condensation product wherein the first protected saccharide is selected from the group consisting of a protected uronic acid unit and an oligosaccharide comprised of alternating protected D-glucosamine and uronic acid units linked in the manner found in heparin and having a terminal uronic acid at the reducing end, further wherein the first protected saccharide has a reactive group as a substituent at carbon 1 at the reducing end, which reactive group allows a stereoscopic linkage during the condensation, and wherein the second protected saccharide is selected from the group consisting of a protected D-glucosamine unit and an oligosaccharide comprised of alternating protected D-glucosamine and uronic acid units linked in the manner found in heparin and having a termnal D-glucosamine at the nonreducing end, wherein any uronic acid is selected from the group consisting of D-glucuronic acid and L-iduronic acid, and wherein the protected condensation product has a 1-4 beta linkage between the first protected saccharideand the second protected saccharide where the first protected saccharide is a D-glucuronic acid or unit or an oligosaccharide having a terminal D-glucuronic acid, and a 1-4 alpha linkage between the first protected saccharide and the second protected saccharide where the first protected saccharide is an L-iduronic acid unit or an oligosaccharide having a terminal L-iduronic acid, the protected condensation product further having at least one each of semi-permanent protecting groups, permanent protecting groups, temporary protecting groups, other protecting groups, and nitrogen containing groups as substituents at carbon positions thereon which protecting groups and nitrogen containing groups were present on the first protected saccharide and second protected saccharide, which semi-permanent protecting groups are removable in the presence of permanent protecting groups, are stable during the condensation, and allow a stereospecific linkage during the condensation, which permanent protecting groups are stable and do not migrate to different carbon positions during introduction of functional groups to replace the semi-permanent protecting groups, which functional groups are selected from the group consisting of —O—$SO_3$ groups and —O—$PO_3$ groups, and which permanent protecting groups also are removable in the presence of the functional groups, are stable during the condensation, allow a stereospecific linkage during the condensation, which other protecting groups form an ester at the carboxyl groups of the uronic acid units and are stable during the condensation, which temporary protecting groups are substituents at any of carbon 1 at the reducing end of the protected condensation product and carbon 4 at the nonreducing end of the protected condensation product, and are removable in the presence of the semi-permanent protecting groups and permanent protecting groups in order to permit elongation of the protected condensation product, and which nitrogen containing groups are substituents at carbon 2 of the D-glucosamine units, can be treated to form an amine, are stable during the condensation, and allow a stereospecific linkage during the condensation.

25. A process as in claim 23 or 24 wherein the functional groups are —O—$SO_3$ groups.

26. A process as in claim 25 wherein the semi-permanent protecting groups are substituents at one or more carbon positions at any of carbons 3 and 6 of D-glucosamine units, and carbons 2 and 3 or uronic acid units, and wherein the permanent protecting groups are substituents at the carbons 3 and 6 of the D-glucosamine units and carbons 2 and 3 of the uronic acid units which are not occupied by the semi-permanent protecting groups.

27. A process according to claim 26 further comprising the steps of removing a temporary protecting group at carbon one at the reducing end of the protected condensation product, substituting a reactive group and performing a second condensation to form an elongated protected condensation product comprised of alternating protected D-glucosamine and uronic acid units linked in the manner found in heparin and having protecting groups thereon.

28. A process according to claims 26 further comprising the steps of removing the temporary group at carbon 4 of the nonreducing end of the protected condensation product and performing a second condensation to form an elongated condensation product comprised of alternating protected D-glucosamine and uronic acid units linked in the manner found in heparin and having protecting groups thereon.

29. The process of claim 26 wherein
(a) The nitrogen containing groups are selected from the group consisting of
1. $N_3$,
2. NH-lower acyl, and
3. NHCO-lower arylalkyl;
(b) the protecting groups at the carboxyl are selected from the group consisting of
1. lower alkyl, and
2. lower aryl;
(c) the semi-permanent protecting groups are —O-lower acyl;
(d) the permanent protecting groups are —O-benzyl; and
(e) the reactive group is selected from the group consisting of
1. halogen,
2. —O-lower imidoyl, and
3. an orthoester formed between carbon 1 and carbon 2 of D-glucosamine;
(f) the temporary group is selected from the group consisting of
1. —O-lower acyl,
2. —O-allyl,
3. —O-propenyl,
4. halogenated —O-lower acyl, and
5. —O—p-methoxy benzoyl.

30. The process of claim 29 wherein
(a) The nitrogen containing groups are selected from the group consisting of
1. $N_3$,
2. NH-acetyl, and
3. NHCO-benzyl;
(b) The protecting groups which forms an ester at the carboxyl are methyl;
(c) The semi-permanent groups are —O-acetyl;
(d) The permanent protecting groups are —O-benzyl; and
(e) the reactive group is selected from the group consisting of
1. Br,
2. Cl,
3. an orthoester having between 3 and 6 carbons, and
4. $C(NH)CCl_3$;
(f) The temporary protecting groups are selected from the group consisting of
2. —O-acetyl,
2. —O-allyl,
3. —O-propenyl,
4. monochloro-O-acetyl,
5. trichloro-O-acetyl, and
6. —O—p-methoxy benzoyl.

31. A process for selectively positioning sulfate groups or phosphate groups on a protected heparinic polysaccharide having from 2–12 units, which polysaccharide is comprised of alternating D-glucosamine and uron acid units linked in the manner found in heparin and having at least one each as substituents of semi-permanent protecting groups, permanent protecting groups other protecting groups which form an ester at the carboxyl groups of the uronic acid units, and nitrogen containing groups at carbon 2 of the D-glucosamine units, wherein the permanent protecting groups are stable and do not migrate to other carbon positions during removal of the semi-permanent protecting groups and the introduction of functionalgroups, and wherein any uronic acid units are selected from the group consisting of D-glucuronic acid and L-iduronic acid, which process comprises the steps of
(a) removing the semi-permanent protecting groups,
(b) introducing functional groups in place of the semi-permanent protecting groups, which functional groups are selected from the group consisting of —O—$SO_3$ groups and —O—$PO_3$ groups, and
(c) removing the permanent protecting groups and converting the nitrogen containing group into an amine group.

32. A process as in claim 31 wherein the functional groups are —O—$SO_3$ groups.

33. A process as in claim 32 wherein the semi-permanent protecting groups are substituents at one or more carbon positions at any of carbons 3 and 6 of D-glucosamine units, and carbons 2 and 3 of uronic acid units, and wherein the permanent protecting groups are substituents at the carbons 3 and 6 of the D-glucosamine units and carbons 2 and 3 of the uronic acid units which are not occupied by the semi-permanent protecting groups.

34. The process of claim 33 wherein
(a) The nitrogen containing groups are selected from the group consisting of
1. $N_3$,
2. NH-lower acyl, and
3. NHCO-lower arylalkyl;
(b) the protecting groups at the carboxyl are selected from the group consisting of
1. lower alkyl, and
2. lower aryl;
(c) the semi-permanent protecting groups are —O-lower acyl; and
(d) the permanent protecting groups are —O-benzyl.

35. The process of claim 34 wherein
(a) The nitrogen containing groups are selected from the group consisting of
1. $N_3$,
2. NH-acetyl, and
3. NHCO-benzyl;
(b) The protecting groups which forms an ester at the carboxyl are methyl;
(c) The semi-permanent groups are —O-acetyl; and (d) The permanent protecting groups are —O-benzyl.

36. A process as in claim 31 further comprising the step of substituting the amine grop with a group selected from the group consisting of SO₃ and acyl.

37. A process as in claim 36 wherein the amine group is substituted with a group selected from the group consisting of SO₃ and acetyl.

38. A process ac in claim 37 further comprising removing the protecting groups at the carboxyl groups of the uronic acid units.

39. The process of claim 38 which further comprises salifying the COO⁻ with an alkaline metal cation.

40. The process of claim 31 wherein the semi-permanent protecting groups are acetyl and are hydrolysed with a strong base followed by reacton with a sulfation agent.

41. The process of claim 40 wherein following introduction of the functional group —O—SO₃ the compound formed is purified by fractionation.

42. The process of claim 41 wherein following fractionation of the compound, the compound is passed through a sodium ion exchange column.

43. A process for selectively positioning sulfate groups or phosphate groupson a protected heparinic polysaccharide having from 2–12 units, which protected heparinic polysaccharide is comprised of alternating units of a first unit and a second unit wherein the first unit is selected from the group consisting of a D-glucosamine, a neutral sugar analog of D-glucosamine, and a desoxy sugar analog of D-glucosamine, and wherein the second unit is selected from the group consisting of a uronic acid, a neutral sugar analog of uronic acid, and a dexoy sugar analog of uronic acid, further wherein any uronic acid is selected from the group consisting of D-glucuronic acid and L-iduronic acid, the first and second unit being linked in the manner found in heparin and having at least on each as substituents of semi-permanent protecting groups, permanent protecting groups, other protecting groups which form an ester at the carboxyl groups of the uronic acid units, and nitrogen containing groups at carbon 2 of the D-glucosamine units wherein the permanent protecting groups are stable and do not migrate to other carbon positions during removal of the semi-permanent protecting groups and the introduction of functional groups, which process comprises the steps of (a) removing the semi-permanent protecting groups, (b) introducing functional groups in place of the semi-permanent protecting groups, which functional groups are selected from the group consisting of —O—SO₃ groups and —O—PO₃ groups, and (c) removing the permanent protecting groups and converting the nitrogen containing group into an amine group.

44. A substantially pure compound of a single structure, which compound is selected from the group consisting of:

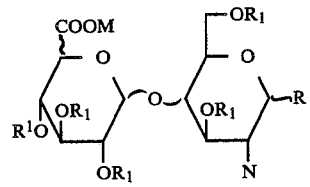

I

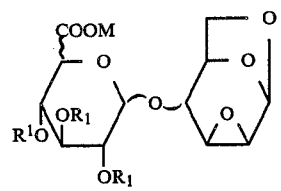

II

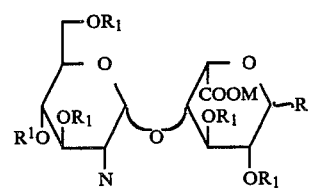

III

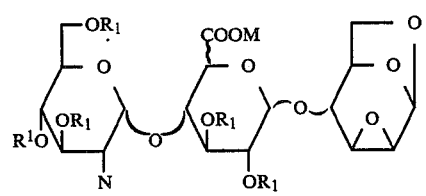

IV

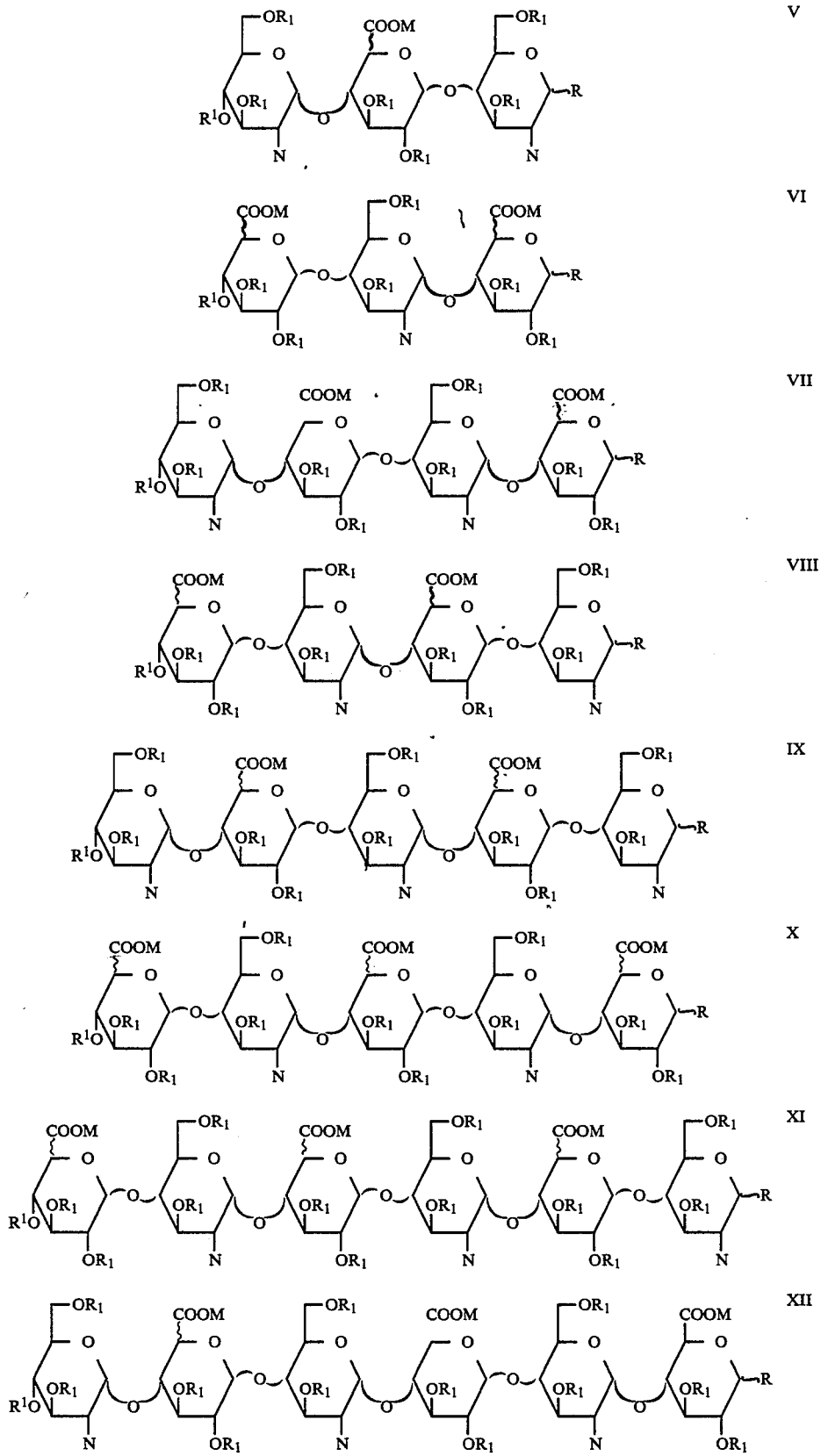
wherein
R₁ substituents are not the same, and are selected from the group consisting of
(a) semi-permanent protecting groups which semi-permanent protecting groups are removable in the presence of permanent protecting groups, are stable during any condensation employed to obtain the compound and allow a stereospecific linkage during the condensation, and are stable during removal of any temporary group,
(b) permanent protecting groups which permanent protecting groups are stable and do not migrate to different carbon positions during removal of the semi-permanent protecting groups and the introduction of functional groups to replace the semi-permanent protecting groups, which functional groups are selected from the group consisting of SO₃ groups and PO₃ groups, and which permanent protecting groups also are removable in the presence of the functional groups, are stable during the condensation, and which allow a stereospecific linkage during the condensation, and which permanent protecting groups are stable during removal of any temporary protecting group, M is a protecting group which forms an ester at the carboxyl groups, and is stable during any condensation employed to obtain the compound, N is a nitrogen containing group which may be treated to form an amine, and which allows a stereospecific linkage during ay condensation employed to obtain the compound, R is selected from the group consisting of:
(a) a temporary protecting group which can be removed in the presence of a semi-permanent protecting groups and permanent protecting groups in order to permit elongation of the compound and which is stable during any condensation employed to obtain the compound,
(b) a permanent protecting group,
(c) a reactive group which can be employed in order to perform a condensation to form a 1-4 linkage as found in heparin in order to elongate the compound, and which reactive group was positioned following removal of a temporary protecting group and which allows a stereospecific linkage during the condensation,
(d) an inert protecting group, which is stable during removal of the temporary protecting groups, semi-permanent protecting groups and permanent protecting groups, and R' is selected from the group consisting of
(a) a temporary protecting group,
(b) a permanent protecting group, and
(c) an OH group.

45. The substantially pure compound of claim 43 wherein the compound can be elongated and R is selected from the group consisting of a temporary protecting group and a reactive group.

46. The substantially pure compound of claim 43 wherein the compound can be elongated and R' is selected from the group consisting of a temporary protecting group and OH.

47. The substantially pure compound IX of claim 46 wherein the R₁ substituents are selected from the group consisting of semi-permanent protecting groups and permanent protecting groups, wherein R is a permanent protecting group, wherein R' is a permanent protecting group, and wherein the semi-permanent protecting groups are sp groups and wherein the permanent protecting groups are p groups, which compound has the formula

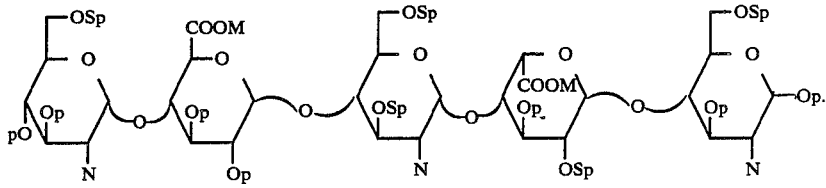

48. The substantially pure compound of any of claims 44, 45 or 46 wherein
(a) any nitrogen containing group is selected from the group consisting of
 1. N₃,
 2. NH-lower acyl, and
 3. NHCO-lower arylalkyl;
(b) any protecting group at the carboxyl is selected from the group consisting of
 1. lower alkyl, and
 2. aryl;
(c) any semi-permanent protecting group is lower acyl;
(d) any temporary protecting group is selected from the group consisting of
 1. -O-lower acyl,
 2. -O-allyl,
 3. -O-propenyl,
 4. halogenated -O-lower acyl, and
 5. -O-p-methoxybenzoyl;
(e) any permanent protecting group is benzyl,
(f) any reactive group is selected from the group consisting of
 1. halogen,
 2. lower imidoyl, and
 3. an orthoester formed between the carbon 1 and carbon 2 positions where the reactive group occupies a position at carbon 1 of a uronic acid unit,
(g) any inert protecting group is -O-lower alkyl, and
(h) any functional group is SO₃.

49. The substantially pure compound of claim 48 wherein
(a) any nitrogen containing group is selected from the group consisting of
 1. N₃,
 2. NH-acetyl, and
 3. NHCO-benzyl;
(b) any protecting group which forms an ester at the carboxyl is methyl;
(c) any semi-permanent group is acetyl;
(d) any temporary group is selected from the group consisting of
 1. -O-acetyl,
 2. -O-benzyl,
 3. -O-allyl,
 4. -O-propenyl,
 5. monochloro-O-acetyl,
 6. trichloro-O-acetyl, and
 7. -O-p-methoxybenzoyl;

(e) any permanent group is benzyl;
(f) any reactive group is selected from the group consisting of
1. Br,
2. Cl,

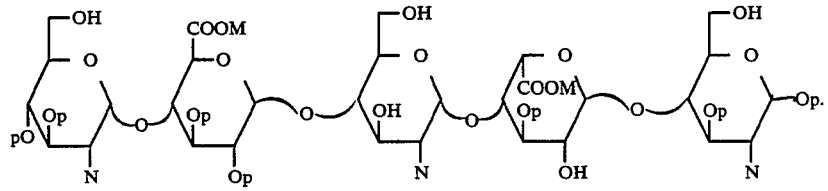

3. an orthoester having between 3 and 6 carbons, and
4. C(NH)CCl$_3$;
(g) any inert blocking group is an —O-lower alkyl group having between 1 and 4 carbons, and
(h) any functional group is SO$_3$.

50. A substantially pure compound of a single structure, which compound is selected from the group consisting of: Compounds I, III, V, VI, VII, VIII, IX, X, XI and XII wherein R$_1$ substituents are not the same, and are selected from the group consisting of
(a) OH groups, and
(b) permanent protecting groups, which permanent protecting groups are stable and do not migrate to different carbon positions during removal of the semi-permanent protecting groups and the introduction of functional groups to replace the semi-permanent protecting groups, which functional groups are selected from the group consisting of SO$_3$ groups and PO$_3$ groups, which permanent protecting groups also are removable in the presence of the functional groups, are stable during the condensation, and which allow a stereospecific linkage during any condensation employed to obtain the compound, and which permanent protecting groups are stable during removal of any temporary protecting group, M is a protecting group which forms an ester at the carboxyl groups, and is stable during any condensation employed to obtain the compound, N is a nitrogen containing group which can be treated to form an amine, and which allows a stereospecific linkage during any condensation employed to obtain the compound, R is selected from the group consisting of:
(a) a permanent protecting group,
(b) an inert protecting group which is stable during removal of the temporary protecting groups, semi-permanent protecting groups and permanent protecting groups, and R' is a permanent protecting group.

51. The substantially pure compound IX of claim 50 wherein R$_1$ substituents are selected from the group consisting of OH groups and permanent protecting groups, wherein R is a permanent protecting group, wherein R' is a permanent protecting group, and wherein the permanent protecting groups are p groups, which compound has the formula 52. A substantially pure compound of a single structure, which compound is selected from the group consisting of: Compounds I, III, V, VI, VII, VIII, IX, X, XI and XII wherein R$_1$ substituents are not the same, and are selected from the group consisting of
(a) functional groups which are selected from the group consisting of SO$_3$ groups and PO$_3$ groups,
(b) permanent protecting groups, which permanent protecting groups are stable and do not migrate to different carbon positions during removal of the semi-permanent protecting groups and the introduction of the functional groups to replace semi-permanent protecting groups, which permanent protecting groups also are removable in the presence of the functional groups, are stable during the condensation, and which allow a stereospecific linkage during any condensation employed to obtain the compound, and which permanent protecting groups are stable during removal of any temporary protecting group, M is a protecting group which forms an ester at the carboxyl groups, and is stable during any condensation employed to obtain the compound, N is a nitrogen containing compound which can be treated to form an amine, and which allows a stereospeific linkage during any condensation employed to obtain the compound, R is selected from the group consisting of:
(a) a permanent protecting group,
(b) an inert protecting group which is stable during removal of the temporary protecting groups, semi-permanent protecting groups and permanent protecting groups, and R' is a permanent protecting group.

53. The substantially pure compound IX of claim 52 wherein R$_1$ substituents are selected from the group consisting of SO$_3$ groups and permanent protecting groups, wherein R is a permanent protecting group, and wherein R' is a permanent protecting group, and wherein the permanent protecting groups are p groups, which compound has the formula

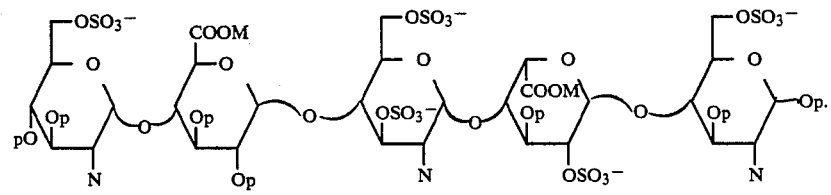

54. A substantially pure compound of a single structure, which compound is selected from the group consisting of: Compounds I, III, V, VI, VII, VIII, IX, X, XI and XII wherein $R_1$ substituents are not the same, and are selected from the group consisting of
(a) functional groups which are selected from the group consisting of $SO_3$ groups and $PO_3$ groups, and
(b) OH groups, M is a protecting group which forms an ester at the carboxyl groups, and is stable during any condensation employed to obtain the compound, N is the same or different and is selected from the group consisting of
(a) an amine,
(b) NH acetyl, and
(c) NH $SO_3$ R is selected from the group consisting of:
(a) An OH group,
(b) an inert protecting group which is stable during removal of the temporary protecting groups, semi-permanent protecting groups and permanent protecting groups, and R' is OH.

55. The substantially pure compound IX of claim 54 wherein $R_1$ substituents are selected from the group consisting of $SO_3$ groups and OH groups, wherein R is an OH group, R' is an OH group, and N is selected from the group consisting of an amine, NH acetyl, and NH $SO_3$ which compound has the formula

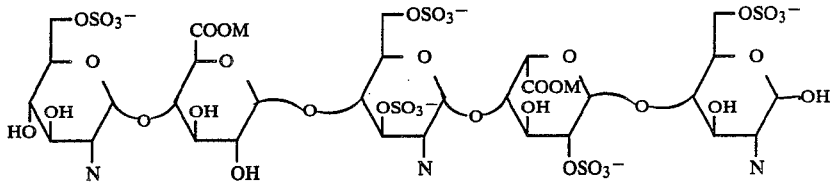

56. The substantially pure compound of claim 54 wherein N is selected from the group consisting of NH acetyl and NH $SO_3$ and wherein M is removed and the compound forms an anion.

57. The substantially pure compound IX of claim 56 wherein sp is $SO_3$ and p is OH, and N selected from the group consisting of NH acetyl and NH $SO_3$ and M is removed to form an anion of the compound, which compound has the formula

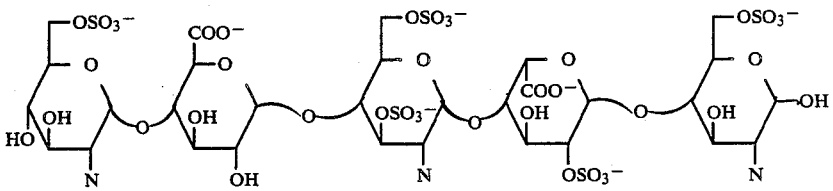

58. A substantially pure heparin chain of a single structure comprised of 2 to 12 saccharide units.

59. A substantially pure oligosaccharide of a single structure comprised of 2 to 12 alternating D-glucosamine and uronic acid units, wherein the uronic acid units are selected from the group consisting of D-glucuronic acid and L-iduronic acid and —O—$SO_3$ groups are positioned at any but not all of carbons 3 and 6 of the D-glucosamine units and carbons 2 and 3 of the uronic acid units and further wherein linkages between D-glucosamine and uronic acid are of the 1-4 alpha type, and linkages between L-iduronic acid and D-glucosamine are of the 1-4 alpha type, and linkages between D-glucuronic acid and D-glucosamine are of the 1-4 beta type.

60. A synthetic pure compound of the formula

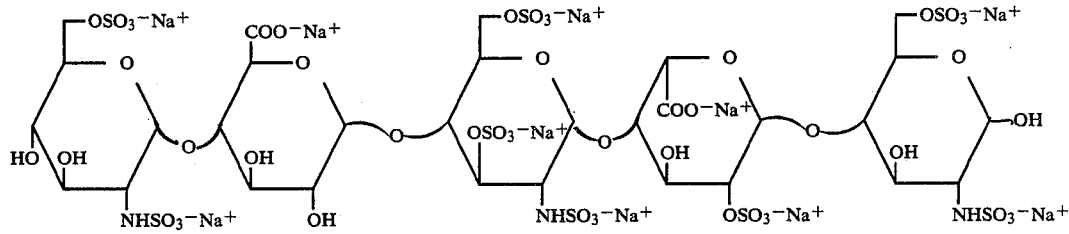

61. An antithrombotic pharmaceutical composition which comprises a pharmaceutically acceptable carrier and the compound of claim 60.

* * * * *

UNITED STATES PATENT AND TRADEMARK OFFICE
CERTIFICATE OF CORRECTION

PATENT NO. : 4,818,816
DATED     : April 4, 1989
INVENTOR(S) : Petitou, et al.

It is certified that error appears in the above—identified patent and that said Letters Patent is hereby corrected as shown below:

The following should be added to the title page under Foreign Application Priority Data

| FOREIGN/PCT APPLICATIONS | FRANCE | 8108472 | 04/28/81 |
|---|---|---|---|
| | FRANCE | 8200621 | 01/15/82 |
| | FRANCE | 8201575 | 02/01/82 |
| | FRANCE | 8202526 | 02/16/82 |
| | FRANCE | 8209392 | 05/28/82 |
| | FRANCE | 8210892 | 06/22/82 |
| | FRANCE | 8210891 | 06/22/82 |
| | FRANCE | 8211679 | 07/02/82 |
| | FRANCE | 8213804 | 08/06/82 |
| | FRANCE | 8215803 | 09/20/82 |
| | FRANCE | 8215804 | 09/20/82 |
| | FRANCE | 8218003 | 10/27/82 |
| | PCT | PCT/FR82/0076 | 04/28/82 |

UNITED STATES PATENT AND TRADEMARK OFFICE
CERTIFICATE OF CORRECTION

PATENT NO. : 4,818,816
DATED : April 4, 1989
INVENTOR(S) : Petitou, et al.

It is certified that error appears in the above—identified patent and that said Letters Patent is hereby corrected as shown below:

Claim 13, line 19, at Col. 73, line 58 should read:

"3. an orthoester formed between carbon 1 and carbon 2 of a uronic acid unit."

Claim 29, line 19, at Col. 77, line 46 should read:

"3. an orthoester formed between carbon 1 and carbon 2 of a uronic acid unit."

Claim 49, line 27, at Col. 85, line 18 should read:

"3. an orthoester formed between carbon 1 and carbon 2 of a uronic acid unit."

Claim 14, line 18, at Col. 73, line 9, should read:

"4. $OC(NH)CCl_3$."

Claim 30, line 18, at Col. 78, line 3, should read:

"4. $OC(NH)CCl_3$."

Claim 48, line 25 at Col. 84, line 34, should read:

"2. O-lower imidoyl"

UNITED STATES PATENT AND TRADEMARK OFFICE
CERTIFICATE OF CORRECTION

PATENT NO. : 4,818,816
DATED : April 4, 1989
INVENTOR(S) : Petitou, et al.

It is certified that error appears in the above—identified patent and that said Letters Patent is hereby corrected as shown below:

At Col. 80, compounds I - IV should be:

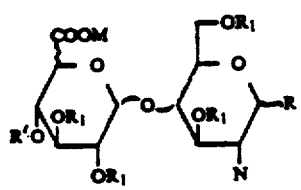   I

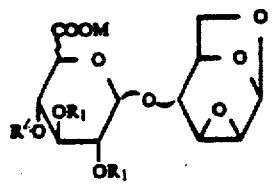   II

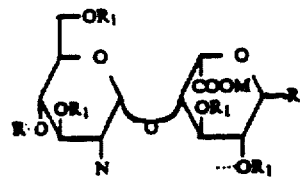   III

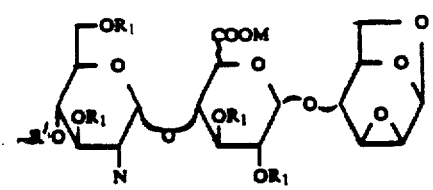   IV

UNITED STATES PATENT AND TRADEMARK OFFICE
CERTIFICATE OF CORRECTION

PATENT NO. : 4,818,816
DATED : April 4, 1989
INVENTOR(S) : Petitou, et al.

It is certified that error appears in the above—identified patent and that said Letters Patent is hereby corrected as shown below:

At Col. 81, compounds V - VIII should be:

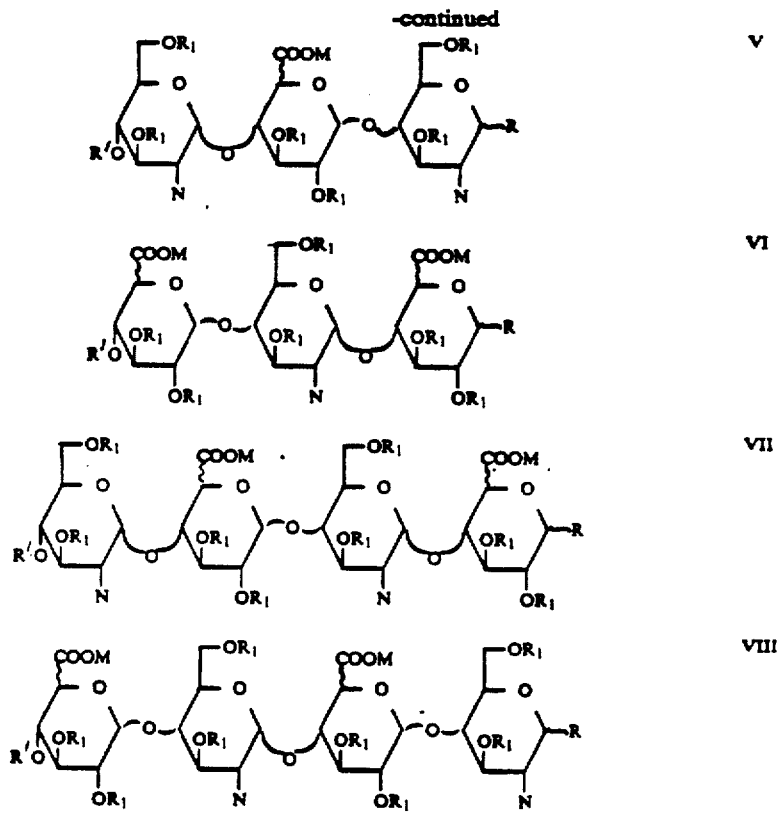

UNITED STATES PATENT AND TRADEMARK OFFICE
CERTIFICATE OF CORRECTION

PATENT NO. : 4,818,816
DATED : April 4, 1989
INVENTOR(S) : Petitou, et al.

It is certified that error appears in the above—identified patent and that said Letters Patent is hereby corrected as shown below:

At Col. 81, compounds IX - XII should be:

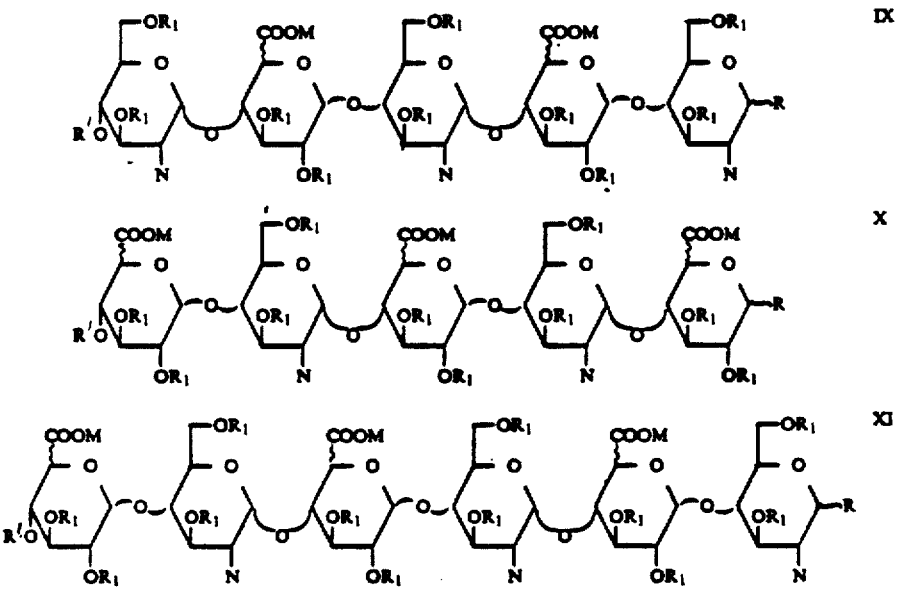

UNITED STATES PATENT AND TRADEMARK OFFICE
CERTIFICATE OF CORRECTION

PATENT NO. : 4,818,816
DATED : April 4, 1989
INVENTOR(S) : Petitou, et al.

It is certified that error appears in the above-identified patent and that said Letters Patent is hereby corrected as shown below:

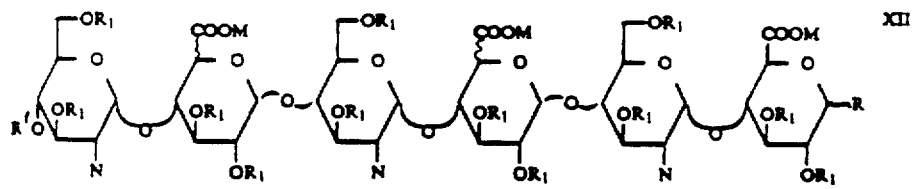

Signed and Sealed this

Seventeenth Day of December, 1991

Attest:

HARRY F. MANBECK, JR.

*Attesting Officer*      Commissioner of Patents and Trademarks